(12) United States Patent
Church et al.

(10) Patent No.: US 12,183,440 B2
(45) Date of Patent: Dec. 31, 2024

(54) COMPUTER SYSTEM, METHOD, AND DEVICE FOR VERIFYING AN IMMUNIZATION STATUS

(71) Applicant: FinVentures Canada Inc., Kitchener (CA)

(72) Inventors: Mark Church, Waterloo (CA); Zachary Packull, Cambridge (CA)

(73) Assignee: FinVentures Canada Inc., Kitchener (CA)

( * ) Notice: Subject to any disclaimer, the term of this patent is extended or adjusted under 35 U.S.C. 154(b) by 336 days.

(21) Appl. No.: 17/701,572

(22) Filed: Mar. 22, 2022

(65) Prior Publication Data

US 2022/0301667 A1    Sep. 22, 2022

Related U.S. Application Data

(60) Provisional application No. 63/164,150, filed on Mar. 22, 2021.

(51) Int. Cl.
    G16H 10/60    (2018.01)
    G16H 10/65    (2018.01)
    G16H 40/20    (2018.01)

(52) U.S. Cl.
    CPC ................................ *G16H 10/60* (2018.01)

(58) Field of Classification Search
    CPC ......... G16H 10/60; G16H 10/65; G16H 40/20
    See application file for complete search history.

(56) References Cited

U.S. PATENT DOCUMENTS

| 7,908,155 B2 | 3/2011 | Fuerst et al. |
| 7,949,546 B1 | 5/2011 | Klieman et al. |

(Continued)

OTHER PUBLICATIONS

Canadian Intellectual Property Office, Office Action for CA Patent App. No. 3152908, Jan. 16, 2023.

(Continued)

*Primary Examiner* — Shirley X Zhang
(74) *Attorney, Agent, or Firm* — Own Innovation; James W. Hinton

(57) ABSTRACT

Systems, methods, and devices for verification of an immunization status of an individual and for secure data portability are provided. A system for verifying an immunization status of an individual includes a verification device, a vault computing device, and an immunization record database server. The verification device includes a web terminal configured to send an immunization status request including identifying data about the individual. The vault computing device receives the immunization status request and generates and sends an immunization record request including an insurance plan number corresponding to the individual. The immunization record database server has access to an immunization record database and retrieves immunization record data from the immunization record database using the insurance plan number and sends the immunization record data to the vault computing device. The vault computing device generates immunization status data representing the immunization status of the individual from the immunization record data and sends the immunization status data to the verification device. The verification device receives the immunization status data via the web terminal and displays the immunization status data in a user interface.

22 Claims, 19 Drawing Sheets

(56) References Cited

U.S. PATENT DOCUMENTS

| | | |
|---|---|---|
| 2004/0117215 A1 | 6/2004 | Marchosky |
| 2014/0156304 A1 | 6/2014 | Michon et al. |
| 2015/0088545 A1 | 3/2015 | Daub et al. |
| 2015/0227690 A1 | 8/2015 | St. Jacques |
| 2020/0321088 A1 | 10/2020 | Liege et al. |
| 2021/0104304 A1* | 4/2021 | Davidovics ............. H04W 4/80 |
| 2023/0385450 A1* | 11/2023 | Bessette ................. G16H 10/20 |

OTHER PUBLICATIONS

Canadian Intellectual Property Office, Office Action for CA Patent App. No. 3152908, Jul. 14, 2023.
Canadian Intellectual Property Office, Office Action for CA Patent App. No. 3183996, May 31, 2024.

* cited by examiner

| Card Number | Procedure | Date | Batch/Serial Number | Exemption Code |
|---|---|---|---|---|
| 123456789 | Moderna 1 | March 15 2021 | 34454321 | None |
| 123456789 | Moderna 2 | March 29 2021 | 34454322 | None |
| 123456789 | COVID antibody test | April 23 2021 | 23399032 | None |
| 987654321 | Pfizer 1 | April 02 2021 | 34456765 | None |
| 546673772 | None | None | None | Severe Allergy |

FIG. 6

COMPUTER SYSTEM, METHOD, AND DEVICE FOR VERIFYING AN IMMUNIZATION STATUS

TECHNICAL FIELD

The following relates generally to controlled sharing of sensitive data about an individual through networked systems, and more particularly to systems and methods for provisioning authorized access to an individual's medical data for the purposes of verifying an immunization status of the individual.

INTRODUCTION

Mass disease or infection events, such as pandemics (e.g. Covid-19) and epidemics can significantly impact not only the health of populations but also their way of life. In many cases, such mass infection events revolve around viruses or pathogens which may be novel or previously identified. Transmissibility of viruses or other pathogens can be high. To combat high transmissibility and spread, measures may be taken that limit what people can do and where they can go. This can cause closing of businesses and schools (at least in-person attendance). Such closings can have drastic and long lasting economic, social, psychological, and medical impacts.

While immunization of populations through vaccination of individuals is a critical component of managing the rate and prevalence of infection, it may not be enough to enable a return to a normal way of life. Records of vaccinations are critical to knowing who has been vaccinated (or has an up to date immunization record) and who has not, so that entities, such as businesses, schools, and public authorities, are able to make judgements on individual access at points of entry to limit risk of exposure and to protect both attendees and the entity permitting entrance. In addition, institutions may need to know their overall compliance level with mandated or voluntary regulations, to assist in determining if they are providing a safe space.

Presently, upon vaccination an individual may receive a card (hard copy) indicating a vaccination status and such status may be recorded in a database under the control of relevant health authority.

There are also concerns with providing access to sensitive or personal data (e.g. medical records) to third parties for the purposes of verifying an immunization status. The manner in which such data is accessed, processed, and delivered should be secure and restrict the amount of sensitive data exposure to third parties. Such an approach is in the interests of all parties involved: those whom the data is about, those who hold the data that needs to be accessed, and those who need to confirm some aspect of the data.

It may be desired to be able to verify an immunization status of an individual when the individual is present (in-person verification scenario) or in advance without the need for the individual to be present (remote verification scenario).

Further, approaches to immunization status verification may be desired that address situations in which there is a non-structured relationship between the party doing the verifying and the party being verified or where there is a structured relationship between the parties. Generally, non-structured relationships generally refer to situations in which the verifying party does not hold data about the individual being verified (i.e. the individual is generally unknown to the verifying party). Examples of non-structured relationships may include an individual attending a restaurant, a sporting event, a concert, public transit, etc. In contrast, structured relationships correspond to relationships in which the verifying party holds some information about the individual to be verified. Examples of structured relationships include employee-employer and student-school. In Structured relationships may be ad hoc, such as in the case of an airline passenger planning to take a flight on an airline, or ongoing, such as in the case of a student or employee.

In structured relationships, it may be desired to know the status of multiple individuals (e.g. all the students at a school) or to know statuses on an ongoing basis. This may further enable the verifying party to manage by exception, which may significantly reduce the effort required in managing immunization statuses of many individuals. Further, structured relationships may be leveraged to enable individuals to securely drive their information to the verifying party in the structured relationship in a secure manner such that the verifying party can access the information (or some aspect of it) and manage the information to confirm immunization statuses other than through an in-person verification step.

More generally, there is a desire for new technical approaches to sharing data between users in a secure and controlled (permissioned) manner, where only the data needed by the recipient is provided to the recipient and where holding or storage of data of the data provider user by intermediaries or other parties in the system is limited as much as possible. The ability of a first user to remotely allow access to their data in a secure and permissioned manner to a second user, and for that data to include only the data needed by the second user, may have numerous applications. Particular examples include applications in which sensitive data, such as medical data or financial data, is accessed or processed for some end purpose (e.g. verify an immunization status, execute an electronic financial transaction). Remote driving of data may include cases in which data is driven or pushed by the first user and cases in which permission is granted for the second user to pull data.

Accordingly, there is a need for an improved system and method for verifying an immunization status of an individual in an in-person or remote context. Also needed are improved systems and methods for enabling secure, remote data portability through provisioning access to a first user to data (e.g. sensitive data) about a second user in a networked system in a secure and controlled manner that overcomes at least some of the disadvantages of existing systems and methods.

SUMMARY

A system for verifying an immunization status of an individual is provided. The system includes: a verification device including a web terminal configured to send an immunization status request, the immunization status request including identifying data about the individual; a vault computing device configured to receive the immunization status request and generate and send an immunization record request including an insurance plan number corresponding to the individual; an immunization record database server having access to an immunization record database, the immunization record database server configured to retrieve immunization record data from the immunization record database using the insurance plan number and send the immunization record data to the vault computing device; the vault computing device further configured to generate immunization status data representing the immunization status of the individual from the immunization record data with respect to an immunization policy and send the immunization status data to the verification device; and the verification device further configured to receive the immunization status data via the web terminal and display the immunization status data in a user interface.

The identifying data (or identifying element) may be an encoded representation of the identifying data decodable by the vault computing device to obtain the identifying data. The obtained identifying data may be the insurance plan number. The identifying data may be an encoded representation of the insurance plan number decodable by the vault computing device to obtain the insurance plan number. The identifying data may be an alternate authentication credential used to obtain the insurance plan number. The identifying data may be contact data for sending an electronic message to the individual to obtain the insurance plan number.

The immunization status data may be a binary status indicator of either a pass status or fail status. The immunization status data may also be a number, colour, or symbol representing a current level of immunization for an individual.

A system for in-person verification of an immunization status of an individual is provided. The system includes: an in-person verification device including: an input device for receiving input data of an authentication credential of the individual; and a web terminal configured to send an immunization status request, the immunization status request including the input data. The system further includes a vault computing device configured to receive the immunization status request and generate and send an immunization record request including an insurance plan number or other record identification information corresponding to the individual, the insurance plan number determined using the input data. The system further includes an immunization record database server having access to an immunization record database, the immunization record database server configured to retrieve immunization record data from the immunization record database using the insurance plan number and send the immunization record data to the vault computing device. The vault computing device is further configured to generate immunization status data representing the immunization status of the individual from the immunization record data and send the immunization status data to the in-person verification device. The in-person verification device is further configured to receive the immunization status data via the web terminal and display the immunization status data in a user interface.

The input device may be a camera and the input data may be a barcode image of a health card of the individual, and the vault computing device may decode the barcode image to obtain the insurance plan number.

The input device may be a camera and the input data may be a barcode image of a non-health card identification card of the individual, and the vault computing device may store a mapping of data encoded in the barcode image to the insurance plan number.

The input device may be a keypad and the input data may be a login and password, and the vault computing device may store a mapping of the login and password to the insurance plan number.

The input device may be a camera and the input data may be an image of a QR code, and the vault computing device may decode the QR code and obtain the insurance plan number using the decoded QR code.

The input device may be a biometric measurement device for receiving a biometric input. The input device may be fingerprint scan, a facial recognition scan, an iris scan, or other biometric measurement to uniquely or partially identify an individual.

The input device may use the identification of a first person to access the record of a second person. An example of this may be using the recognition of the credentials or biometrics of a parent provided via the input device to verify the credentials of their child.

A system for remote verification of an immunization status of an individual is provided. The system includes: a remote verification device including a web terminal configured to send an immunization status request, the immunization status request including contact data for the individual; a vault computing device configured to send an access approval request to the individual using the contact data; and an authorizer user device including a client access terminal configured to receive the access approval request and send a response including an access approval and an insurance plan number or other personal identification number. The vault computing device is further configured to send an immunization record request including the insurance plan number. The system further includes an immunization record database server having access to an immunization record database, the immunization record database server configured to retrieve immunization record data from the immunization record database using the insurance plan number and send the immunization record data to the vault computing device. The vault computing device is further configured to generate immunization status data representing the immunization status of the individual from the immunization record data and send the immunization status data to the remote verification device.

The immunization status request may specify a plurality of individuals and contact data for each individual, and the vault computing device may be configured to send access approval requests to each of the plurality of individuals, request the immunization record data for each of the plurality of individuals, generate the immunization status data for each of the plurality of individuals, and send the immunization status data for each of the plurality of individuals as a batch to the remote verification device.

The immunization status data may include a status validity period. The validity period may be different for each data element in the immunization record data. For example, a particular immunization may be valid for a first period (e.g. one year), whereas another type of immunization may be valid for a second period (e.g. two years). The validity period may be stored in the individual record. The immunization type may be encoded with a unique identifier and the date at which the immunization event occurred may also be encoded in the individual record per immunization event. This may permit adjustment of the validity period based on policy decisions by an authority, for example if new data show that an immunization is effective for a longer period than originally thought. Encoding the individual records in this manner may also allow for tracking of immunizations that require multiple immunization events to be effective, and to warn if those multiple immunization events have not occurred. Such tracking and warning may be performed by the vault computing device.

In addition to the effective tracking advantages discussed above, the system (e.g. the vault computing device, such as vault 304, 1504 described herein) may also track a unique serial and/or batch number per injection event. This may permit events like bad or ineffective vaccine batches to be tracked. The immunization serial number and/or batch number may be compared to a known good or known bad list of immunization serial/batch numbers. The immunization serial number and/or batch number may be determined from the immunization record data and the known good or bad list of immunization serial/batch numbers stored at or otherwise accessible to the vault computing device for performing the comparison. The immunization status may be adjusted to reflect this discovered bad batch. These serial/batch identifiers may not be a binary list of catastrophically good and bad batches, but may have multiple warning levels based on data gathered from the health and vaccine effectiveness in the field from other individuals who have had vaccines from a similar batch. For example, if a population that has been inoculated with a specific batch of vaccine shows vulnerability to a disease or disease variant, that warning level can be communicated to both the individual and the immunization status requestor.

A computing device for offline in-person verification of an immunization status of an individual is provided. The device includes: a camera for acquiring an image of encoded immunization status data, the encoded immunization status being an encoded representation of immunization status representing an immunization status of the individual; a processor executing an access application configured to receive the image as input and decode the encoded immunization status data to obtain the immunization status data; and a display device for displaying the immunization status data.

The immunization status data may include a status validity period.

The encoded immunization status data may be a QR code. The QR code is a method of encoding data for extraction of information by a camera system coupled to QR code software. The QR code is a currently popular method of encoding moderate amounts of data for easy extraction of information by the camera system and QR code software. In embodiments, other encoding systems may be used to similarly encode data in a visual format, for example linear barcode, 2D barcode, color codes, and images with embedded vectors or pixels with encoded data.

For convenience, since the QR code references a permission to access a record, the QR code may be displayed on a computer or handheld device like a mobile phone. The record may also be printed on paper. The display of the QR code may be associated with a coupled personal verification. The coupled personal verification may be a picture of the individual or biometric data. The biometric data may be a fingerprint, an iris scan, or automated facial recognition data. The association with personal biometric information may prevent an individual from using the permission credentials of another person, as the coupled personal verification would not match. Various forms of well-known coding and cross-coupling (cross checking) both the coupled personal verification data and the QR code data, such as watermarking, hidden verification codes, checksums, and valid image metrics may be used by the system to further protect from fraudulent use of others' credentials. These methods can be used independent of whether the image and QR code is displayed on an intelligent device or printed on paper.

A system for enabling an offline in-person verification of an immunization status of an individual is provided. The system includes: an authorizer user device including a client access terminal configured to send a request for encoded immunization status data of the individual; a vault computing device configured to send an immunization record request including an insurance plan number associated with the individual; and an immunization record database server having access to an immunization record database, the immunization record database server configured to retrieve immunization record data from the immunization record database using the insurance plan number and send the immunization record data to the vault computing device. The vault computing device is further configured to generate the encoded immunization status data from the immunization record data, the encoded immunization status data decodable to obtain immunization status data representing the immunization status of the individual, and send the encoded immunization status data to the authorizer user device.

The encoded immunization status data is decodable by an in-person verification device running an access application for decoding encoded immunization status data to obtain the immunization status data. If the in-person verification device is connected to a network, the device may use the permission previously granted by the individual to access the current individual's records. In the condition that the network is not available, a standalone device can be used to verify that the printed or displayed record is valid without a need for the in-person verification device to be connected to a network.

The request may include the insurance plan number.

The immunization status data may include a status validity period.

The immunization status data may include specific dates at which immunization events occurred.

The immunization status data may include serial number or batch data for the immunizations received.

The immunization record may include information regarding exemption classes or groups to which the individual belongs. For example, such information may indicate membership of the individual in a group that may be unable to receive a vaccine for a valid reason (e.g. allergy).

The immunization record may include the age of the individual.

The immunization record may include additional individual information for facilitating easy visual confirmation that the individual is the same individual represented by the immunization status data. The additional individual information may be, for example, any one or more of sex, gender, height, and eye color.

The encoded immunization status data may be a QR code or similar machine-readable code.

The encoded immunization status may be encoded in a Near Field Communications ("NFC") signal. The encoded immunization status may be encoded in a short range radio frequency ("RF") signal. The short range RF signal may be WiFi or Bluetooth. The encoded signals may be transmitted from the authorizer user device to the in-person verification device.

A computer system for secure data portability is provided. The system comprises a memory and a processor in communication with the memory. The processor is configured to: receive a data access request from a first web terminal associated with a first system user, the data access request for access to first data about a second system user, the data request including a first unique identifier corresponding to the second system user; confirm an access approval approving the first system user to access the first data, the access approval linked or mapped to the first unique identifier; send a request to a computing device connected to the computer system via a network connection, the request including a second data retrieval key, the second data retrieval key usable by the computing device to retrieve second data about the second system user from a database, the second data retrieval key provided to the computer system by the second system user via a second web terminal, the second data retrieval key linked or mapped to the access approval and the first unique identifier; receive the second data from the computing device and process the second data to generate the first data, the processing including stripping sensitive data from the second data so the sensitive data is not exposed to the first system user; and send the first data to the first web terminal.

In an embodiment, the computer system for secure data portability is configured to verify an immunization status of the second system user, the first system user is a verifier party, the second system user is an authorizer user, the data access request is an immunization status request, the first data is immunization status data of the authorizer user, the computing device is an immunization record database server, the second data retrieval key is an insurance plan number, the second data is immunization record data of the authorizer user, and the sensitive data is at least a subset of the immunization record data.

The access approval may be preexisting and stored in the memory.

The access approval may be rescinded by the authorized user.

The status of stored access approvals may be monitored by the authorized user and adjusted. This may be done through the authorizer user device in communication with the vault computing device.

The processor may be further configured to confirm the access approval by sending a request for the access approval and the second data retrieval key to the second web terminal, receiving a response from the second web terminal including the access approval and the second data retrieval key, and generating the link or map between the access approval, the second data retrieval key, and the first unique identifier.

Other aspects and features will become apparent, to those ordinarily skilled in the art, upon review of the following description of some exemplary embodiments.

BRIEF DESCRIPTION OF THE DRAWINGS

The drawings included herewith are for illustrating various examples of articles, methods, and apparatuses of the present specification. In the drawings:

FIG. 6 shows example database elements which are recorded and stored in the immunization record database of FIG. 3, according to an embodiment;

DETAILED DESCRIPTION

Figure 1:
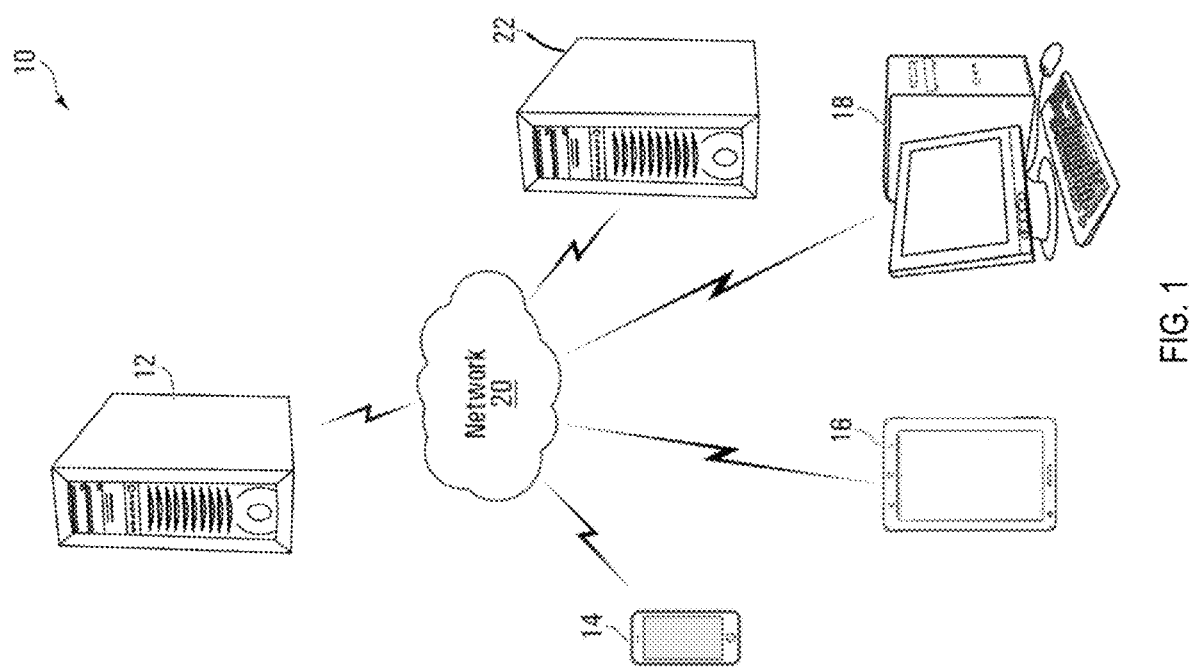
FIG. 1 is a schematic diagram of a system for verifying an immunization status of an individual, according to an embodiment.

Various apparatuses or processes will be described below to provide an example of each claimed embodiment. No embodiment described below limits any claimed embodiment and any claimed embodiment may cover processes or apparatuses that differ from those described below. The claimed embodiments are not limited to apparatuses or processes having all of the features of any one apparatus or process described below or to features common to multiple or all of the apparatuses described below.

One or more systems described herein may be implemented in computer programs executing on programmable computers, each comprising at least one processor, a data storage system (including volatile and non-volatile memory and/or storage elements), at least one input device, and at least one output device. For example, and without limitation, the programmable computer may be a programmable logic unit, a mainframe computer, server, and personal computer, cloud-based program or system, laptop, personal data assistance, cellular telephone, smartphone, or tablet device.

Each program is preferably implemented in a high-level procedural or object-oriented programming and/or scripting language to communicate with a computer system. However, the programs can be implemented in assembly or machine language, if desired. In any case, the language may be a compiled or interpreted language. Each such computer program is preferably stored on a storage media or a device readable by a general or special purpose programmable computer for configuring and operating the computer when the storage media or device is read by the computer to perform the procedures described herein.

A description of an embodiment with several components in communication with each other does not imply that all such components are required. On the contrary, a variety of optional components are described to illustrate the wide variety of possible embodiments of the present disclosure.

Further, although process steps, method steps, algorithms or the like may be described (in the disclosure and/or in the claims) in a sequential order, such processes, methods and algorithms may be configured to work in alternate orders. In other words, any sequence or order of steps that may be described does not necessarily indicate a requirement that the steps be performed in that order. The steps of processes described herein may be performed in any order that is practical. Further, some steps may be performed simultaneously.

When a single device or article is described herein, it will be readily apparent that more than one device/article (whether or not they cooperate) may be used in place of a single device/article. Similarly, where more than one device or article is described herein (whether or not they cooperate), it will be readily apparent that a single device/article may be used in place of the more than one device or article.

The systems and methods described herein have physical existence and/or manifest a discernable physical effect or change. The systems and methods described herein relate to the manual or productive arts, meaning those arts involving or concerned with applied and industrial sciences. The computer systems described herein have a material effect on the working of the invention and cooperate with other elements of the claimed invention.

Where the computer systems herein are programmed to run an algorithm, the computer processes the algorithm in a novel manner and the processing of the algorithm on the computer solves problems in the functioning of the computer. The computer and the algorithm form part of a single actual invention that solves a problem related to the manual or productive arts. Running the algorithms described herein on the computer improves the functioning of the computer, and the computer and the algorithm together form a single actual invention that solves a problem related to the manual or productive arts.

The following relates generally to confirming an immunization status of an individual, and more particularly to confirming an immunization status of an individual in in-person and remote scenarios.

The following also relates generally to secure data portability and data access sharing, and more particularly to systems and methods for enabling secure remote data portability by provisioning access to a first user to data (e.g. sensitive data) about a second user in a networked system in a secure and controlled manner and where the permission to access is granted by the second user.

While the present disclosure is directed to the verification of an immunization status, and authorization of access to user medical information for verification of the immunization status, it is to be understood that this is an example context in which the systems and methods can be used. Other applications are contemplated, such as for the verification of a test result for an infection (e.g. viral test, such as a Covid test). The systems and methods of the present disclosure may be used more generally for the processing and sharing of medical data. The systems and methods of the present disclosure may also be used in non-medical applications for the sharing and processing of sensitive data, such as in the field of financial technology (e.g. electronic value transactions).

The embodiments of the systems, methods, and devices described herein refer to the use of an "insurance plan identifier". It is to be understood that the insurance plan number is one example of a unique personal identifier or personal credential and that, in other embodiments, similar systems, methods, and devices may be implemented using another form of personal identifier number or personal credential. Such other embodiments are contemplated within the scope of the present disclosure.

The embodiments of the systems, method, and devices described herein refer to the use of a QR code. It is to be understood that a QR code is one example of how encoded representations of data may be implemented. Other encoding systems are contemplated. For example, other encoding systems may be used to similarly encode data in a visual format. Such other encoding systems may use a linear barcode, 2D barcode, colour codes, or images with embedded vectors or pixels with encoded data. Generally, information is extracted from the encoded data by a camera system coupled to software for decoding the encoded data imaged by the camera (e.g. QR code software).

The embodiments of the systems, methods, and devices described herein refer to the presentation of a personal credential to an in-person verification device. The presentation may be performed at a point of entry. The personal credential may be a health card, an alternate identification card, a login password, or a QR code (or other form of encoded data). It is to be understood that, in variations of the present disclosure, the personal credential may act as an authentication credential, an authorization credential (authorizing access to their status, or both. For example, in the case of an in-person verification scenario where a health card is presented to an in-person verification terminal, the health card is a person credential that may act as both an authentication credential and an authorization credential.

Referring now to FIG. 1, shown therein is a system 10 for verifying an immunization status of an individual, according to an embodiment.

The system 10 may be used for in-person or remote verification of an immunization status. The system 10 may be used for online or offline immunization status verification.

The system 10 includes a server platform 12 which communicates with a plurality of authorizer user devices 14, a plurality of in-person verification devices 16, and a plurality of remote verification devices 18 via a network 20. The in-person verification devices 16 and remote verification devices 18 may be generically referred to as "verification devices". The server platform 12 also communicates with a plurality of immunization or medical record database server devices 22.

The server platform 12 may be a purpose-built machine designed specifically for provisioning requesting parties (an in-person verifier or remote verifier) with access to an immunization status of an individual (authorized user), where such access is authorized by the individual. The server platform 12 may determine the immunization status from an immunization or other medical record received from the immunization record database server 22 and provide the immunization status to the in-person or remote verification device 16, 18. The server platform 12 provides secure access to immunization status data, where each access is authorized by the health card holder only (i.e. authorizer user) and the server platform 12 stores an access permission mapping. The server platform 12 may perform tracking or warning functions. Tracking may relate to tracking of immunization serial or batch numbers. Such numbers may be included in the immunization record data received from a immunization record database server 22. Tracking may include determining when an immunization is from a particular batch (e.g. good or bad) and notifying one or more users of the system that a particular immunization credential has a potential batch-related issue. Notification may be through adjusting the immunization status of the authorizer user accordingly. Warning may include the aforementioned notifying of users related to tracking or may include notifying system users (authorizer users or verifier parties) when a particular status is facing an upcoming state change. Notifying may include determining that a criteria is met to generate the warning, generating the warning, and sending the warning, such as via email or text message, to the appropriate system users.

The authorizer user device 14 allows an authorizer user to interact and communicate with other components of the system, such as the server platform 12 and the in-person verification device 16. The authorizer user is an individual user who wants to be able to provide their immunization status to a verifier user (such as an in-person verifier user or a remote verifier user) for verification using the system 10. In some cases, the in-person presentation of a personal credential, such as a QR code on a portable device or a health card, may constitute permission for providing immunization status to a verified user. The authorizer user device 14 may be used by the authorizer user to register an authorization credential at the server platform 12. The authorizer user device 14 may be used by the authorizer user to authorize a verifier user, such as a remote verifier user, to access (i.e. be provided with by the server platform 12) an immunization status of the authorizer user. The authorization may be one-time or persistent/ongoing. For persistent/ongoing authorization, the authorization to access (access approval) may be for a specified duration or at a specified interval (e.g. daily). The authorizer user device 14 may be used by an authorizer user to present encoded data, such as a QR code, to the in-person verification device 16. The encoded data may represent an immunization status of the authorizer user or an encoded authentication credential. For example, the authorizer user device 14 may be configured to receive and display a QR code for reading by a QR reader operating at an in-person verification device 16. The authorization may be for an entire record such as a record of immunization status. The authorization may be for a more specific inquiry, such as where the last vaccination took place, or the brand of vaccine. For larger, more complex databases the permissions can be more complex, permitting either access to the original data, or permission to access the results of calculations made on specific elements within the database. To manage complexity, these permissions may be grouped into more easily understandable permissions. Examples include 'allow inquiry for Valid vaccine according to Ontario Government Recommendations', or 'allow inquiry for date of last vaccine'. Databases other than vaccine databases can also be used by this permission granting system to yield information on enquiries regarding financial, personal, academic, or other information.

The in-person verification device 16 is configured to verify an immunization status of an individual (authorizer user) in scenarios where the authorizer user is present, such as at a point-of-entry. The in-person verification device 16 receives an authorization credential from the authorizer user (e.g. health card, alternate ID, login/password, QR code) and requests an immunization status for the authorizer user from the server platform 12. The authorization (permission to access status) may be temporary (e.g. one time access) or may be for any length of time. The in-person verification device 16 receives the immunization status from the server platform 12. The in-person verification device 16 outputs the immunization status to the verifier user, such as via a display. The in-person verification device 16 may be a device operated by an in-person operator or may take the form of an automated entry system, like an unmanned turnstile.

The remote verification device 18 is configured to verify an immunization status of an individual (authorizer user) in scenarios where the authorizer user is not present to provide the authorization credential to the remote verifier user. Generally, in the remote scenario the authorizer user is in a structured relationship with the verifier party. The "structured relationship" in this sense refers to the fact that the verifier party holds data about the authorizer user. Examples include employer-employee, educational institution-student, airline-passenger, etc. In many cases, the remote scenario is particularly suitable to structured relationships in which the verifier party needs to verify the immunization status of many individuals. Remote verification may be particularly advantageous in situations where in-person verification of the immunization status of a large number of people is impractical.

The immunization record database server 22 stores or is otherwise in communication with and has access to a database of immunization records (or medical records). The immunization records may be stored in the database such that an immunization record (including one or more data elements) for an individual is retrievable from the database using a health insurance plan number (e.g. Ontario Health Insurance Plan or "OHIP" number) for the individual or other number unique to the individual. The health insurance plan number may also be referred to herein as a "health card number" and appear on or be otherwise determinable from a physical health card. In other embodiments, a personal identification number other than an insurance plan number may be used.

The server platform 12, authorizer user devices 14, in-person verification devices 16, remote verification devices 18 and immunization record database server devices 22 may be a server computer, desktop computer, notebook computer, tablet, PDA, smartphone, or another computing device. The devices 12, 14, 16, 18, 22 may include a connection with the network 20 such as a wired or wireless connection to the Internet. In some cases, the network 20 may include other types of computer or telecommunication networks. The devices 12, 14, 16, 18, 22 may include one or more of a memory, a secondary storage device, a processor, an input device, a display device, and an output device. Memory may include random access memory (RAM) or similar types of memory. Also, memory may store one or more applications for execution by processor. Applications may correspond with software modules comprising computer executable instructions to perform processing for the functions described below. Secondary storage device may include a hard disk drive, floppy disk drive, CD drive, DVD drive, Blu-ray drive, or other types of non-volatile data storage. Processor may execute applications, computer readable instructions or programs. The applications, computer readable instructions or programs may be stored in memory or in secondary storage or may be received from the Internet or other network 20. Input device may include any device for entering information into device 12, 14, 16, 18, 22. For example, input device may be a keyboard, keypad, cursor-control device, touchscreen, camera, or microphone. Display device may include any type of device for presenting visual information. For example, display device may be a computer monitor, a flat-screen display, a projector or a display panel. Output device may include any type of device for presenting a hard copy of information, such as a printer for example. Output device may also include other types of output devices such as speakers, for example. In some cases, device 12, 14, 16, 18, 22 may include multiple of any one or more of processors, applications, software modules, second storage devices, network connections, input devices, output devices, and display devices.

Although devices 12, 14, 16, 18, 22 are described with various components, one skilled in the art will appreciate that the devices 12, 14, 16, 18, 22 may in some cases contain fewer, additional or different components. In addition, although aspects of an implementation of the devices 12, 14, 16, 18, 22 may be described as being stored in memory, one skilled in the art will appreciate that these aspects can also be stored on or read from other types of computer program products or computer-readable media, such as secondary storage devices, including hard disks, floppy disks, CDs, or DVDs; a carrier wave from the Internet or other network; or other forms of RAM or ROM. The computer-readable media may include instructions for controlling the devices 12, 14, 16, 18, 22 and/or processor to perform a particular method.

In the description that follows, devices such as server platform 12, authorizer user devices 14, in-person verification devices 16, remote verification devices 18, and immunization record database server devices 22 are described performing certain acts. It will be appreciated that any one or more of these devices may perform an act automatically or in response to an interaction by a user of that device. That is, the user of the device may manipulate one or more input devices (e.g. a touchscreen, a mouse, or a button) causing the device to perform the described act. In many cases, this aspect may not be described below, but it will be understood.

As an example, it is described below that the devices 12, 14, 16, 18, 22 may send information to the server platform 12. For example, an authorizer user using the authorizer user device 14 may manipulate one or more input devices (e.g. a mouse and a keyboard) to interact with a user interface displayed on a display of the authorizer user device 14. Generally, the device may receive a user interface from the network 20 (e.g. in the form of a webpage). Alternatively, or in addition, a user interface may be stored locally at a device (e.g. a cache of a webpage or a mobile application).

Server platform 12 may be configured to receive a plurality of information, from each of the plurality of authorizer user devices 14, in-person verification devices 16, remote verification devices 18, and immunization record database server devices 22. Generally, the information may comprise at least an identifier identifying the authorizer user, in-person verifier user, remote verifier user, or immunization record database server user. For example, the information may comprise one or more of a username, e-mail address, password, or social media handle.

In response to receiving information, the server platform 12 may store the information in storage database. The storage may correspond with secondary storage of the device 12, 14, 16, 18, 22. Generally, the storage database may be any suitable storage device such as a hard disk drive, a solid state drive, a memory card, or a disk (e.g. CD, DVD, or Blu-ray etc.). Also, the storage database may be locally connected with server platform 12. In some cases, storage database may be located remotely from server platform 12 and accessible to server platform 12 across a network for example. In some cases, storage database may comprise one or more storage devices located at a networked cloud storage provider.

The authorizer user device 14 may be associated with an authorizer user account. Similarly, the in-person verification device 16 may be associated with an in-person verifier account, the remote verification device 18 may be associated with a remote verifier account, and the immunization record database server device 22 may be associated with an immunization record database account. Any suitable mechanism for associating a device with an account is expressly contemplated. In some cases, a device may be associated with an account by sending credentials (e.g. a cookie, login, or password etc.) to the server platform 12. The server platform 12 may verify the credentials (e.g. determine that the received password matches a password associated with the account). If a device is associated with an account, the server platform 12 may consider further acts by that device to be associated with that account.

Figure 2:
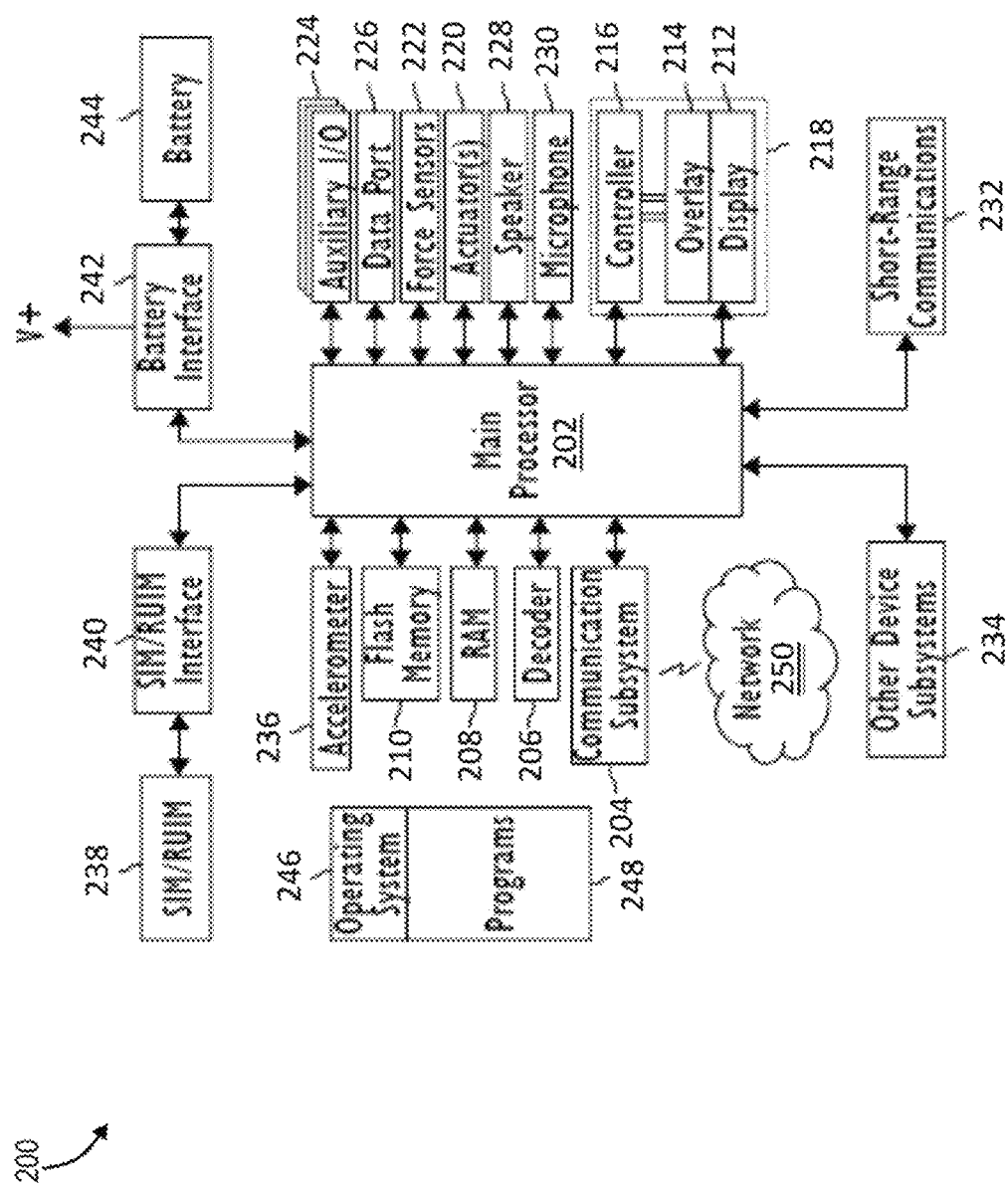
FIG. 2 is a block diagram of a computing device of FIG. 1, according to an embodiment.

Referring now to FIG. 2, shown therein is a block diagram of a computing device 200 of the system 10 of FIG. 1, according to an embodiment. The computing device 200 may be, for example, any one of devices 12, 14, 16, 18, 22 of FIG. 1.

The computing device 200 includes multiple components such as a processor 202 that controls the operations of the computing device 200. Communication functions, including data communications, voice communications, or both may be performed through a communication subsystem 204. Data received by the computing device 200 may be decompressed and decrypted by a decoder 206. The communication subsystem 204 may receive messages from and send messages to a wireless network 250.

The wireless network 250 may be any type of wireless network, including, but not limited to, data-centric wireless networks, voice-centric wireless networks, and dual-mode networks that support both voice and data communications.

The computing device 200 may be a battery-powered device and as shown includes a battery interface 242 for receiving one or more rechargeable batteries 244.

The processor 202 also interacts with additional subsystems such as a Random Access Memory (RAM) 208, a flash memory 210, a display 212 (e.g. with a touch-sensitive overlay 214 connected to an electronic controller 216 that together comprise a touch-sensitive display 218), an actuator assembly 220, one or more optional force sensors 222, an auxiliary input/output (I/O) subsystem 224, a data port 226, a speaker 228, a microphone 230, short-range communications systems 232 and other device subsystems 234.

In some embodiments, user-interaction with the graphical user interface may be performed through the touch-sensitive overlay 214. The processor 202 may interact with the touch-sensitive overlay 214 via the electronic controller 216. Information, such as text, characters, symbols, images, icons, and other items that may be displayed or rendered on a computing device generated by the processor 202 may be displayed on the touch-sensitive display 218.

The processor 202 may also interact with an accelerometer 236 as shown in FIG. 2. The accelerometer 236 may be utilized for detecting direction of gravitational forces or gravity-induced reaction forces.

To identify a subscriber for network access according to the present embodiment, the computing device 200 may use a Subscriber Identity Module or a Removable User Identity Module (SIM/RUIM) card 238 inserted into a SIM/RUIM interface 240 for communication with a network (such as the wireless network 250). Alternatively, user identification information may be programmed into the flash memory 210 or performed using other techniques.

The computing device 200 also includes an operating system 246 and software components 248 that are executed by the processor 202 and which may be stored in a persistent data storage device such as the flash memory 210. Additional applications may be loaded onto the computing device 200 through the wireless network 250, the auxiliary I/O subsystem 224, the data port 226, the short-range communications subsystem 232, or any other suitable device subsystem 234.

In use, a received signal such as a text message, an e-mail message, web page download, or other data may be processed by the communication subsystem 204 and input to the processor 202. The processor 202 then processes the received signal for output to the display 212 or alternatively to the auxiliary I/O subsystem 224. A subscriber may also compose data items, such as e-mail messages, for example, which may be transmitted over the wireless network 250 through the communication subsystem 204.

For voice communications, the overall operation of the computing device 200 may be similar. The speaker 228 may output audible information converted from electrical signals, and the microphone 230 may convert audible information into electrical signals for processing.

Figure 3:
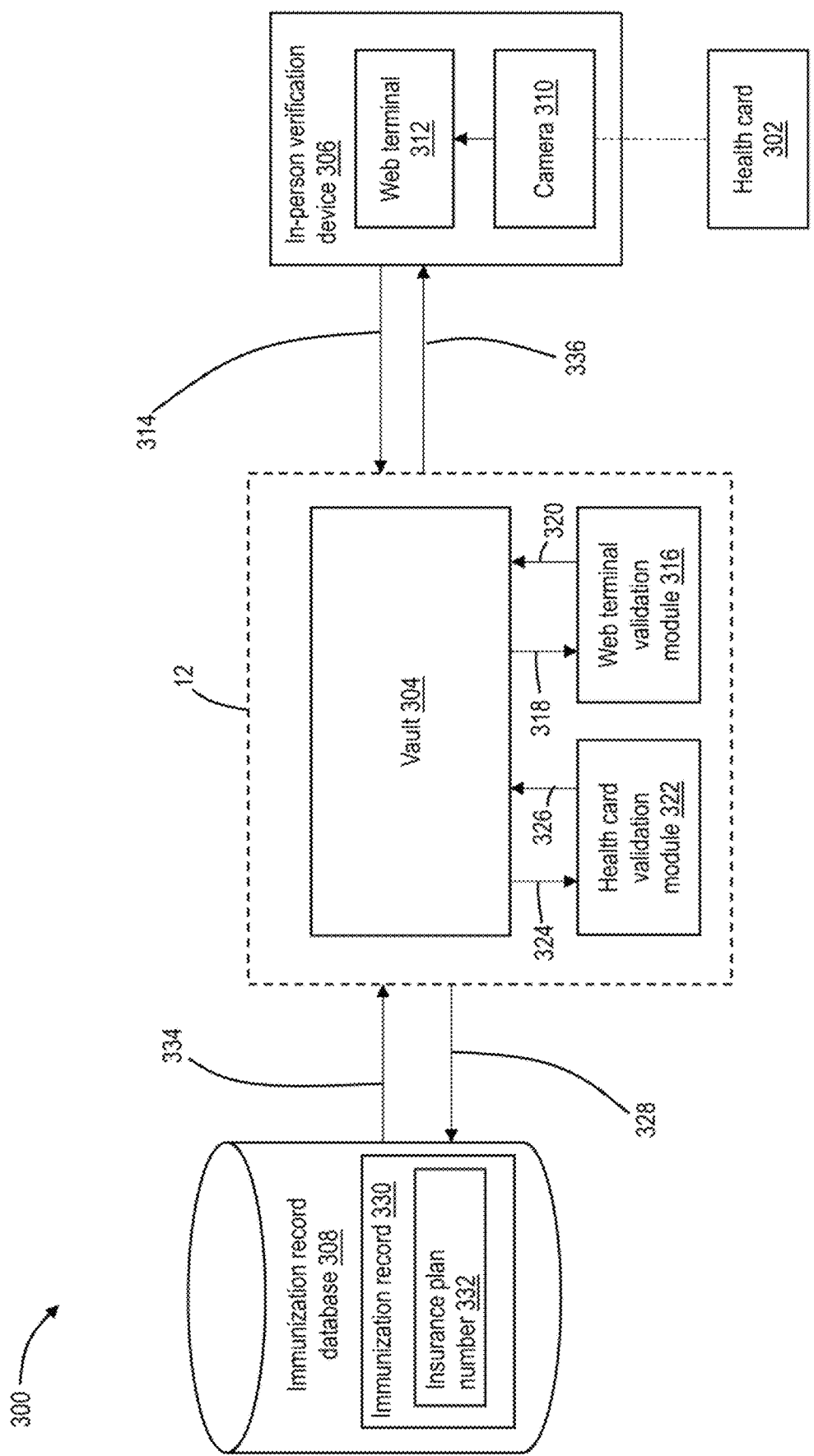
FIG. 3 is a block diagram of a system for in-person verification of an immunization status using a health card, according to an embodiment.

Referring now to FIG. 3, shown therein is a computer system 300 for in-person verification of an immunization status using a health card, according to an embodiment.

The system 300 uses a health card 302. The health card 302 is generally a card issued to an insured individual by their insurance provider (e.g. government insurer, private insurer) and which includes certain information about the cardholder.

The health card 302 is presented by an individual (authorizer user) who wants their immunization status to be verified for the benefit of an in-person verifier user. The presentation of the health card 302 by the authorizer user may happen at a point-of-service or point-of-access or point-of-entry. Note that scenarios are contemplated in which the health card 302 of the authorizer user (cardholder) is presented by someone who is not the authorizer user, such as in the case of a parent presenting the health card 302 of their child. As such, throughout the present disclosure references to the authorizer user performing certain actions are intended to include scenarios in which another individual is performing such actions on behalf of the authorizer user who is the individual for which an immunization status is being verified.

The health card 302 may be, for example a provincial health card such as an OHIP card or the like.

The health card 302 includes a machine-readable barcode (not shown). The barcode may be a two-dimensional (2D) barcode. The barcode encodes data related to the health card 302, and more particularly data related to the cardholder (authorizer user). In other embodiments, the health card 302 may include other machine-readable features for encoding data about the cardholder which may be used by the system 300 in addition to or instead of the barcode. For example, the health card 302 may include a machine-readable magnetic stripe. In cases where the system 300 uses a machine-readable feature of the health card 302, it is to be understood that the in-person verification device (described below) is adapted to include the necessary hardware and/or software to read the feature.

The data encoded by the barcode may be decoded to obtain a unique identifier of the cardholder, such as an insurance plan number (or "health card number"). In the case of an OHIP card, the data encoded by the barcode may be decoded to obtain an OHIP number.

Figure 4:
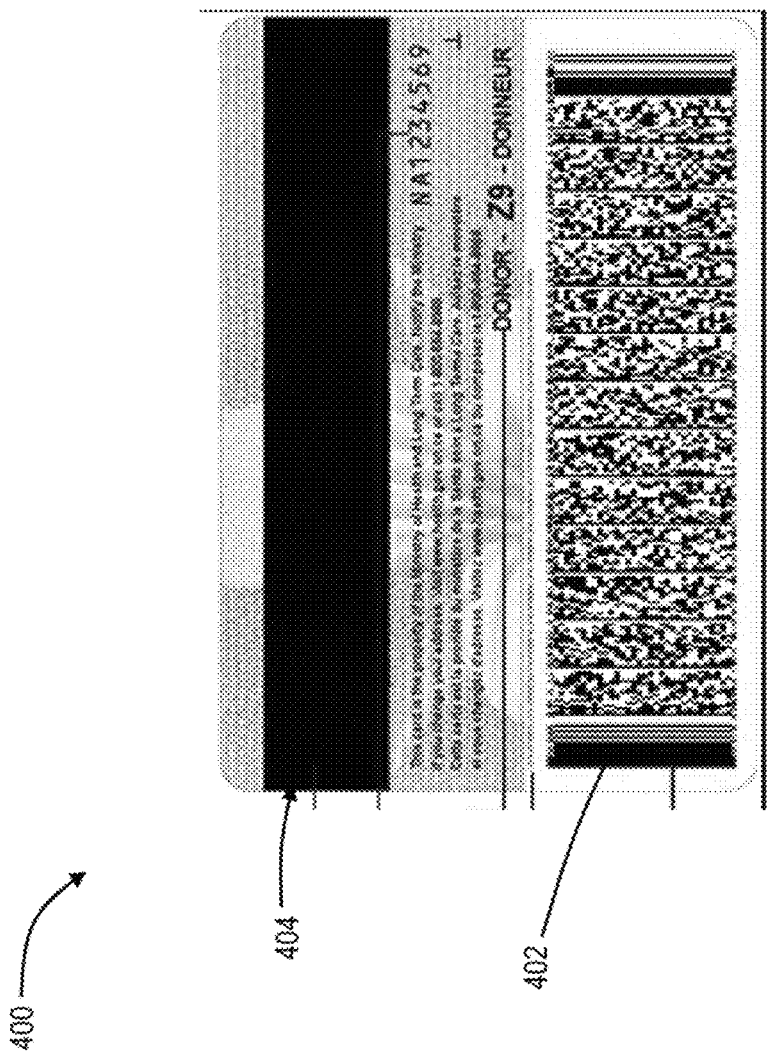
FIG. 4 is a view of a backside of an example health card that may be used as the health card in the system of FIG. 3, showing various features of the health card that may be used by the system, according to an embodiment.

FIG. 4 shows an example 400 of health card 302, according to an embodiment. The example 400 is an OHIP card. The card 400 includes a machine-readable 2D barcode 402. The card also includes a magnetic stripe 404 which may, in some embodiments of the system 300, be used by the system 300 as a machine readable feature of the card 400.

The system 300 includes a vault computing device 304 (or vault 304), an in-person verification device 306, and an immunization record database 308. The vault 304 may be the server platform 12 of FIG. 1. The in-person verification device 306 may be the verification device 16 of FIG. 1. The immunization record database 308 may be located at or otherwise accessible to the database server 22 of FIG. 1.

The vault 304 communicates, including sending and receiving data (request and response), with the in-person verification device 306 via a network connection. The vault 304 also communicates, including sending and receiving data, with the immunization record database 308 via a network connection. In some cases, the vault 304 may communicate with the database 308 through a database server, such as the database server 22 of FIG. 1.

The in-person verification device 306 includes a camera 310. The camera 310 may be an existing camera that is part of the hardware of a standard mobile computing device, such as a smartphone or tablet, configured to operate as the in-person verification device 306.

The health card 302 is presented and the camera 310 of the in-person verification device 306 acquires an image of the barcode on the health card 302 ("barcode image").

The in-person verification device 306 also includes a web terminal 312. The web terminal 312 facilitates communication with the vault 304, including sending requests to and receiving responses from the vault 304. The web terminal 312 may use a web browser for communicating with the vault 304. The web terminal 312 includes a user interface for inputting data to send to the vault 304 and for displaying data received from the vault 304, such as an immunization status, in a human-readable format. The user interface may run in the web browser. The in-person verification device 306 includes a display (not shown) for displaying the user interface.

The web terminal 312 sends an immunization status request at 314 to the vault 304. The request 314 includes the barcode image and a web terminal identifier ("terminal ID") of the web terminal 312.

In some cases, request 314 may include additional data which can be used by the vault 304 to identify a particular set of rules or criteria (mask) in determining the immunization status. The additional data may specify an access point or address. The additional data may be selected by the user at the web terminal 312. The additional data may specify entry requirements or an access category. The vault 304 can obtain the additional data, identify the corresponding set of criteria or rules to apply (if any), and apply the set of criteria or rules to the immunization status determination. The additional data may explicitly define a rule set to be applied by the vault 304. The vault 304 may store a plurality of rule sets and apply the rule set specified in the additional data.

The vault 304 receives the immunization status request 314 and performs validation of the health card 302 and the web terminal 312.

The vault 304 includes a web terminal validation module 316. The web terminal validation module 316 is configured to validate the web terminal 312 (and thus, the in-person verification device 306) using the web terminal ID received via the immunization status request 314. The vault 304 provides the web terminal ID as input to the web terminal validation module 316 at 318. The web terminal validation module 316 generates a terminal validation output indicating whether or not the terminal 312 is valid and outputs the terminal validation output to the vault 304 at 320. If the terminal validation output indicates that the web terminal 312 is not valid, the vault 304 may send a response to the in-person verification device 306 indicating the web terminal ID is invalid.

The web terminal interface may allow for easy field deployment, as web browser functionality is ubiquitously available in a wide range of low-cost terminals that are widely deployed. Smartphones, tablets, or personal computers may be used for this function without downloading any application software. Further, the web terminal validation module 316 performs an additional check to ensure that the web terminal 312 is a valid user of the system. Health records, and information about health status, are private and personal, so ensuring that only validated users can access the system is advantageous. In an embodiment, the validation of web terminal devices may be done by creating a database of authorized users, which is stored by or otherwise accessible to the vault 304, and verifying a userID and login password to confirm that a particular terminal has authorized access. The vault 304 may be configured to maintain, update, and store a log file of all authorizer accesses. This log file may enable forensic analysis of suspected privacy breaches. In one embodiment, a business number or school ID is used as the username to enable access.

The vault 304 includes a health card validation module 322. The health card validation module 318 is configured to validate the health card 302 using the barcode image received at 314. The vault 304 provides the barcode image data as input to the health card validation module 322 at 324. The health card validation module 322 generates a health card validation output indicating whether the health card is valid or invalid and outputs the health card validation output to the vault 304 at 326. If the health card validation output indicates that the health card 302 is invalid, the vault 304 may send a response to the in-person verification device indicating the health card 302 is invalid.

The health card validation output includes an insurance plan number (e.g. OHIP number) linked to the health card 302. As such, the health card validation module 322 may be configured to decode the barcode in the barcode image to obtain the insurance plan number.

The health card validation module 322 may use a check digit technique or other algorithm for validating the health card 302. The health card validation module 322 may include external, third-party software components for validating health card data. In an embodiment, the health card validation module 322 may use a health card validation database (e.g. OHIP card validation database) similar to those used by doctors and healthcare service providers to complete billing.

In some embodiments, the vault 304 may include a separate barcode image decoder module (not shown) for decoding the barcode image and obtaining the insurance plan number 332. The insurance plan number 332 may be provided as input to the health card validation module 322, which determines whether the insurance plan number 332 is valid or invalid.

Validation using a health card may be advantageous in situations where a user has no mobile phone or other portable device to store a QR code (or other encoded data). Health cards are freely given as part of the universal health care system in Canada, and for example, everyone in Ontario has the right to a health card. In practice, the barcode from a health card can be photocopied and conveniently carried around if desired. The health card may have the added advantage of having a built in identity verification component (e.g. photograph, and encoded information from photograph), such as with OHIP cards. In practice, any unique identifier may be used as the key for accessing individual records. In addition to the advantage of identity verification, immunization record databases 308 may likely be organized with health ID as a primary identifier, thus providing another advantage to the use of the health card.

The vault 304 sends a request at 328 for an immunization record 330 to the immunization record database 308. The request 328 includes the validated insurance plan number.

The immunization record database 308 stores an immunization record 330. The immunization record 330 includes data elements describing an immunization event (or "immunization"), such as inoculation with a vaccine. In some cases, the immunization record 328 may be a subset of a larger medical record stored in the database 308. The immunization record 330 may include a plurality of immunization events. The immunization record 330 may be for a specific infectious disease (e.g. Covid-19) or may describe immunization events for a plurality of infectious diseases (e.g. Covid-19, tuberculosis, MMR).

In an example, the immunization record database 308 may be an Ontario Health Data Platform ("OHDP") database.

The immunization record 330 is stored in the immunization record database 308 such that the immunization record 330 is retrievable from the immunization record database 308 using the insurance plan number 332. For example, the database 308 may be configured such that the insurance plan number 332 is a primary key for the immunization record 330. In other embodiments, it can be understood that data other than an insurance plan number 332 may be used where the data functions as a primary key for the immunization record 330 in the database 308. For example, in other embodiments, the insurance plan number 332 may be a Personal Identity Number like those used in Sweden, a Blue Cross number, or similar. Such data may be encoded on the health card 302.

Figure 5:
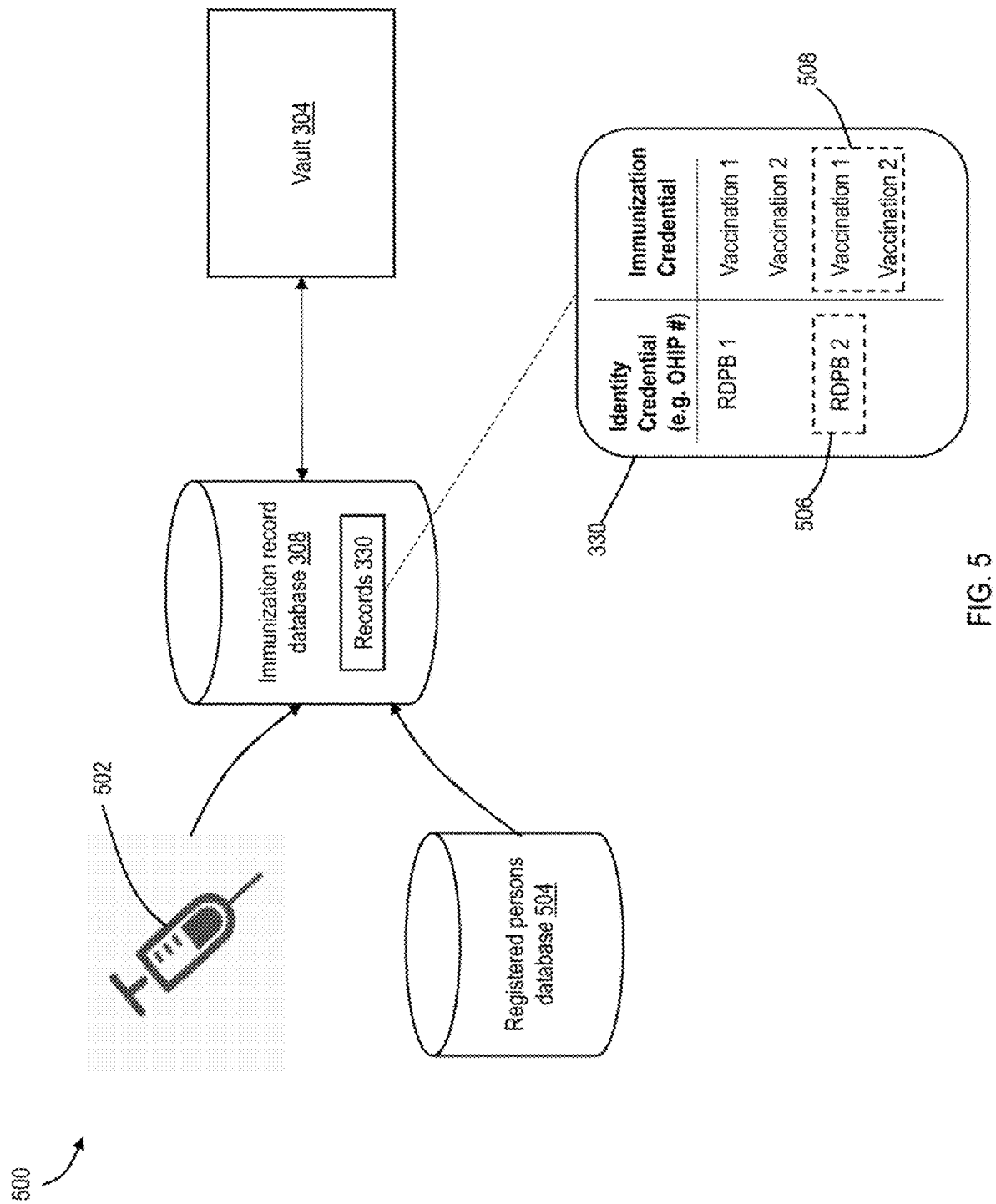
FIG. 5 is a block diagram of a data entry process at inoculation which populates the immunization record database of FIG. 3, according to an embodiment.

Referring now to FIG. 5, shown therein is an example data entry process 500 at inoculation which populates the immunization record database 308, according to an embodiment.

As illustrated, the immunization record database 308 is populated using inputs from a vaccination recordation system 502 and a registered persons database 504. In particular, data from the vaccination recordation system 502 and the registered persons database 504 is used to populate immunization records 330 stored in the immunization record database 308.

The vaccination recordation system 502 records immunization events. The vaccination recordation system 502 may record Covid vaccination data (i.e. Covid-related immunization events). In an example, the vaccination recordation system 502 may be COVaxON or the like. COVaxON is the provincial system for recording Covid vaccination in Ontario.

The registered persons database 504 stores information on persons registered under a particular insurance plan or provider. The stored data includes an identity credential, such as an insurance plan number 332 (or health card number), for a person in the database 504. In an example, the registered persons database 504 may be the Registered Persons Database (RPDB) in Ontario, which contains information on persons registered under the Ontario Health Insurance Plan (OHIP) and who are eligible for the Ontario Drug Program.

A record 330 includes an identity credential 506, such as an insurance plan number (e.g. OHIP number), and one or more immunization credentials 508 corresponding to the identity credential 506. Generally, the identity credential 506 represents an individual and the immunization credential 508 represents a credential for that individual that satisfies a criteria for immunization status verification. For example, the immunization credential 508 may represent or describe an immunization event (such as receiving a vaccination) or an exemption.

Referring now to FIG. 5, shown therein database elements 600 which are recorded and stored in the immunization record database 308, according to an embodiment.

The database elements 600 include a plurality of records 602. Each record 602 includes data values or elements for a health card number (insurance plan number) field 604, a procedure (immunization event) field 606, a date field 608, a batch/serial number field 610, and an exemption code field 612.

The procedure field 606 may contain data values specifying a specific vaccine (e.g. Covid vaccine) received and whether the specific vaccine is a first or second shot (or nth shot). The procedure field 606 may contain data values indicating a specific test performed (e.g. Covid test).

The exemption code field 610 may contain data values specifying there is no exemption code (e.g. "none") or specifying there is an exemption (and potentially the specific type of exemption).

The immunization record 330 that is requested by the vault 304 and verified may include a plurality of records 602 for the same individual (same identity credential 506). For example, if the immunization record request 328 from the vault 304 specifies the health card number "123456789", the immunization record 330 sent to the vault 304 may include a plurality of records 614 corresponding to the health card number "123456789". As such the database 308 may return all records 602 corresponding to the insurance plan number (or other database key) received from the vault 304.

Referring again to FIG. 3, the immunization record database 308 retrieves the immunization record 330 using the insurance plan identifier 332 and sends a response at 334 to the vault 304. The response includes the immunization record 330.

The vault 304 receives the response 334 and determines an immunization status using the immunization record 330. In an embodiment, the immunization status is a binary status indicator indicating a positive or negative immunization state (e.g. PASS/FAIL). In some embodiments, additional warning levels may be transmitted other than PASS/FAIL status. For example, the immunization status may include a warning that immunization validity is about to expire, or that there is a change in status regarding the permissions associated with a particular immunization event. Such warnings can also be used to trigger messages sent directly to the authorized verifier and/or the individual. For example, upon determining that the immunization status has an associated warning, the vault 304 may be configured to generate and send a message to the verifier party or the individual.

The vault 304 may include a policy engine (e.g. policy engine 1102 of FIG. 11) for determining the immunization status from the immunization record 330.

The vault 304 sends a response at 336 to the in-person verification device 306. The response 336 includes the immunization status. In some cases, the response 336 may include other data associated with the health card 302 or for authenticating the cardholder, such as image data corresponding to a photo of the individual. The image data may be retrieved from the immunization record database 308 using the verified insurance plan number 332 included in the immunization record request 328. In such cases, the request 328 may instruct the immunization record database 308 to include the image data in the response 334.

The in-person verification device 306 receives the immunization status response and the web terminal 312 displays the immunization status in the user interface. The immunization status may be displayed as text (e.g. "PASS", "FAIL"), a graphic (green icon, red icon, checkmark or "x"), or both.

The immunization status may be provided to the in-person verification device 306 as a status code (e.g. binary status code—pass/fail) and the in-person verification device 306 is configured to generate a visual representation of the status from the status code.

Further embodiments of systems for in-person immunization status verification will now be described with reference to FIGS. 7A, 7B, and 8. In these embodiments, components or processes having the same or similar functions to components or processes described in reference to FIG. 3 are given the same reference numbers (e.g. vault 304). It is to be understood that certain details regarding the functioning of such common components or processes that have been descried in reference to FIG. 3 may apply to commonly numbered components or processes but are not be repeated in describing FIGS. 7A, 7B, and 8. It is to be further understood that certain components, functions, or processes of in-person immunization status verification may be implemented in remote immunization status verification implementations described herein.

Figure 7A:
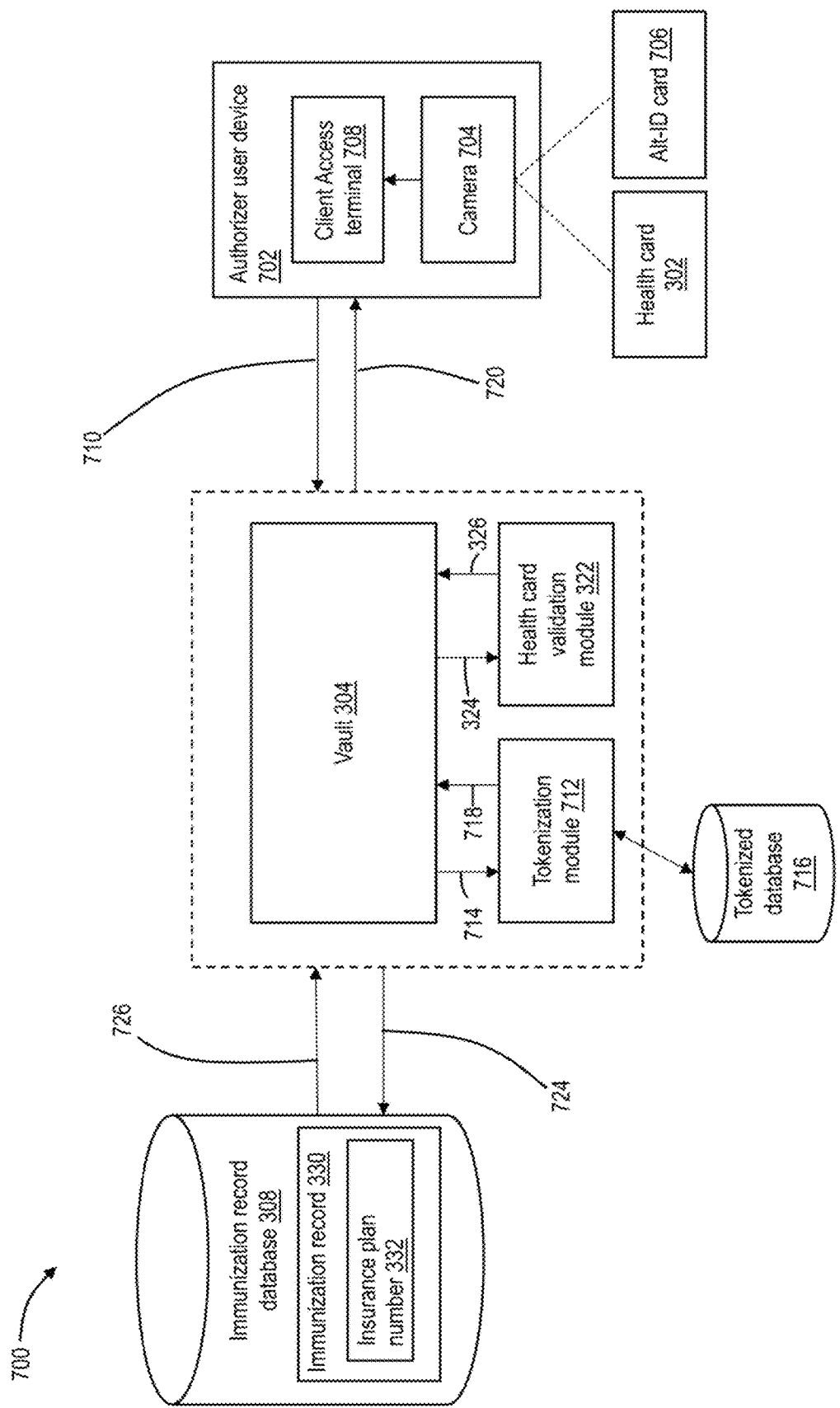
FIG. 7A is a block diagram of a system for in-person verification of an immunization status using a non-health card authentication credential, and in particular a health card and alternate authentication credential registration process performed by the system, according to an embodiment.
Figure 7B:
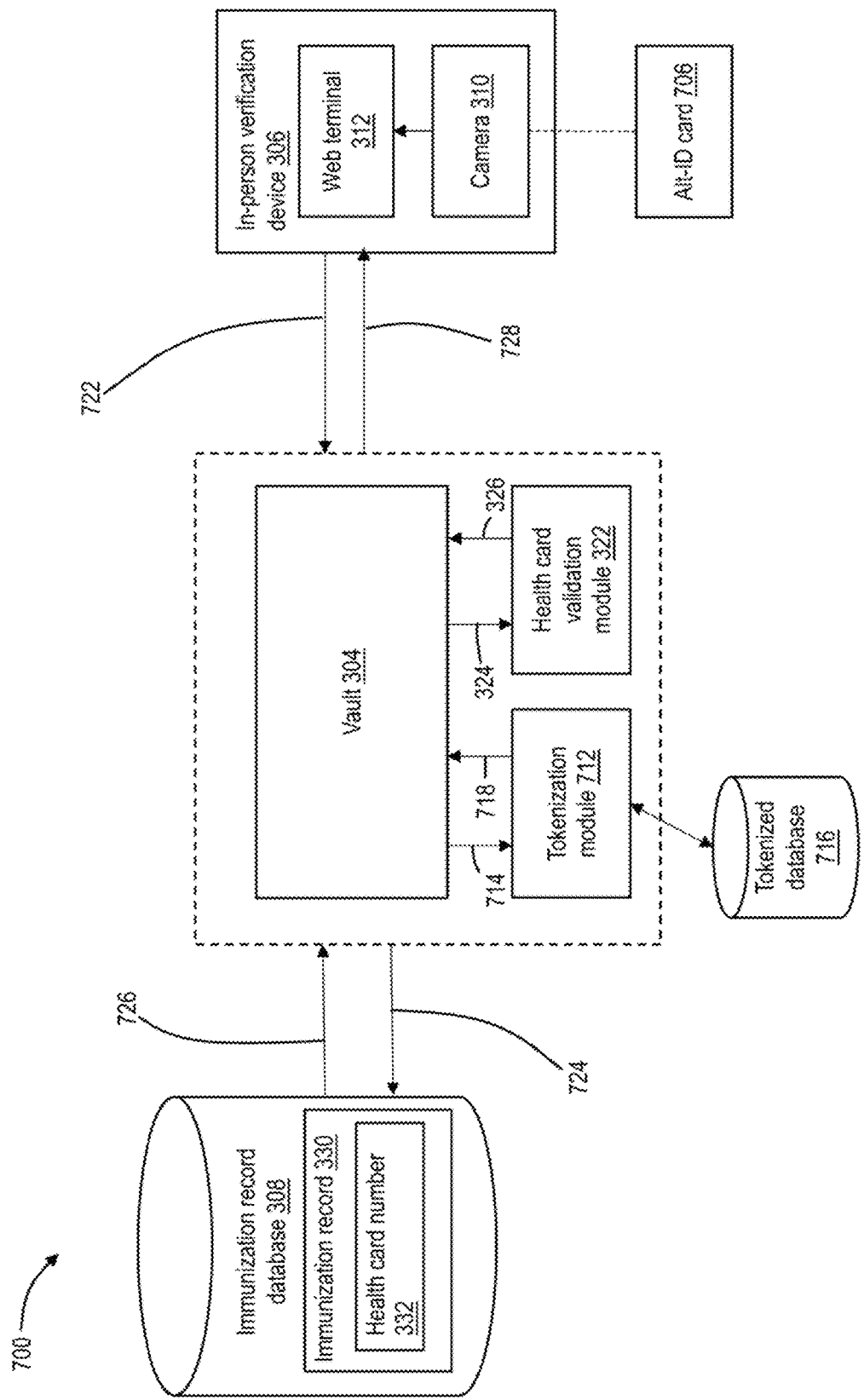
FIG. 7B is a block diagram of the system for in-person verification of an immunization status using a non-health card authentication credential of FIG. 7A, and in particular verification of an immunization status using the non-health card authentication credential registered in FIG. 7, according to an embodiment.

Referring now to FIGS. 7A and 7B, shown therein is a system 700 for in-person verification of an immunization status using a non-health card authentication credential, according to an embodiment. In particular, FIG. 7A illustrates a process for registering a health card and an alternate (non-health card) authorization credential linked to the health card. FIG. 7B illustrates an in-person immunization status verification process using the alternate authorization credential linked to the health card registered in FIG. 6A.

Referring now to FIG. 7A, the system 700 includes a vault 304, an authorizer user device 702 (e.g. authorizer user device 14 of FIG. 1), and an immunization record database 308. The authorizer user device 702 may be a mobile device, such as a smartphone.

The vault 304 communicates, including sending and receiving data (request and response), with the authorizer user device 702 via a network connection. The vault 304 also communicates, including sending and receiving data, with the immunization record database 308 via a network connection. In some cases, the vault 304 may communicate with the database 308 through a database server, such as the database server 22 of FIG. 1.

The authorizer user device 702 includes a camera 704. The camera 704 function similarly to camera 310 of FIG. 3.

A health card 302 is presented and the camera 704 of the in-person verification device 306 acquires an image of the barcode on the health card 302 ("barcode image").

An alternate authorization credential is also provided to the authorizer user device 702. The alternate authorization credential may be an alternate identification (ID) card, such as a driver's license or credit card. The alternate authorization credential may be a login/password.

In FIG. 7A, the alternate authorization credential is an alternate ID card ("alt-ID card") 706. The alternate ID card 706 is presented to the camera 704 and a machine-readable feature of the alt-ID card 706, such as a 2D barcode, is imaged by the camera 704.

In cases where the alternate authorization credential is a login/password, the configuration of the login/password may be provided by inputting data to the authorization user device via an input interface (not shown). For example, the authorizer user device 702 may include a user interface (e.g. a web interface of client access terminal, described below) for receiving the login/password data inputted by the user.

The authorizer user device 306 also includes a client access terminal 708. The client access terminal 708 may be a web terminal, such as web terminal 312 of FIG. 3. The client access terminal 708 may include a web interface.

The client access terminal 708 facilitates communication with the vault 304, including sending requests to and receiving responses from the vault 304. The client access terminal 708 may use a web browser for communicating with the vault 304. The client access terminal 708 includes a user interface for inputting data to send to the vault 304 and for displaying data received from the vault 304. The user interface may run in the web browser. The authorizer user device 702 includes a display (not shown) for displaying the user interface.

The client access terminal 708 may include a web portal.

The client access terminal 708 may be implemented as an application on a smartphone, PC, or tablet.

The client access terminal 708 sends a request at 710 to register the health card 302 and link the alt-ID card 706 to the health card 302 to the vault 304. The request 710 includes the barcode image of the health card 302, the barcode image of the alt-ID card 706 (or other authorization credential data, such as login/email and password), and a client access terminal identifier ("terminal ID") of the client access terminal 708.

The vault 304 receives the request 710 and performs validation of the health card 302 and tokenization of the health card and alternate authentication credential (alt-ID 706).

The vault 304 includes a health card validation module 322. The health card validation module 318 is configured to validate the health card 302 using the barcode image received at 710 and generate a health card validation output. The vault 304 provides the health card 302 barcode image data as input to the health card validation module 322 at 324. The health card validation module 322 generates a health card validation output indicating whether the health card is valid or invalid and outputs the health card validation output to the vault 304 at 326. If the health card validation output indicates that the health card 302 is invalid, the vault 304 may send a response to the authorizer user device 702 indicating the health card 302 is invalid.

The health card validation output includes an insurance plan number (e.g. OHIP number) linked to the health card 302. As such, the health card validation module 322 may be configured to decode the barcode in the barcode image to obtain the insurance plan number.

The Alt ID 706 may be an ID card that is typically carried by the user. An example of this may be a passport, driver's license, employee ID card, or credit card. Various methods can be used to validate that the information from the alt-ID 706 is read properly, for example a check digit in a credit card number or driver's license may be used to protect from simple misreads of a card. To be effective, the number thus obtained should be unique, or at least unique with in the domain of enquiry. The alt-ID may be stored in the 'wallet' function of a smartphone. Such storage of the alt-ID in the wallet function may enhance convenience.

The vault 304 also includes a tokenization module 712. The vault 304 provides the health card number and alternate authentication credential data (alt-ID 706, login/password) as input to the tokenization module 712 at 714. The tokenization module 712 generates tokenized data from the health card number and alt-ID data and stores the tokenized data in a tokenized database 716. The tokenized database 716 may be an external or third-party database service that holds data (e.g. insurance plan number 332). The tokenization database 716 may have the effect of holding the insurance plan number 332 in a form of escrow.

The tokenization module 712 is configured to communicate with the tokenized database 716, such as to send tokenized data to the tokenized database 716 and receive tokenized data from the tokenized database 716 upon request. The tokenization module 712 outputs an insurance plan number 332 to the vault 304 at 718. Tokenization may be used for storing the health card number in a database separate from the vault 304. Such storage configuration may provide advantages. Once the identity of the individual and the associated health card number is established, the actual health card number can be securely stored at a different site and accessed and referenced through a substitute number (token). This token can then be used in lieu of a health card number to pass data access requests to the database server 308. Tokenized access may advantageously protect the actual health card number from being disclosed, thus reducing the opportunity for fraud or unauthorized access.

The tokenization module 712 and the tokenized database 716 may advantageously remove the need for the vault 304 to store or hold insurance plan numbers 332 or other potentially sensitive data.

In an embodiment, the tokenization module 712 may generate a tokenized ID that is linked to the insurance plan number 332. The tokenized ID may be the representation of the insurance plan number 332 that is stored in the vault 304. The insurance plan number 332 is stored in the tokenized database 716, which is located external to the vault 304. Once established, the tokenized ID may be used to retrieve the insurance plan number 332 from the tokenized database 716 when needed (e.g. for request 724, described below).

Upon validating the heath card 302 and generating and storing the tokenized data, the vault 304 sends a response at 720 indicating acceptance of the alt-ID 706 as the alternate authorization credential.

Referring now to FIG. 7B, the system 700 further includes an in-person verification device 306.

The in-person verification device 306 includes camera 310 for acquiring an image of the alt-ID card 706 and web terminal 312 for communicating with the vault 304.

The alt-ID card 706 is presented to the in-person verification device 306 and the camera 310 acquires a barcode image (or otherwise reads a machine-readable feature of the alt-ID 706) of the alt-ID card 706.

The in-person verification device 306 sends an immunization status request 722 from the web terminal 312 to the vault 304. The immunization status request 722 includes the alt-ID barcode image and a terminal ID. In cases where the authorizer user linked a login/password to their health card 302 in FIG. 7A, the request 722 includes the login/password data (which may be inputted to the web termina 312, such as via a web browser interface).

In an embodiment, the request 722 may include a business number or GPS coordinates. The business number or GPS coordinates may be used by the vault 304 to validate the requesting device 306 (i.e. validate as an authorized recipient of immunization status data).

The vault 304 obtains a unique identifier of the alt-ID (e.g. driver's license number) from the barcode image. There are a number of ways that the alt-ID number may be obtained. For example, the alt-ID number may be obtained through visual analysis of the human readable number on a card like a driver's license, through machine-reading a magnetic stripe on a card, through a RF connection like NFC, or through a smartphone or other device using NFC, WiFi, Bluetooth, or the like. In visual systems, the decoding of the alt-ID number can be performed through standard Optical Character Recognition means, or by optically reading a barcode on the card.

The vault 304 uses the tokenization module 712 to determine the health card number (insurance plan number 332) linked to the alt-ID 706 using the unique alt-ID identifier. The tokenization module 712 receives the alt-ID data as input at 714 and outputs an insurance plan number 332 at 718. The insurance plan number 332 is linked to the alt-ID 706.

The vault 304 validates the insurance plan number 332 using the health card validation module 322.

The vault 304 sends a request at 724 for an immunization record 330 to the immunization record database 308. The request 724 includes the validated insurance plan number 332.

The immunization record database 308 retrieves the immunization record 330 using the insurance plan identifier 332 and sends a response at 726 to the vault 304. The response 726 includes the immunization record data 330.

The vault 304 receives the response 726 and determines an immunization status using the immunization record 330. In particular, the vault 304 provides the immunization record 330 as input to the policy engine (e.g. policy engine 1102 of FIG. 11). The policy engine determines the immunization status (e.g. immunization status 1104) using the immunization record 330 data.

The vault 304 sends a response at 728 to the in-person verification device 306. The response 728 may be similar to the response 336 of FIG. 3. The response 728 includes the immunization status.

The in-person verification device 306 receives the immunization status response 728 and the web terminal 312 displays the immunization status in the user interface.

Figure 8:
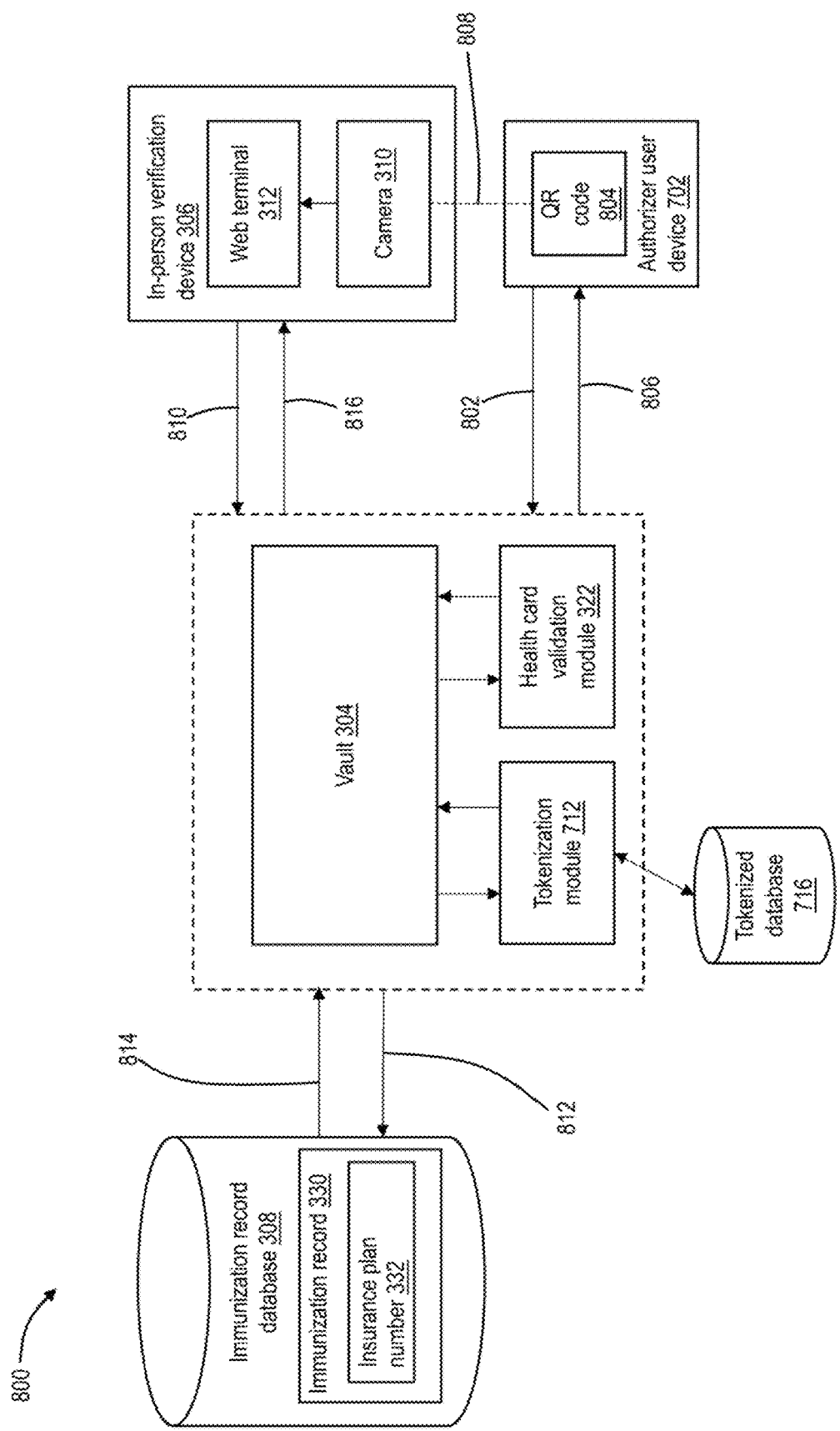
FIG. 8 is a block diagram of a system for in-person verification of an immunization status using a non-health card authentication credential (QR code), according to an embodiment.

Referring now to FIG. 8, shown therein is a system 800 for in-person verification of an immunization status using a non-health card authentication credential (quick response "QR" code), according to an embodiment.

In the example of FIG. 8, the individual/authorizer user has previously registered their health card 302 and linked an alternate authentication credential (e.g. alt-ID 706, login/password) to the health card 302 in the system. In other embodiments, the individual user may use the health card 302 without linking an alternate authentication credential and access the system using the health card 302 (e.g. via sending a barcode image of the health card 302 to the vault 304.

The system 800 includes an authorizer user device 702, an in-person verification device 306, a vault 304, and an immunization record database 308.

The authorizer user device 702 includes a client access terminal 708 (not shown). The authorizer user device 702 sends a QR code request at 802 to the vault 304 using the client access terminal 708. The client access terminal 708 may include an application ("app") or a web browser interface. The request 802 includes alternate authentication credential data (e.g. alt-ID 706, login/password). As noted, in some cases, such as where the authorizer user has not linked an alternate authentication credential to their health card 302, the request 802 may include a barcode image of the health card 302 (captured via a camera 704 at the authorizer user device 702).

The vault 304 receives the request 802 and obtains the insurance plan number 332 linked to the alternate authentication credential data. This may include using the tokenization module 712 or the health card validation module 322.

The vault 304 includes a QR code generator module (not shown). The QR code generator generates a QR code encoding an authentication credential of the authorizer user (e.g. insurance plan number). Similarly, the vault 304 may use the QR code generator to generate a QR code encoding the alternate authentication credential data. Such alternate authentication credential data can be decoded from the QR code by the vault 304 and used by the vault 304 to obtain the insurance plan number 332 linked to the alternate authentication credential.

The vault 304 obtains the authentication credential from the request 802 and uses the QR code generator to generate a QR code 804 encoding the authentication credential. The QR code 804 may function as a pointer to an insurance plan number 332 of the authorizer user stored by or accessible by the vault 304 using the pointer.

The vault 304 sends a response at 806 to the authorizer user device 702 accepting the authentication credential provided in request 802. The response 806 includes the QR code 804. The QR code 804 is stored in data storage on the authorizer user device 702.

The authorizer user device 702 includes a QR code display module (not shown) configured to display the QR code 804 for reading (imaging, scanning) by the in-person verification device 306. The QR code display module may be a component of the client access terminal 708, such as a web browser interface. In other cases, the QR code display module may be a module that does not require an internet connection and can thus display the QR code 804 when the authorizer user device 702 is offline (or online).

The authorizer user device 702 displaying the QR code 804 is presented to the in-person validation device 306. In particular, the camera 310 of the in-person verification device 306 acquires an image of the QR code 804 ("QR code image") at 808.

The in-person verification device 306 sends an immunization status request at 810 to the vault 304 using the web terminal 312. The request 810 includes the QR code 804.

The vault 304 uses a QR code decoder module (not shown) configured to decode QR codes to obtain data encoded therein. The QR code decoder module decodes the QR code 804 provided in the request 810 to obtain the authentication credential data.

If the authentication credential data is an alternate (non-health card) authentication credential, then the vault 304 obtains the insurance plan number 332 linked to the alternate authentication credential using the tokenization module 712. The vault 304 sends an immunization record request at 812 to the immunization record database 308. The immunization record request 812 includes the insurance plan number 332.

If the authentication credential data obtained from the QR code 804 is the insurance plan number 332, the vault 304 sends the request 812 including the insurance plan number 332 to the immunization record database 308. The vault 304 may validate the insurance plan number 332 obtained from the QR code 804 using the health card validation module 322 prior to sending the immunization record request 812.

The immunization record database 308 retrieves the immunization record 330 using the insurance plan number 332. The immunization record database 308 sends a response at 814 to the vault 304. The response 814 includes the immunization record 330.

The vault 304 receives the response 814 and obtains the immunization record 330. The immunization record 330 is provided as input to the policy engine (not shown). The policy engine determines and outputs the immunization status.

The vault 304 sends a response at 816 to the in-person verification device 306. The response 816 includes the immunization status.

The in-person verification device 306 receives the response 816 and displays the immunization status data using the web terminal 312 (e.g. in a web browser interface).

The displayed immunization status can be used by an operator of the in-person verification device 306 to determine whether to permit the individual (authorizer user) to access.

Figure 9:
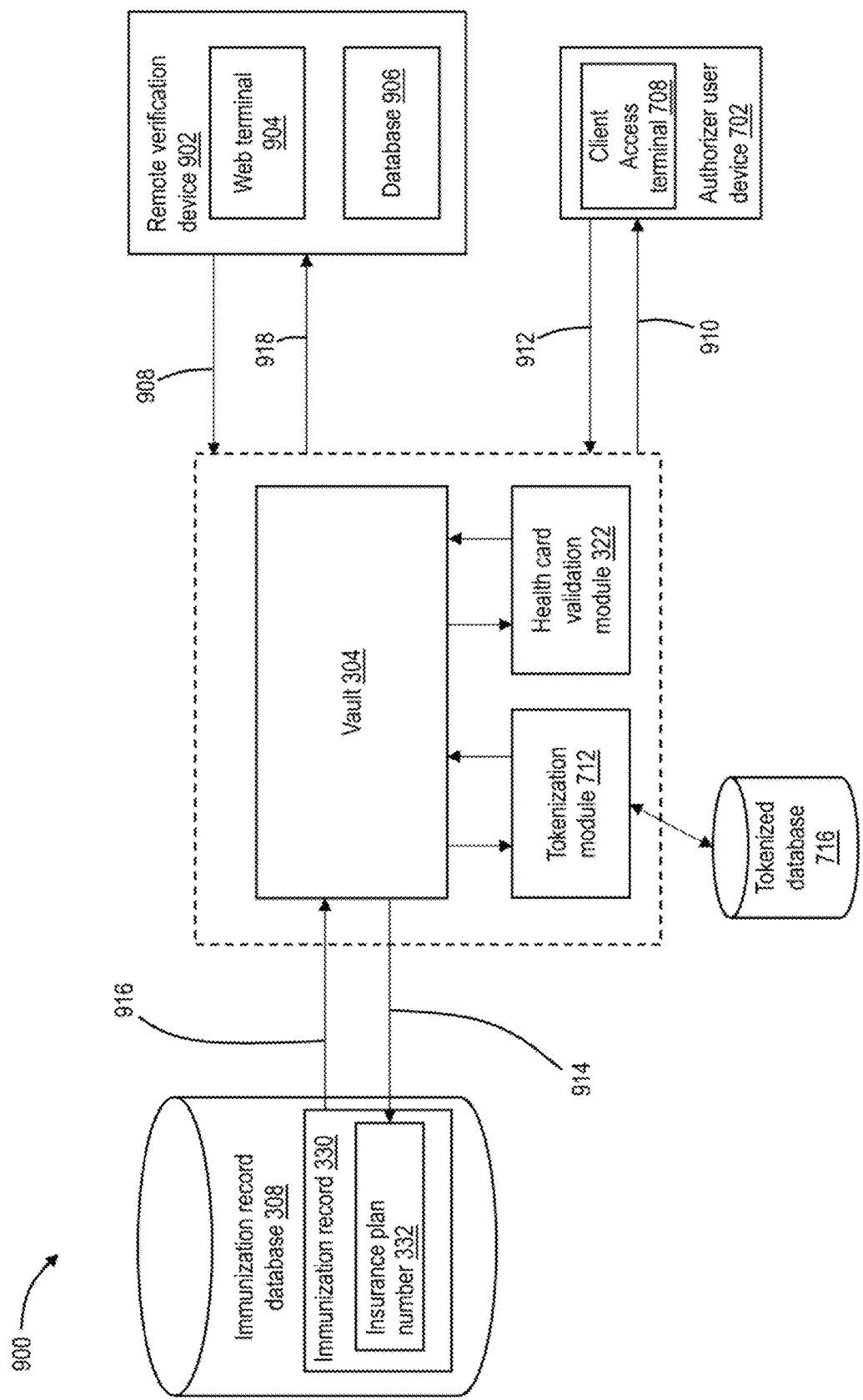
FIG. 9 is a block diagram of a system for remote verification of an immunization status, according to an embodiment.

Referring now to FIG. 9, shown therein is a system 900 for remote verification of an immunization status, according to an embodiment. The system 900 may be used for batch remote verification (i.e. verification of immunization statuses for a batch of individuals). The system 900 may provide for remote management of immunization statuses of groups of individuals, including management by exception.

The system includes a remote verification device 902, vault 304, immunization record database 308, and authorizer user device 702. The remote verification device 902 may be the remote verification device 18 of FIG. 1.

The remote verification device 902 includes a web terminal 904. The remote verification device 902 communicates with the vault 304 via the web terminal 904. The web terminal 904 may function similarly to the web terminal 312.

The remote verification device 902 includes a database 906. The database 906 stores data about a group of individuals (authorizer users) who have a structured relationship with the verifier party. Generally, the data in the database 906 includes some identifying information about the individuals (e.g. email address). For example, the verifier party may be an employer, an airline, a school, a border crossing agency, etc., and the individuals may be employees, airline passengers, students, essential workers, etc.

The database 906 includes a unique identifier for each individual. The unique identifier may be an identifier specifically related to the structured relationship, such as a student number, employee number, passenger number, essential worker number, etc. The database 906 also includes an email address for each individual. In other embodiments, the database 906 may include in addition to or instead of an email address data for another method of contact, such as a mobile phone number (and may use SMS or other message instead of email).

Generally, the database 906 does not include health card numbers for the individuals (though it is possible).

In other embodiments, the verifier party may input data about individuals (e.g. contact data, unique identifier) into the web terminal 904 via a web interface or the like. The data may be provided as a list. In such cases, the remote verification device 902 may not have the database 906. In an example, the web terminal 904 may include a user interface for pasting or otherwise inputting a list of individuals to whom requests are to be sent.

The remote verification device 902 sends a request at 908 to distribute email authorization requests to specified authorizer users (i.e. individuals in the database 906). The request 908 is basically a request for the vault 304 to forward access requests to specified individuals.

Generally, the request 908 specifies a batch of individuals in database 906 for which the verifier party wants to know an immunization status. The batch may be in a CSV format. The batch may be in an XLS format. The batch may be provided via a web interface.

The request 908 specifies contact data (e.g. an email address, a mobile phone number) for a plurality of individuals. In FIG. 9, the contact data is an email address. In other embodiments, the contact data may relate to another method of electronic communication, such as a mobile phone number for text message-based communication (e.g. SMS).

The request 908 may include other data for each individual, such as the unique identifier (e.g. employee number, student number, etc.).

The request 908 may include a list of email addresses and corresponding unique identifiers. For example, the request 908 may include a list of [email, Identifier].

The request 908 may include a terminal ID of the remote verification device 902.

The vault 304 receives the request 908 and generates an email (or other electronic message, as the case may be) to be sent to each individual authorizer user using their respective email address. The email may include a hyperlink. The link is selectable by the recipient and may direct the user to a user interface, such as webpage, where data can be inputted (insurance plan number, permissions to access immunization status).

The vault 304 may include web terminal validation module 316 for validating the web terminal 904.

The vault 304 sends the email to the authorizer user device 702 at 910. It is to be understood that this step and the ones that follow are described in the context of a single authorizer user but are performed for a plurality of authorizer users specified in the batch request 908.

The authorizer user device 702 includes client access terminal 708. The client access terminal 708 displays the email. The email directs the recipient (e.g. via a link in the email) to a webpage interface for inputting an insurance plan number 332 and data access permission (approve access to immunization status). The access approval authorizes the verifier party to access the authorizer user's immunization status. The permission may be inputted by selecting a user interface element, such as a clickable icon.

The authorizer user inputs the insurance plan number 332 and the data access permission via the client access terminal 708. In some cases, the authorizer user may be able to specify period of time for which the approved access is granted (e.g. one time use, specifying an end date, until revoked by the user, etc.). For example, the user interface or webpage may be configured such that the user can select or input the permission validity period into the user interface for communication to the vault 304 via the client access terminal 708.

The authorizer user device 702 sends a response at 912 to the vault. The response 912 includes the access approval and the insurance plan number 332 (if access granted). If the permission was not authorized, the response indicates access is not approved.

The vault 304 receives the response 912 including the access approval and the insurance plan number 332.

The vault 304 may validate the insurance plan number 332 using health card validation module 322.

The vault 304 stores a mapping or link between the insurance plan number 332 and the email address or unique identifier of the authorizer user. This links the insurance plan number 332 to the request.

The vault 304 also stores access approval data for the access approval provided by the authorizer user 702 in the response 912. The access approval data is linked to the authorizer user. This may include linking the access approval data to any one or more of the insurance plan number 332, the unique identifier, and the email address (or other contact data). The access approval data may include a permission validity period. The permission validity period may be a one-time access, a defined period of time, or until revoked by the authorizer user. The permission validity period may be included in the response 912 provided by the authorizer user device 702. The permission validity period may be inputted to the client access terminal by the authorizer user (e.g. in a web interface). In some cases, the permission validity period may be specified as a specific window of time (e.g. Jan. 1 2020 to Jan. 31 2020). In some cases, the permission validity period be specified as a duration from present (e.g. for 5 months). In some cases, the permission validity period may be conditional on another external event or condition (e.g. while I (the authorizer user) am still a student at Harvard University). Such external events may require a mechanism to interrogate or be informed of any change in status.

The access approval data may also be linked to a unique identifier of the verifier party. For example, the unique identifier of the verifier party may be the terminal ID of the remote verification device, or other identifier such as a business number or educational institution number.

In an embodiment, the access approval data stored in the vault 304 may include an access approval (permission to access the immunization status), an access approval validity period, a unique identifier of the party authorizing access (authorizer user), and a unique identifier of the party who is authorized to access (verifier party). The access approval data may enable the verifier party to inquire multiple times about the immunization status of a batch of individuals without requiring input from the authorizer user other than the initial access approval (provided by response 912). In some cases, since unique identifier number sets may overlap, an extended unique identifier number may be used. The extended unique identifier may be used to effectively build an identifier that includes an identifier component for the verifier party and a component authorizer. For example, an employer may have a business number and a 5 digit employee number (for an individual or authorizer user for which an immunization status is requested). The unique identifier associated with requests from that employer may be of the form xxxxxxx.yyyyy, where xxxxxxx is the business number and yyyyy is the employee number.

The vault 304 sends an immunization record request at 914 to the immunization record database 308. The request 914 includes the insurance plan number 332.

The immunization record database 308 retrieves an immunization record 330 using the insurance plan number 332 and sends a response at 916 to the vault 304 including the immunization record 330.

The vault 304 receives the response 916 and inputs the immunization record data 330 into the policy engine (not shown). The policy engine outputs an immunization status determination (e.g. PASS, FAIL). In some cases, the immunization status may include additional data.

In some cases, the batch immunization statuses can be filtered by verifier party requirements (e.g. employer, school requirements). The filtering may be performed by the vault 304. For example, the vault 304 may include a status filtering module that encodes rules for filtering immunization statuses. The rules may be provided by the verifier party. The rules may be provided to the vault 304 via a web interface at the remote verification device 902. As an example, and using the data from FIG. 6, a filter to admit a child into an educational institution might be: a) must have two shots of Moderna within 4 weeks of each other AND b) the last Moderna shot must be no more than 1 year ago OR c) must have Pfizer shot less than 18 months ago. Complex rules can be built and implemented to filter the immunization events using AND and OR logic. Different sets of filter rules can be constructed for different risk situations. For example, hospital workers may have a different set of rules from school children, and different again for access to a communal space like a restaurant. Warnings may also be constructed by the vault 304 using similar logic trees. One such example is: a) if last Moderna immunization event is greater than 50 weeks, warn that a booster is required.

The vault 304 sends an immunization status response at 918 to the remote verification device. The response 918 may include an immunization status for each authorizer user that has access approval data in the vault 304 (the access approval provided in response 912). The response 918 includes data describing the individual corresponding to each immunization status. The data may be the unique identifier of the individual or the email address (or other contact data). Generally, the data used to describe the individual corresponding to the immunization status is present in the database 906 such that the immunization status can be linked to the individual in the database 906. For example, in an embodiment where the verifier party is an employer, the batch request at 908 may include an employee number and email address for each employee in the batch request. Each employee is represented in the database 906 by the employee number. The response 918 from the vault 304 includes the immunization statuses and corresponding employee numbers for each immunization status (e.g. [Identifier, Immunization status]). In this way, the received immunization status may be integrated into the database 906. Also, there is no need to share personal information of the employee beyond what is already known by the employer (i.e. what is already in the database 906).

The response 918 may include a key (e.g. [validity time]) for subsequent direct access by the verifier party.

The response 918 may include a status validity period. The status validity period indicates how long the determined immunization status is valid. The status validity periods can be monitored by the verifier party to identify individuals with an impending change in immunization status (e.g. PASS to FAIL). The verifier party may be able to set an automatic request via the web terminal 904. This feature may enable the verifier party to set an automatic request time for a particular individual based on the status validity period for that individual.

In some embodiments, status validity periods may be stored at or otherwise accessible to the vault 304. The status validity periods may be linked to other data, such as a health card number 332 (for an authorizer user) or a unique individual identifier (for a verifier party). The stored status validity period may be linked to contact data for reporting a status change (or impending status change). The vault 304 may be configured to monitor the stored status validity periods for a state change (e.g. PASS to FAIL) or an impending state change (e.g. PASS to FAIL within 14 days). Upon identifying a state change (or impending state change), the vault 304 may be configured to send a message (e.g. email, text message) to a user (authorizer user, verifier party user) that is linked to the status validity period. Accordingly, data identifying an authorizer user and/or a verifier party may be linked to the status validity period. The data may include contact data for the user (e.g. email address, phone number for text message). The message may indicate that an immunization status state change has taken place or is scheduled to take place at a specified time.

By storing the access approval data of the authorizer users at the vault 304, the remote verification device 902 (and the verifier party user) can send requests similar to request 908 for the immunization statuses of a batch of individuals at multiple points in time during which the access approval is valid. For example, in a school scenario, the access approval validity period may be for a school year, and the school (verifier party) may inquire about the immunization statuses of its students on a daily basis.

The system 900 may provide for efficient validation for groups. The system 900 may be particularly advantageous in situations where in-person validation of every person at point of entry would be impractical or inefficient and where a structured relationship of some sort exists between the verifier party and the authorizer users (i.e. the verifier party knows some information about the authorizer users).

In an embodiment, the system 900 may be used to perform immunization validation on essential workers at a border crossing (e.g. Canada-US border). The remote verification device 902 may be operated by a border patrol agency (e.g. Canada Border Services Agency (CBSA) or the like). In such a case, the border patrol agency is the verifier party (verifying entity). The authorizer user device 702 may be operated by an "essential worker". An essential worker may be considered a public-sector or private-sector employee who is considered to provide an essential service. Those who qualify as an essential worker may determine according to rules dictated by government (e.g. provincial government, federal government). As such, the term "essential worker" refers generally to a class of workers who have been deemed by relevant government to be "essential".

The database 906 may be a database of essential workers. The essential worker database may be maintained by a government entity.

The border patrol agency sends a batch request for immunization statuses of essential workers from the remote verification device 902 at 908. The remote verification device 902 stores or otherwise has access to the essential workers database 906. The database 906 stores some kind of unique identifier for each essential worker in the database 906 (e.g. essential worker ID). The request 908 may include the unique identifier.

The vault 304 sends emails (or other electronic messages) to the email addresses in the batch request 908 at 910.

The essential worker receives the email 910 at the authorizer user device 702 and sends a response 912 approving access and including their insurance plan number 332.

The vault 304 requests the immunization record 330 for the insurance plan number 332 from the immunization record database 308 at 914 and receives a response 916 including the immunization record 330. The immunization record 330 is processed by the policy engine of the vault 304 to generate an immunization status. The immunization status may be filtered. The immunization statuses for the essential workers specified in the batch request and who approved access may be batched and sent to the remote verification device 902 at 918.

The access approval data for the essential workers is stored in the vault 304 for subsequent immunization status requests by the remote verification device 902.

The operator of the remote verification device 902 can then authenticate the essential worker when attempting to cross the border in whatever manner is appropriate to confirm the essential work is who they say they are and confirm the immunization status using the database 906.

The system 900 may provide various advantages. For example, the vault 304 links the insurance plan number 332 provided by the authorizer user to the unique identifier for the authorizer user that is known by the remote verifier party (e.g. student number, email address, employee number). In doing so, the remote verifier party does not need to know the insurance plan number 332. The contact data for the authorizer user provided by the remote verifier party is sufficient to contact the authorizer user and obtain the insurance plan number 332 (and access approval).

Figure 10:
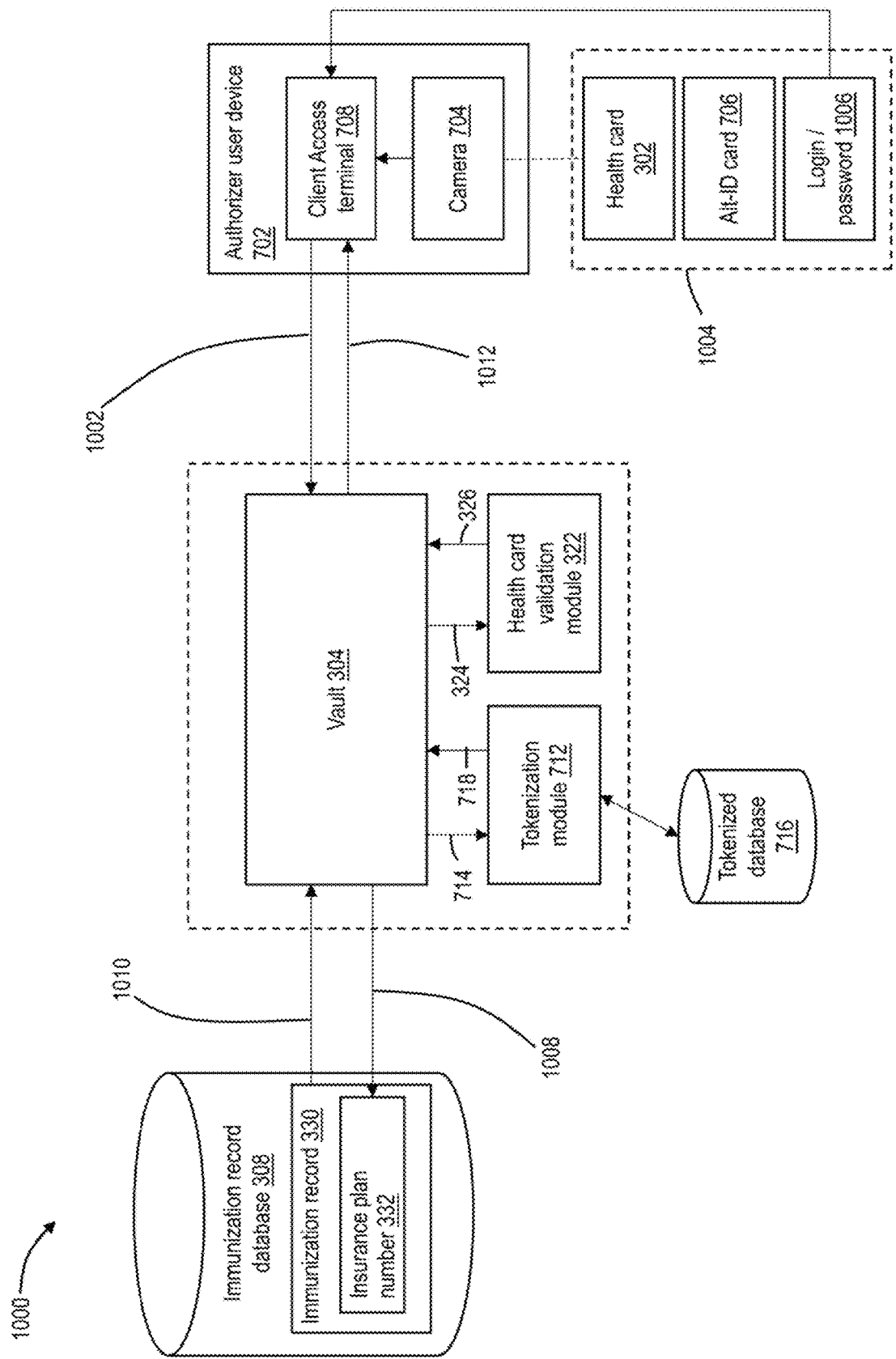
FIG. 10 is a block diagram of a system for authorizer user verification of the authorizer user's own immunization status, according to an embodiment.

Referring now to FIG. 10, shown therein is a system 1000 for authorizer user verification of the authorizer user's own immunization status, according to an embodiment.

The system 1000 includes components previously described in reference to other figures herein and such components are referenced with like reference numerals. Such components are understood to be capable of performing the same or similar functions as previously described.

In the example of FIG. 10, the authorizer user may already be "registered". Being registered refers to the process of linking a health card number 332 in the system to an alternate authentication credential (e.g. using the registration process of FIG. 7A).

The authorizer user device sends an immunization status request at 1002 to the vault 304. The request 1002 may include a terminal ID of the authorizer user device 702 (client access terminal 708).

The status may be requested using a health card 302 or an alternate authentication credential linked to the health card 302 in the vault 304.

The request 1002 also includes authentication data 1004. The authentication data may be a barcode image of health card 302 acquired by camera 704 of the authorizer user device 702. The authentication data may be a barcode image (or the like) of alt-ID card 706 acquired by the camera 704. The alt-ID card 706 is previously linked in the system to the health card number 332 of the authorizer user. The authentication data may be a login/password 1006. The login/password may be inputted to the authorizer user device 702 via the client access terminal 708, which may include a web interface. The login/password 1006 is previously linked in the system to the health card number 332.

The vault 304 may verify the client access terminal 708 using the terminal ID.

If the request 1002 includes authentication data of an alternate authentication credential, the vault 304 obtains the health card number 332 linked to the alternate authentication credential. This may include using the tokenization module 712.

If the request 1002 includes a health card barcode image, the vault 304 processes the barcode image to obtain the health card number 332. The health card number 332 is validated using the health card validation module 322.

The vault 304 sends an immunization record request at 1008 to the immunization record database 308. The request 1008 includes the health card number 332.

The database 308 retrieves the immunization record 330 using the health card number 332 and sends a response at 1010 to the vault 304. The response 1010 includes the immunization record 330.

The vault 304 processes the received immunization record 330 using the policy engine (not shown) to determine an immunization status.

The vault sends an immunization status response at 1012 to the authorizer user device 702. The response 1012 includes the immunization status.

The authorizer user device 702 receives the response 1012 via the client access terminal 708. The client access terminal 708 displays the immunization status (e.g. in a web interface).

In the example of FIG. 10, the authorizer user (the individual whose immunization status is of concern and being requested) and the requesting party (the user requesting the immunization status, also called the verifier party) are the same. The system 1000 enables an authorizer user to inquire about their own immunization status. In doing so, the authorizer user can identify perceived errors in their immunization status based on their own personal knowledge (i.e. I should be ok (PASS) based on my last vaccination, but the system is telling me I'm not ok (FAIL)).

The authorizer user can also confirm their immunization status prior to an access scenario, whether such access scenario involves in-person or remote verification. This provides predictability to the authorizer user as to what the response received at the verification device will be. As such, this feature may avoid an individual traveling to an access point (e.g. restaurant, concert, border crossing, place of employment, school) and finding out access is denied based on a negative immunization status. Further, by enabling the authorizer user to check their immunization status using the system, the system may provide the individual with knowledge about a negative immunization status (or, potentially, an imminent negative immunization status) and enable them to take proactive steps to address the immunization status (e.g. make an inquiry, schedule an appointment to get vaccinated, get vaccinated).

Figure 11:
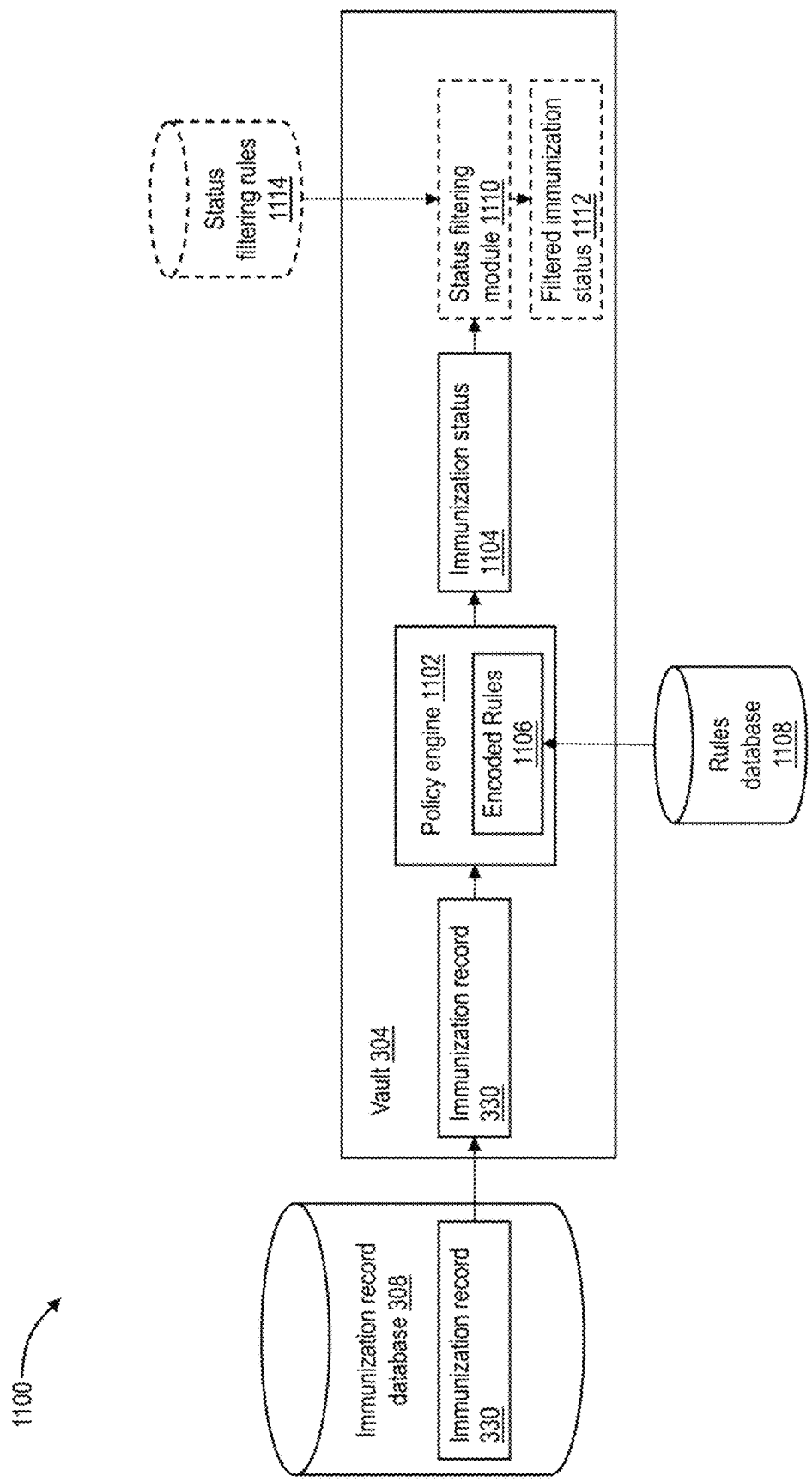
FIG. 11 is a block diagram of an immunization status determination at a vault computing device using a policy engine, according to an embodiment.

Referring now to FIG. 11, shown therein is a representation 1100 of an immunization status determination performed at vault 304, according to an embodiment.

The vault 304 is in communication with and receives an immunization record 330 from the immunization record database 308.

The vault 304 provides the immunization record 330 as input to a policy engine 1102. The policy engine 1102 determines and outputs an immunization status 1104. The immunization status 1104 indicates whether the corresponding individual has a verified immunization status or not. In an embodiment, the immunization status 1104 may be a binary representation of immunization status (e.g. PASS/FAIL).

The policy engine 1102 includes encoded rules 1106. The encoded rules 1106 are used to determine the immunization status 1104. The encoded rules 1106 represent software logic that is implemented by the policy engine 1102. The encoded rules 1106 may be in the form of a decision matrix.

The encoded rules 1106 are representations of rules, policies, guidelines, or regulations (collectively, "rules") issued by relevant health authorities or governmental bodies related to immunization verification. For example, the rules may specify valid exemptions from getting vaccinated, a list of approved vaccines, a length of time for which a particular vaccination is good or effective (immunization credential validity period), etc. In some cases, the rules may include different thresholds for different types of venues or greater sophistication or complexity with respect to the layout of a particular venue (e.g. does the venue seating have individuals 6 feet apart). In some cases, the rules may incorporate an exception density where a venue is permitted to have a certain number or proportion of unvaccinated individuals. Such rules may, in some embodiments, be included in status filtering rules, described below. In general, the nature of the rules is not particularly limited.

In some cases, the rules may be codable as human readable rules (e.g. a human readable policy). For example, the rules may be expressed in a script file. By having a human readable representation of the rules, such as in a script file, the rules can be read and interpreted by a human user of the system. For example, the system may be configured send the rules in human readable format from the vault 304 to the verifier device, where the human readable rules may be displayed (e.g. in web terminal).

Rules data representing the rules is stored in a rules database 1108. The rules database 1108 is used to generate the encoded rules 1106. The rules database 1108 may be in communication with or otherwise accessible to the vault 304. In some cases, the rules database 1108 may be stored at the vault 304. In such cases, the rules database 1108 at the vault 304 may be updated from time to time using and external rules database 1108.

The rules database 1108 may be maintained by a government entity. The government entity may be a health authority.

The encoded rules 1106 may be updated over time using the rules database 1108. For example, policy, rules, or guidelines may change over time as situations develop (e.g. new vaccines approved, changing validity periods, new exemption codes, new data affecting previously held views, booster vaccinations, what constitutes "fully vaccinated", etc.). This may be particularly advantageous in dynamic situations, such as pandemics, where information is being acquired in real-time about the disease, virus, and vaccines. Accordingly, the vault 304 may be configured to connect to the rules database 1108 in order to facilitate updating the encoded rules 1106. In some cases, the rules database 1108 may push updates to the vault 304 and the vault 304 updates the encoded rules 1106 to reflect the updates to the rules in the rules database 1108. In addition to the encoded rules applicable for specific types of congregation settings (e.g. businesses, educational institutions, concerts, etc.) the system may be configured to enable the verifier party to modify or change the standard encoded rules for the purpose of computing hypothetical scenarios. This may be particularly useful for operators of congregation settings to determine the impact of more restrictive rules that would generate greater safety but that may have an impact on the populations attending these congregation settings. For example, an educational institution may note that the government policy for a particular vaccine's effectiveness is 6 months, and the institution would like to know the impact of making their internal policy not 6 months, but a safer 5 months. The ability to modify or create variations for hypothetical queries may help in the calculus of safe gathering places, including workplaces.

The vault 304 may also include a status filtering module 1110. The status filtering module 1110 receives the immunization status 1104 as input and outputs a filtered immunization status 1112. In some embodiments, the status filtering module 1110 may be a component of the policy engine 1102 and the immunization status 1104 reflects the filtered immunization status 1112.

The status filtering module 1110 includes encoded rules (not shown, similar to encoded rules 1106) which represent software logic implemented by the status filtering module 1110. In particular, the encoded rules of the filtering module 1110 represent rules or criteria for a particular verifier party (e.g. remote verifier party, such as a school or an employer), a particular class of verifier party (e.g. school, employer, public transportation authority), or a particular class of access scenario (e.g. accessing a restaurant, accessing a sporting event, accessing a concert, accessing a mode of public transportation, etc.). The rules from which the encoded rules are derived are stored in a status filtering rules database 1114. The status filtering rules database 1114 may be in communication with or otherwise accessible to the vault 304. The filtering rules database 1114 may be maintained by the verifier party. In some cases, the filtering rules database 1114 may be stored at the vault 304.

In some cases, the status filtering module 1110 may include a plurality of masks. Each mask corresponds to a particular set of criteria or rules applicable to a particular verifier party, a particular class or type of verifier party, or a particular class or type of access scenario. The vault 304 receives data from the verification device (in-person 306 or remote 902) which indicates a set of rules/criteria or mask to apply to the immunization status determination. The corresponding mask is applied to the immunization status determination.

In an embodiment, the web terminal (e.g. web terminal 312, 904) may present a web interface that enables a verifier party to select or input the data for specifying the rules/criteria or mask to apply to the immunization status. For example, the web interface may display options of "going to a restaurant", "going to a sports event", and "getting on public transit (bus, train, etc.)". The user makes a selection, and the selection data is included with the immunization status request sent to the vault 304. The vault 304 determines the appropriate mask to apply to the immunization status determination from the selection data and applies the mask using the policy engine 1102 or filtering module 1110.

In another embodiment, the system may use different access points or addresses for different sets of criteria/rules/restrictions (e.g. log in to restaurant app if a restaurant, log in to a concert venue app if a concert venue etc.). The verifier party may input data indicating the access point via the web terminal. The access point data is included with the immunization status request sent to the vault 304. The vault receives the request and obtains the access point data. The vault 304 determines the appropriate mask to apply to the immunization record 330 in the immunization status determination and applies the mask.

Generally, the status filtering module 1110 may be used to filter immunization statuses 1106 according to verifier party-specific rules. This may be particularly useful in remote verification scenarios (e.g. FIG. 9), where a verifier party such as a school or employer may have specific requirements.

In an example, the status filtering module 1110 may be configured to filter out all PASS immunization statuses in a batch request. This may enable the vault 304 to send a response to the remote verification device that includes only those immunization statuses 1106 that are FAIL. In another example, the status filtering module 1110 may filter out all PASS immunization statuses that have a validity period of longer than a defined period of time (e.g. 7 days). As such, the response from the vault 304 may include the FAIL immunization statuses as well as those immunization statuses 1106 that are presently PASS but may soon become a FAIL. This may enable the verifier party to manage statuses more effectively. Other embodiments may include regulating events for immunized person density. For example, it may be permissible to have a small proportion of unimmunized people in a specific environment. The proportion of unimmunized people for a specific environment (e.g. workplace, sporting event, restaurant) may be tallied and the entry criteria may be adjusted to ensure that the proportion is within safe limits.

Figure 12:
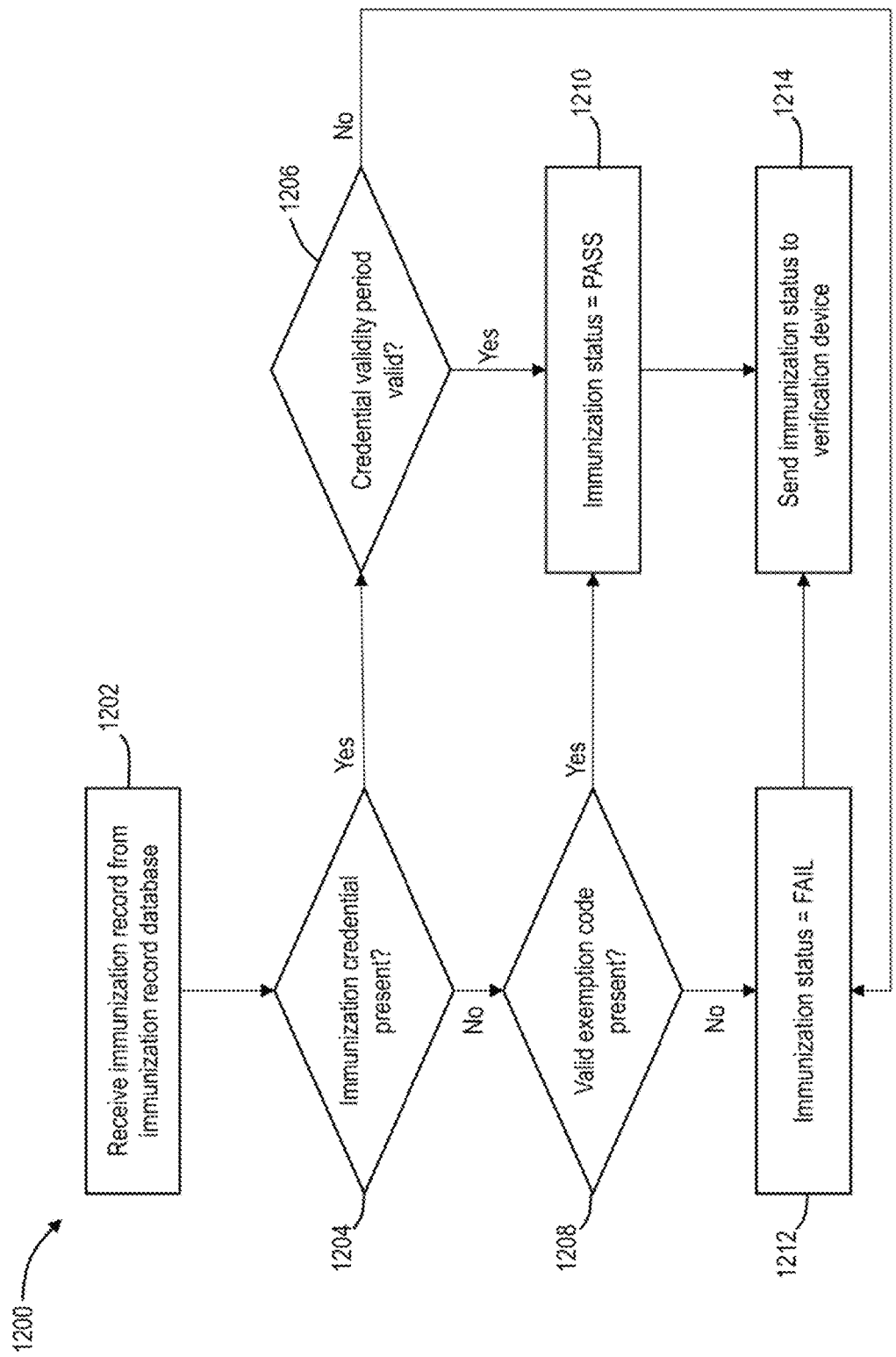
FIG. 12 is a flow diagram of a method of determining an immunization status using immunization record data obtained from an immunization record database, according to an embodiment.

Referring now to FIG. 12, shown therein is a method 1200 of determining an immunization status using immunization record data from an immunization record database, according to an embodiment.

The method 1200 is implemented by the vault 304. In particular, aspects of the method 1200 may be performed by the policy engine 1102 of FIG. 11.

At 1202, an immunization record is received from the immunization record database. The immunization record may be the immunization record 330.

At 1204, the immunization record is analyzed to determine whether an immunization credential is present in the immunization record. The immunization credential describes an immunization event, such as inoculation with a vaccine (e.g. Vaccine A, Vaccine A booster, Vaccine B).

In an embodiment, the determination at 1204 may be made for each valid immunization credential (e.g. Vaccine A first shot, Vaccine A booster, Vaccine B, Vaccine C first shot, Vaccine C booster, etc.). The valid immunization credentials may be provided by the rules database and encoded in the policy engine.

If a valid immunization credential is present in the record at 1204, the method 1200 proceeds to 1206. If a valid immunization credential is not present in the record at 1204, the method 1200 proceeds to 1208.

At 1206, the immunization record data is analyzed to determine whether the valid immunization credential determined at 1204 has a valid credential validity period. Generally, the immunization credential validity period (or record validity period) corresponds to a period of time for which the immunization credential will provide a "pass" immunization status. This will generally correspond with the period of time for which the vaccine administered in the immunization event is deemed to provide acceptable levels of immunity by relevant health or other authorities. For example, an immunization credential of "Vaccine A first shot" may have a credential validity period of three months, while "Vaccine A booster" may have a credential validity period of five years. The credential validity period may be provided by the rules database and encoded in the policy engine.

Accordingly, the determination at 1206 may include referencing a date in the immunization record 330 associated with the immunization credential (i.e. the date on which the vaccine was administered) and the then-current date and comparing the determined period of time between the inoculation date and the current date to the validity period of the immunization credential.

If the validity period of the immunization credential is valid at 1206, the method 1200 proceeds to 1210. If the validity period of the immunization credential is invalid at 1206, the method proceeds to 1212.

Note that the method 1200 may be configured to perform steps 1204 and 1206 for each possible or valid immunization credential. For example, if a Vaccine A immunization credential is not identified, then the method may proceed to determining whether a Vaccine B immunization credential is present in the immunization record data.

At 1210, the immunization status is determined to be a pass ("PASS").

At 1212, the immunization status is determined to be a fail ("FAIL"). In some cases, the method 1200 may be configured such that a "no" determination at 1206 proceeds to a valid exemption code determination 1208 as described below.

At 1214, the determined immunization status (from either 1210 or 1212) is sent to the verification device. The verification device may be an in-person verification device or a remote verification device (operated by a verifier party or an authorizer user/individual). In some cases, the immunization status sent to the verification device may include a remaining validity period. The remaining validity period indicates how long the immunization credential giving a PASS immunization status will remain valid (i.e. continue to give a PASS immunization status). The remaining validity period may be determined at 1206 (e.g. using the date of inoculation, the current date, and the credential validity period).

Referring again to 1204, if an immunization credential is not identified in the immunization record 330, the method 1200 proceeds to determine at 1208 if the immunization record 330 includes a valid exemption code. Generally, an exemption code represents an exemption from the requirement to get vaccinated, such as a severe allergy. There may be a plurality of different exemption codes.

If a valid exemption code is present at 1208, the method proceeds to 1210. At 1210, the immunization status is determined to be a PASS.

If a valid exemption code is not present at 1208, the method proceeds to 1212. At 1212, the immunization status is determined to be a FAIL.

Note that method 1200 may be configured to perform step 1208 for each possible or valid exemption code in the system.

The immunization status determined at 1212 or 1210 is sent to the verification device at 1214.

Figure 13:
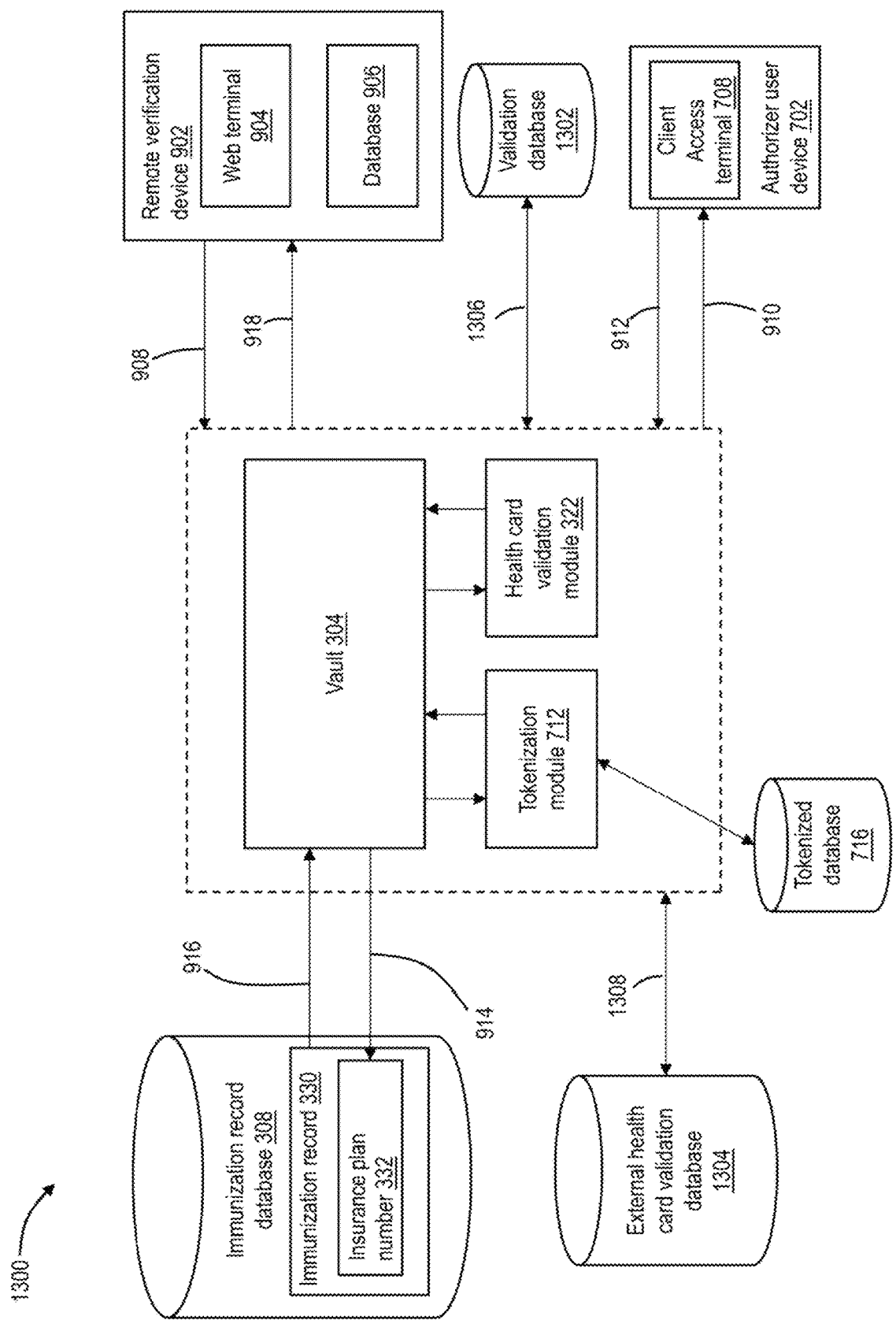
FIG. 13 is a block diagram of a system for remote verification including enhanced validation, according to an embodiment.

Referring now to FIG. 13, shown therein is a system 1300 for remote verification including enhanced validation, according to an embodiment.

The system 1300 includes components previously described in reference to other figures herein and such components are referenced with like reference numerals. Such components are understood to be capable of performing the same or similar functions as previously described.

The system 1300 is similar to system 900 of FIG. 9, but further includes a validation database 1302 ("verifier party validation database") and an external health card validation database 1304.

The vault 304 communicates with the validation database 1302, such as by sending requests to and receiving responses from the validation database 1302. Communication between the vault 304 and the validation database 1302 is represented at 1306.

Generally, the validation database 1302 stores data on a plurality of verifier parties (operators of the remote verification device 902). The verifier party data includes a unique identifier of the verifier party ("unique verifier party identifier"). The unique verifier party identifier may be an identifier, such as number, that is assigned to all entities in a certain class. The unique identifier may be a preexisting identifier assigned to verifier parties of a certain class (e.g. an educational institution number, a business number).

The database 1302 may be an existing external database. The existing external database may be a database maintained by a governmental entity.

In an example, the validation database 1302 may include a plurality of business numbers. The business number may be a unique number of N digits that serves as a standard identifier for businesses in a jurisdiction (e.g. a unique 9-digit number in Canada). In another example, the validation database 1302 may include a plurality of educational institution numbers. The educational institution number may be a N-digit code (e.g. a four-digit Educational Institution Code in Canada).

The remote verification device 902 sends the unique verifier party identifier to the vault 304 as part of request 908. The request 908 is a request for immunization statuses for a batch on individuals and may be an initial request (e.g. to send out an email to get access approval) or a subsequent request after access approval has been given.

The vault 304 is configured to determine the unique verifier party identifier (e.g. business number, educational institution number) from the request 908.

The vault 304 sends a request to the validation database 1302 at 1306 to verify the unique verifier party identifier. The request includes the unique verifier part identifier. The validation database 1302 sends a response at 1306 to the vault 304. The response indicates whether the unique verifier party identifier is valid or invalid. If the identifier is valid, the vault 304 proceeds to verify the immunization status as described herein. If the identifier is invalid, the vault 304 may terminate the request and send a response to the remote verification device 902 indicating the verifier party identifier is invalid.

Validation of the unique verifier party identifier may be performed by the vault 304 for every request 908 received from the remote verification device 902.

The vault 304 also communicates with the external health card validation database 1304, such as by sending requests to and receiving responses from the heath card validation database 1304. Communication between the vault 304 and the external health card validation database 1304 is represented at 1308.

The vault 304 may use the external health card validation database 1304 to validate or verify the health card number 332 provided by the authorizer user in the response 912 received from the authorizer user device 702 approving access by the verifier party to the authorizer user's immunization status.

In an embodiment, the vault 304 may send a request to the database 1304 at 1308 to verify the health card number 332. The request includes the health card number 332. The external health card validation database 1304 sends a response at 1308 to the vault 304. The response indicates whether the health card number 332 is valid or invalid. If the health card number 332 is valid, the vault 304 proceeds to verify the immunization status as described herein. If the health card number 332 is invalid, the vault 304 may terminate the request and send a response to the authorizer user device 702 indicating the health card number 332 is invalid.

In an embodiment, the database 1304 may include a list of valid health card numbers. The database 1304 receives the health card number 332 from the vault 304 and checks the list to determine whether the health card number 332 is on the list (i.e. valid) or not (invalid).

In other embodiments, the database 1304 component may be more sophisticated and include one or more software modules for validating or verifying health card data, such as a barcode image. In such embodiments, the vault 304 may send a request to the database 1304 including the barcode image (or other data) and the database 1304 processes the barcode image to determine whether the health card is valid.

The system 1300 may provide enhanced validation through the databases 1302, 1304, and the operation of the vault 304 to validate or verify one or both parties to the data transaction (the authorizer user/individual and the verifier party/requesting party). This may enhance security of the computer system, including controlling access to potentially sensitive data, which may increase users' and other stakeholders' faith in the system.

The validation database 1302 component may be used in any scenario in which verifying or validating the verifier party requesting an immunization status may be advantageous. For example, validation database 1302 component may be used to verify or validate verifier parties in in-person verification scenarios. In such cases, the in-person verification device 306 may include the unique verifier party identifier in the immunization status request sent to the vault 304.

The external health card validation database 1304 may be used in any scenario in which verifying or validating the health card number of an authorizer user may be advantageous. For example, the external health card validation database 1304 may be used in in-person or remote verification scenarios where the health card number is provided to the vault 304 by either the verification device (e.g. as a barcode image) or the authorizer user device.

Figure 14:
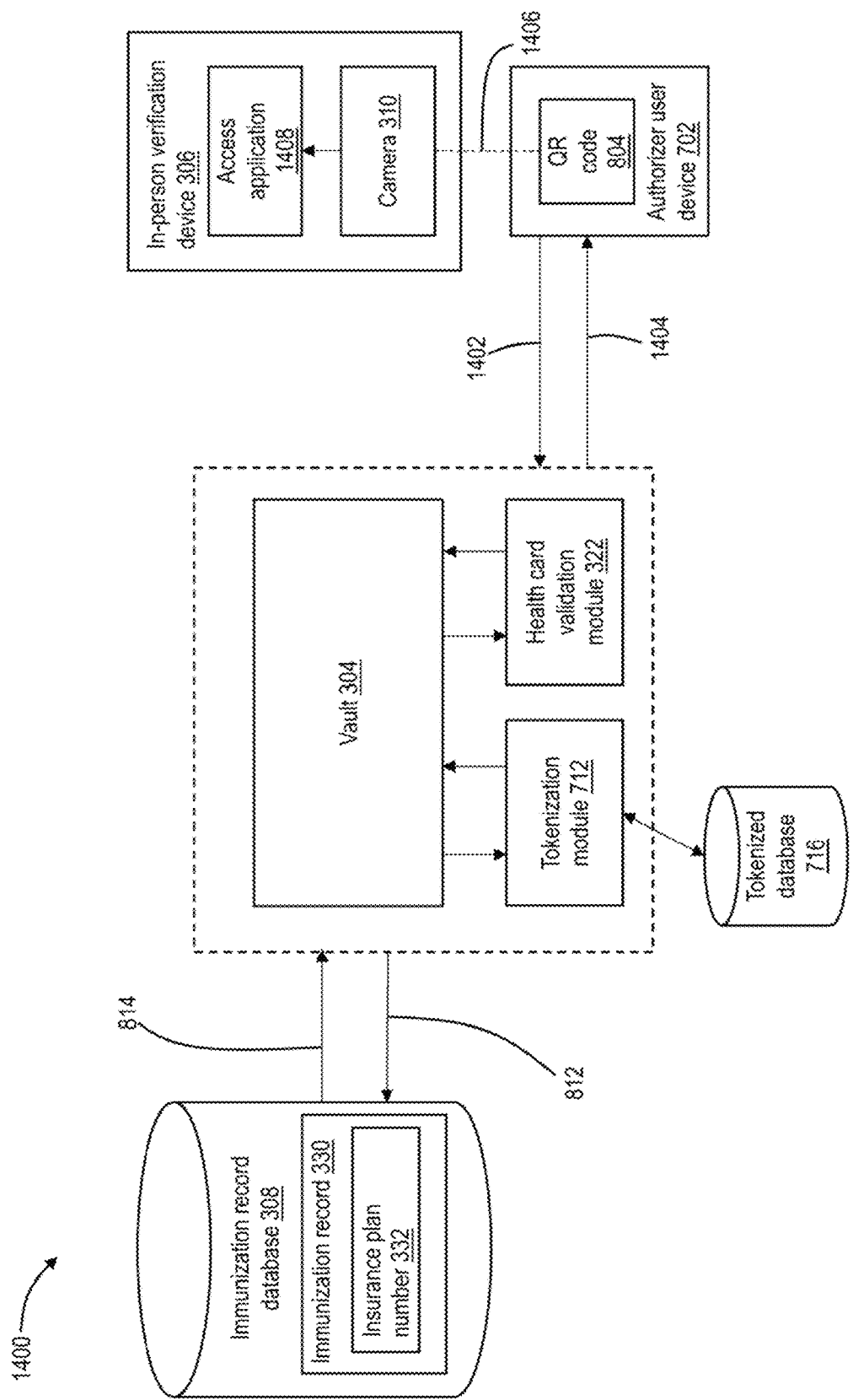
FIG. 14 is a block diagram of a system for offline in-person verification of an immunization status, according to an embodiment.

Referring now to FIG. 14, shown therein is a system 1400 for offline in-person verification of an immunization status, according to an embodiment.

The system 1400 includes components previously described in reference to other figures herein and such components are referenced with like reference numerals. Such components are understood to be capable of performing the same or similar functions as previously described.

The authorizer user device 702 sends a request for an encoded immunization status to the vault 304 at 1402. The request 1402 is made when the authorizer user device is connected to the vault 304 (i.e. online).

The request 1402 includes an insurance plan number 332. The insurance plan number 332 indicates which encoded status is requested. In some cases, the request 1402 may include a barcode image of the health card 302 and the barcode image is processed as described herein to obtain the insurance plan number 332.

The vault 304 determines the immunization status using the insurance plan number 332 as described herein.

The vault 304 includes an encoded immunization status generator module (not shown). The encoded immunization status generator is configured to receive the immunization status determined by the vault 304 (for example as shown in FIG. 11) as input and output an encoded immunization status. The encoded immunization status may be a QR code or the like.

The immunization status may include a validity period that is encoded in the encoded immunization status. The status validity period may be determined by the policy engine of the vault 304. The status validity period may correspond to a period of time for which the individual corresponding to the status would give a PASS immunization status. Generally, the encoded validity period enables the authorizer user to store their status locally on their device 702 and provides a measure of assurance to the verifier party that the status represented in the encoded status is current.

In some cases, the encoded status may include encoded elements from a photograph for visual confirmation of the authorizer user when presented the encoded status to the in-person verification device 306. The photograph from which elements are encoded in the encoded status may be stored at the vault 304 or in a database accessible to the vault 304 (e.g. database 308).

The vault 304 generates the encoded immunization status and sends a response at 1404 to the authorizer user device 702. The response 1404 includes the encoded immunization status 804.

The authorizer user device 702 displays the encoded immunization status 804.

The in-person verification device 306 acquires an image of the encoded immunization status 804 at 1406 using the camera 310.

The in-person verification device 306 includes an access application 1408. The access application 1408 is configured to decode the encoded immunization status to obtain the immunization status. The immunization status is displayed to the user in a user interface of the access application 1408.

In cases where the validity period is encoded in the encoded status, the access application 1408 decodes the encoded status to obtain the status validity period and verifies the validity of the immunization status. The immunization status (taking into account the validity determination) is displayed to the user in a user interface of the access application.

The access application 1408 may be configured to determine whether the encoded status 804 is valid (e.g. whether the validity period is expired or not) and extract a name and immunization status from the encoded status 804. The access application 1408 may include an algorithm for extracting the name and immunization status data from the encoded status 804.

The encoded status 804 may also be printable. In such cases, the encoded status 804 is received by the authorizer user device 702 and subsequently printed to a paper copy (by sending a print command to a connected printer). The printed encoded status may then be presented to the in-person verification device 306 for processing as previously described.

The system 1400 may be considered to have an online setup phase (e.g. 1402, 1404) and an offline phase (e.g. 1406, 1408). In the online phase, the authorizer user device 702 connects to the vault 304 to obtain the encoded immunization status. In the offline phase, the authorizer user device 702 displays the encoded immunization status and the in-person verification device 306 determines whether the encoded immunization status is valid. Advantageously, the offline phase does not require a network connection and can thus be carried out in situations where network connection is unavailable (e.g. where the is no network connection, or if a network connection is lost).

The systems, methods, and devices of the present disclosure have been presented and described in the context of verifying an immunization status of an individual or group of individuals. It is to be understood, however, that the systems, methods, and devices, and components thereof, described herein may have applications beyond the immunization status verification context. In particular, the present disclosure provides systems, methods, and devices for secure data portability. Secure data portability refers broadly to the ability of a first system user to drive their data via a secure gateway or intermediary system (vault 304) to a second system user in a secure and permissioned manner. The secure gateway can call out to external systems (e.g.

databases) to obtain data corresponding to the first system user using some data provided by the first system user (which can act as a key to obtain other data from the external system). Generally, the secure gateway does not store data obtained from the external system. Rather, the secure gateway controls the second system user's access to the first system user's data. In some cases, the secure gateway is configured to strip or transform data received from the external system (e.g. record) such that the data provided to the second system user is limited to the data the first system user has authorized the second system user to receive. For example, the secure gateway may strip out data (e.g. health card number) provided to and used by the secure gateway to obtain data about the first system user from the external system (e.g. immunization record). In a verification scenario, the secure gateway may strip data such that the response to the second system user includes only the data needed to verify (e.g. verify an immunization status, verify a financial transaction). Further, the secure gateway may strip or transform such data according to predetermined rules encoded in a policy engine. The encoded rules may be derived from an external rules database, which may store rules, policies, guideline, regulations, or the like implemented by an external body (e.g. governmental authority).

Figure 15:
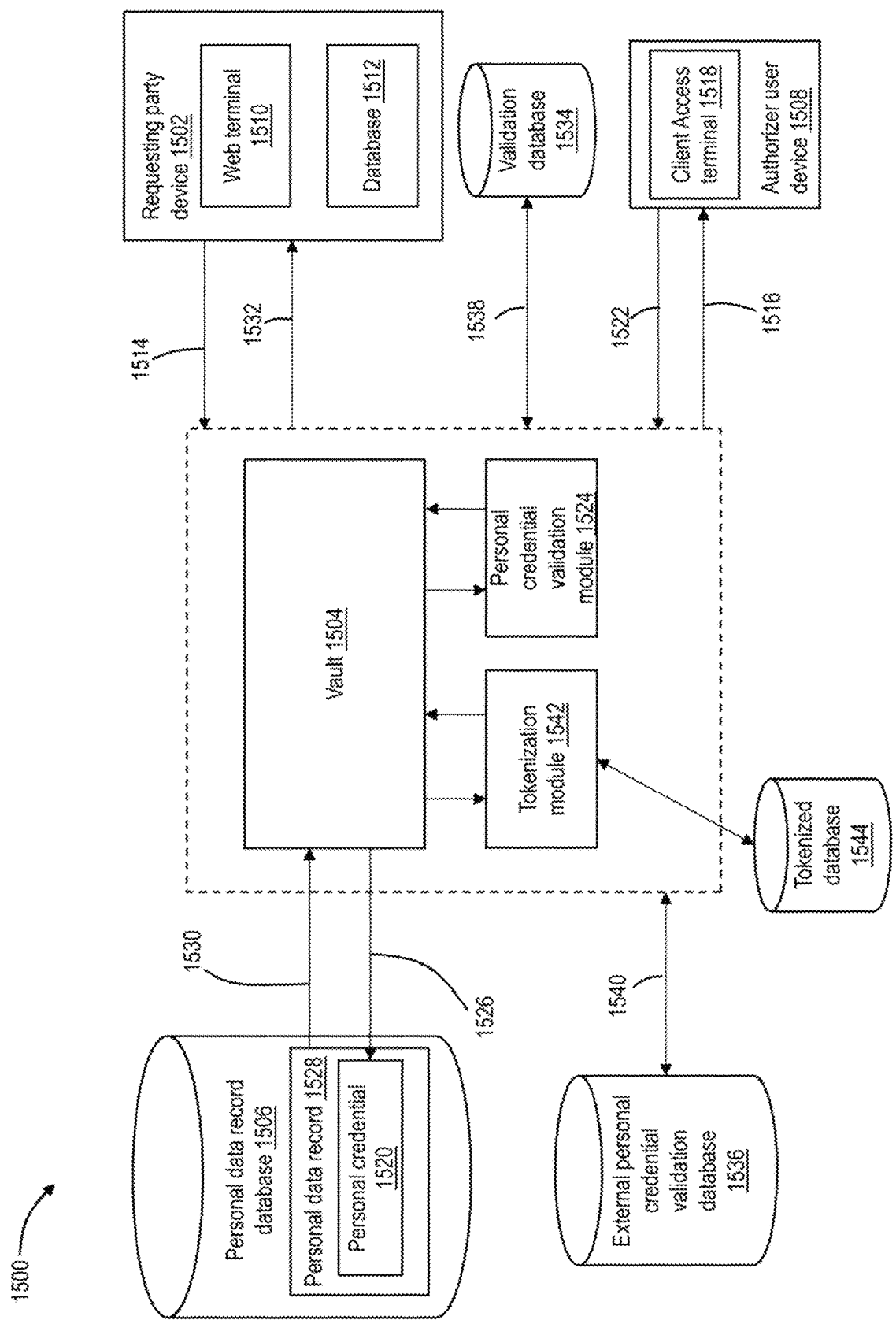
FIG. 15 is a block diagram of a system for remote verification of an information data product generated from personal data, the system including enhanced validation, according to an embodiment.
Figure 16:
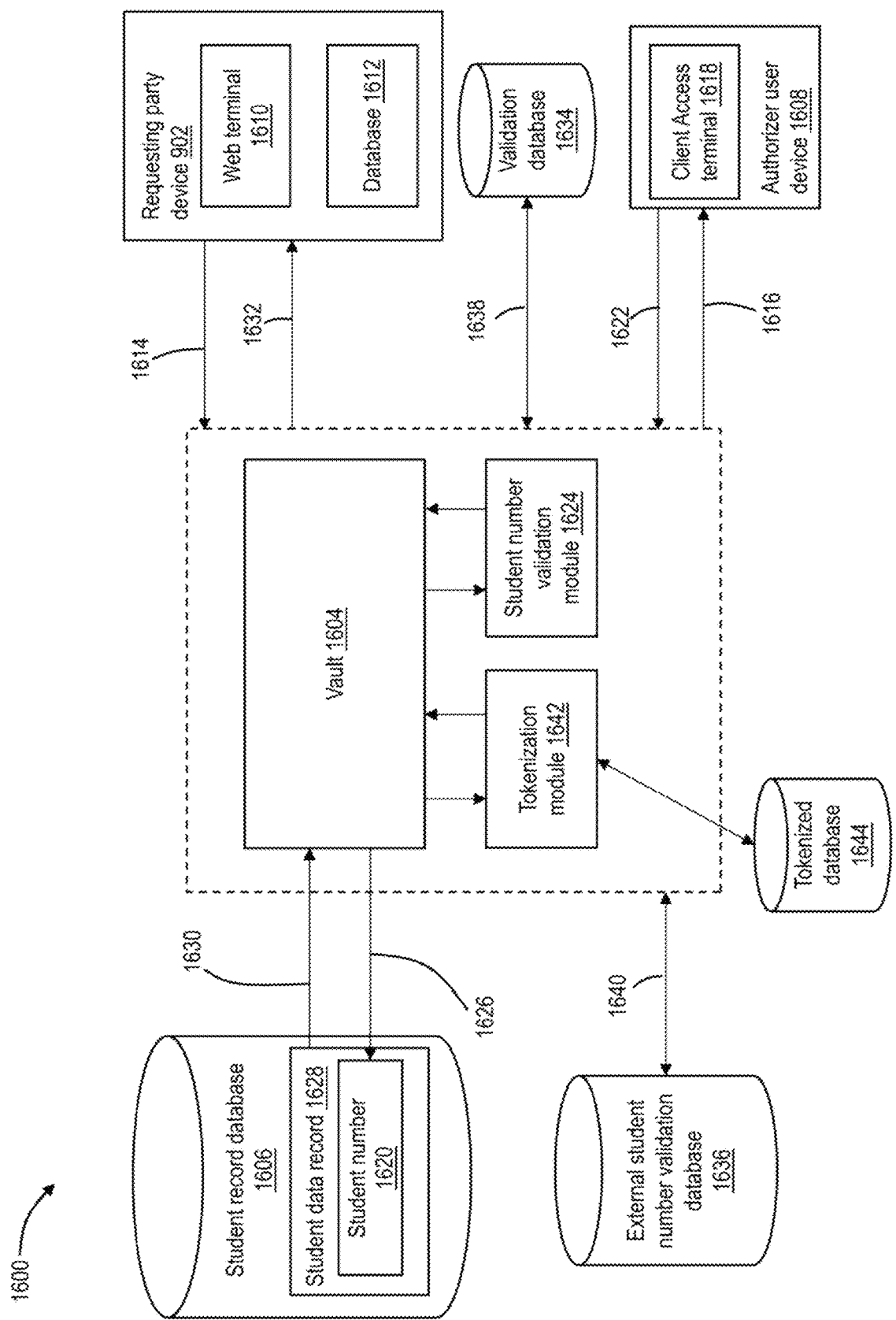
FIG. 16 is a block diagram of a system for remote verification of an academic status of an individual based on a student data record, the system including enhanced validation, according to an embodiment.

FIGS. 15 and 16 will now be described. FIG. 15 illustrates a system 1500 for remote permissioning of access to personal data for processing, according to an embodiment. FIG. 16 illustrates an example implementation 1600 of system 1500 of FIG. 15 for determining an educational status of an individual based on a student data record, according to another embodiment. It is to be understood that system 1600 of FIG. 16 is merely one example implementation of the system 1500 of FIG. 15, and that other applications are contemplated. For example, the systems and methods described herein relating to immunization status verification may be implemented by the system 1500 of FIG. 15 and may be considered an example implementation thereof.

Components of system 1600 that are the same or similar to components of system 1500 are referenced with like reference numbers incremented from 15xx to 16xx. Such components are understood to be capable of performing the same or similar functions. Description of system 1500 and its components is thus understood to apply to system 1600 and its components, even where not expressly noted or where a component of system 1600 is not expressly described.

Referring now to FIG. 15, shown therein is a system 1500 for remote permissioning of access to personal data for processing, according to an embodiment. The system 1500 may be used to provide a first party ("requesting party" or "verifying party") with an information data product generated from a personal data record of a second party ("authorizer user") without providing the requesting party with access to the personal data record of the authorizer user. In the system 1600 of FIG. 16, the requesting party may be an educational institution, licensing body, or any party interested in obtaining an information product derived or generated from a student data record of an individual. The information product may be, for example, be a determination of whether an individual qualifies for enrolling in a course or program, or for admission to a licensing body or the like, based on prerequisite educational requirements. The prerequisite educational requirements may be encoded as policies or rules in the system 1600, such as described below, which can be applied to a student data record (or data elements thereof) of the individual in the determination of the individual's qualification status (e.g. a binary status, such as accept/reject or the like).

The system 1500 may function similarly to the system 1300 of FIG. 13 and provide similar advantages, such as through batch processing of information products for a batch of authorizer users. The system 1500 may provide for remote management of information products of groups of individuals. Such remote management may include management by exception.

The system 1500 includes components previously described in reference to other figures herein. Such components are understood to be capable of performing the same or similar functions as previously described.

The system 1500 includes a requesting device 1502, a vault computing device 1504, a personal data record database 1506, and an authorizer user device 1508. The requesting device 1502, vault 1504, personal data record database 1506, and authorizer user device 1508 may function similarly to the remote verification device 902, vault 304, immunization record database 308, and authorizer user device 702 described herein (such as, for example, in FIGS. 9 and 13). The personal data record database 1508 is a database that is not operated by or generally accessible to the requesting party. In the system 1600 of FIG. 16, the personal record database 1506 is a student record database 1606.

The requesting party device 1502 includes a web terminal 1510. The requesting device 1502 communicates with the vault 1504 via the web terminal 1510. The web terminal 1510 may function similarly to the web terminal 312 or 904.

The requesting party device 1502 includes a database 1512. The database 1512 stores data about a group of individuals (authorizer users) who have a structured relationship with the requesting party. Generally, the data in the database 1512 includes some identifying information about the individuals (e.g. email address). For example, the requesting party may be an employer, an airline, a school, a border crossing agency, a financial institution, an education institution, etc., and the individuals may be employees, airline passengers, students, essential workers, clients, etc. In the system 1600 of FIG. 16, the database 1612 may store data about a group of students or applicants who have a structured relationship with the requesting party through enrollment with or application to the requesting party.

The database 1512 includes a unique identifier for each individual. The unique identifier may be an identifier specifically related to the structured relationship, such as a student number, employee number, passenger number, essential worker number, account number, client card number, client number, policy number, etc. The database 1512 also includes an email address for each individual. In other embodiments, the database 1512 may include in addition to or instead of an email address data for another method of contact, such as a mobile phone number (and may use SMS or other message instead of email).

Generally, the database 1512 does not include the personal credential (described herein) for the individuals (though it is possible).

In other embodiments, the requesting party may input data about individuals (e.g. contact data, unique identifier) into the web terminal 1510 via a web interface or the like. The data may be provided as a list. In such cases, the requesting party device 1502 may not have the database 1512. In an example, the web terminal 1510 may include a user interface for pasting or otherwise inputting a list of individuals to whom requests (for permissioned access to personal data) are to be sent.

The requesting party device 1502 sends a request at 1514 to distribute email authorization requests to specified authorizer users (i.e. individuals in the database 1512). The request 1514 is basically a request for the vault 1504 to forward access requests to specified individuals.

Generally, the request 1514 may specify a batch of individuals in database 1512 for which the requesting party wants an information data product. The batch may be in a CSV format. The batch may be in an XLS format. The batch may be provided via a web interface. In some cases, the request may be for an individual.

The request 1514 specifies contact data (e.g. an email address, a mobile phone number) for a plurality of individuals. In FIG. 15, the contact data is an email address. In other embodiments, the contact data may relate to another method of electronic communication, such as a mobile phone number for text message-based communication (e.g. SMS).

The request 1514 may include other data for each individual, such as the unique identifier (e.g. account number, client number, student number, client card number etc.).

The request 1514 may include a list of email addresses and corresponding unique identifiers. For example, the request 1514 may include a list of [email, Identifier].

The request 1514 may include a terminal ID of the requesting party device 1502.

The vault 1504 receives the request 1514 and generates an email (or other electronic message, as the case may be) to be sent to each individual authorizer user using their respective email address (or other contact information). The email may include a hyperlink. The link is selectable by the recipient and may direct the user to a user interface, such as webpage, where data can be inputted (e.g. the personal credential or other personal data record identifier).

The vault 1504 may include a web terminal validation module (not shown) for validating the web terminal 1510. The web terminal validation module may function similarly to web terminal validation modules described herein (e.g. web terminal validation module 316).

The vault 1504 sends the email to the authorizer user device 1508 at 1516. It is to be understood that this step and the ones that follow are described in the context of a single authorizer user but are performed for a plurality of authorizer users specified in the batch request 1514.

The authorizer user device 1508 includes client access terminal 1518. The client access terminal 1518 may function similarly to client access terminal 708 described herein. The client access terminal 1518 displays the email. The email directs the recipient (e.g. via a link in the email) to a webpage interface for inputting a personal credential 1520 and data access permission (approve access to the information data product).

The personal credential 1520 may be similar and function similarly to insurance plan number 332 described herein. Generally, the personal credential 1520 may be a unique identifier of the authorizer user in the personal data record database 1506. The personal credential 1520 may be any data that can act as a key value for retrieving the personal data record 1528 from the personal data record database 1506 (e.g. "data retrieval key"). For example, the personal data record 1528 may be stored in the personal data record database 1506 such that the personal data record 1528, or a portion thereof (e.g. one or more data elements thereof), can be retrieved using the personal credential 1520 (e.g. by querying the database 1506 using the personal credential 1520). Thus, more generally, the personal credential 1520 may also be considered a key value for retrieving personal data of the authorizer user from the personal data record database 1506 for generating an information product. In the system 1600 of FIG. 16, the personal credential is a student number 1620. In other embodiments of system 1600, the student number 1620 may any other value or data that can act as a key for retrieving the student data record 1628 from the student record database 1606.

The access approval authorizes the requesting party to access the information product generated from the personal data to which access by the requesting party was granted by the authorizer user. The permission may be inputted by selecting a user interface element, such as a clickable icon.

The authorizer user inputs the personal credential 1520 and the data access permission via the client access terminal 1518.

In some cases, the authorizer user may be able to specify period of time for which the approved access is granted (e.g. one time use, specifying an end date, until revoked by the user, etc.). For example, the user interface or webpage may be configured such that the user can select or input the permission validity period into the user interface for communication to the vault 1504 via the client access terminal 1518.

The authorizer user device 1508 sends a response at 1522 to the vault 1504. The response 1522 includes the access approval and the personal credential 1520 (if access is granted). If the permission was not authorized, the response 1522 indicates access is not approved.

The vault 1504 receives the response 1522 including the access approval and the personal credential 1520.

The vault 1504 may validate the personal credential 1520 using a personal credential validation module 1524. The personal credential validation module 1524 may function similarly to health card validation module 322 described herein. In system 1600 of FIG. 16, the personal credential validation module is a student number validation module 1624.

The vault 1504 generates and stores a mapping or link between the personal credential 1520 and the email address or unique identifier of the authorizer user. This links the personal credential 1520 to the request. In the system 1600 of FIG. 16, a mapping between the student number 1620 and the unique identifier of the authorizer user links the student number 1620 to the request.

The vault 1504 also stores access approval data for the access approval provided by the authorizer user 1508 in the response 1522. The access approval data is linked to the authorizer user. This may include linking the access approval data to any one or more of the personal credential 1520, the unique identifier, and the email address (or other contact data). The access approval data may include a permission validity period. The permission validity period may be a one-time access, a defined period of time, or until revoked by the authorizer user. Revocation of permission by the authorizer user may be achieved through user input provided at the client access terminal 1618. The permission validity period may be included in the response 1522 provided by the authorizer user device 1508. The permission validity period may be inputted to the client access terminal 1518 by the authorizer user (e.g. in a web interface).

The access approval data may also be linked to a unique identifier of the requesting party. For example, the unique identifier of the requesting party may be the terminal ID of the requesting party device 1502, or other identifier such as a business number, educational institution number, financial institution number, etc. In the system 1600 of FIG. 16, the unique identifier of the requesting party may be an educational institution number or the like.

In an embodiment, the access approval data stored in the vault 1504 may include an access approval (permission to access the information product and personal data for generating the information product), an access approval validity period, a unique identifier of the party authorizing access (authorizer user), and a unique identifier of the party who is authorized to access (verifier party). The access approval data may enable the verifier party to inquire multiple times about the information products of a batch of individuals without requiring input from the authorizer user other than the initial access approval (provided by response 1522). In some cases, since unique identifier number sets may overlap, an extended unique identifier number may be used. The extended unique identifier may be used to effectively build an identifier that includes an identifier component for the verifier party and a component for the authorizer user. For example, an employer may have a business number and a 5-digit employee number (for an individual or authorizer user for which an information product is requested). The unique identifier associated with requests from that employer may be of the form xxxxxxx.yyyyy, where xxxxxxx is the business number and yyyyy is the employee number. In another example, a financial institution requesting party may have an X-digit financial institution number and a X-digit client number or account number for the authorizer user.

The vault 1504 sends a personal data record request at 1526 to the personal data record database 1506. The request 1526 includes the personal credential 1520. In system 1600 of FIG. 16, a request 1626 including the student number 1620 is sent from the vault 1604 to the student record database 1606.

The personal data record database 1506 retrieves a personal data record 1528 (or subset thereof, such as one or more data elements contained in the personal data record 1528) using the personal credential 1520 and sends a response at 1530 to the vault 1504 including the personal data record 1528.

In the system 1600 of FIG. 16, the student record database 1606 retrieves a student data record 1628 using the student number 1620 in the request 1626. Retrieving the student data record 1628 may include retrieving the entire student data record 1628 or retrieving only a subset of the data in the student data record 1628, such as one or more data elements contained in the student data record 1628. For example, a student data record 1628 may include, for each course taken by the student (for which the database 1606 operator has a record), a course code identifying the course, a date when the course was taken or completed, and a grade or mark. The grade or mark may include categorical (e.g. pass/fail, A/B/C) or numerical (e.g. a grade point average, 90%) data elements. In some cases, the student data record 1628 may be complex and include data elements related to evaluations taken throughout the course (e.g. a grade on Test 2 or Midterm 1, a grade on Assignment 3, a grade on lab work, etc.). In such cases, it can be understood how the student data record 1620 retrieved from student record database 1628 may be tailored to the needs of the requesting party. For example, a requesting party may only want to determine that the authorizer user received a grade of at least 70% in each of courses A and B, which may be a prerequisite for enrollment in another course or program or for admission to a professional designation. The student data record 1620 may store a course code for each of courses A and B and a plurality of data elements relating to specific evaluations in the respective courses (and each of those plurality of data elements may have a plurality of data elements describing the evaluation, such as an identifier, a grade, a mean, a date completed, etc.). The student data record 1620 retrieved using the student number 1620 and sent to the vault 1604 may include a data record of one or more data elements for each of courses A and B (e.g. at least a course identifier and a final grade).

Generally, data records 1528, 1628 may be similar to other data records described herein, such as immunization record 330. Data records 1528, 1628 may vary in size and complexity.

The vault 1504 receives the response 1530 and inputs the personal data record data 1528 into a policy engine (not shown). The policy engine outputs an information product. The information product may be a determination made on the personal data record data 1528, such as by applying some processing to the personal data record data 1528 based on at least one policy.

Generally, an information data product (or information product) may be considered any data output that is generated from processing the personal data record data 1528 based on at least one policy and that has some informative quality for the requesting party, such as providing some information about the authorizer user that the requesting party desires to know. One example of an information data product is an immunization status, such as described herein. More generally, the information data product may indicate a status of the authorizer user in respect of the at least one policy used to process the personal data record 1528. In the academic context, as in system 1600, the status may be whether an individual meets certain prerequisite requirements for enrollment or entry. In another example, the status may be an individual's qualification for a financial product, such as a loan or line of credit, determined based on personal data of the individual and one or more policies for determining qualification. In another example, the status may be an individual's credit status determined based on the individual's personal financial data and one or more policies for determining an individual's credit status. In another example, the status may be a check on an individual's criminal record to determine whether the individual has a record that is clean with respect to concerns of the requesting party. Such status determinations provided through the information product may be a binary status determination (e.g. pass/fail, accepted/rejected, etc.) or multiclass status determination (where the output is assigned to one of three or more classes). The information data product may indicate the status determination and may also provide additional contextual data. For example, the status determination for a loan application may be "approved" or "rejected" and a credit score on which the status determination "approved/rejected" was made. The status determination for a loan application may be "approved" and with an amount (contextual data). The status determination for a loan application may be "rejected" and with a reason (contextual data). In other cases, the contextual data may not be included. Such an approach may be desired where it is desired to limit the amount of information the requesting party receives about the authorizer user.

In some cases, information products (e.g. a batch) can be filtered or otherwise further processed based on requesting party requirements. Such requesting party requirements may be considered secondary contextual requirements or rules that the requesting party wishes to apply on top of the one or more policies used to generate the information data product. For example, the requesting party requirements may be specific requirements of a particular requesting party (e.g. a specific educational institution) or of a particular class of requesting party (e.g. a particular class or type of financial institution, or a particular class/type of educational institution). "Status filtering" of immunization statuses described herein is one example of secondary context processing on an information product and other examples may operate similarly. The secondary context processing may be performed by the vault 1504. For example, the vault 1504 may include a secondary context processing module that encodes rules or criteria for filtering or otherwise processing an information product generated by the vault 1504. One such example is a verifier party The rules may be provided by the requesting party. The rules may be provided to the vault 1504 via a web interface at the requesting party device 1502.

The vault 1504 sends a response at 1532 to the remote verification device 1502. The response 1532 includes the information product. The response 1532 may include an information product for each authorizer user that has access approval data in the vault 1504 (the access approval provided in response 1522). The response 1532 includes data describing the individual corresponding to each information product. The data may be the unique identifier of the individual or the email address (or other contact data). Generally, the data used to describe the individual corresponding to the information product is present in the database 1512 such that the information product can be linked to the individual in the database 1512. For example, in the system 1600 of FIG. 16, the batch request at 1614 may include a student identifier of the potential authorizer user and email address for the potential authorizer user in the batch request. Each student is represented in the database 1612 by the student identifier. The response 1632 from the vault 1604 includes the information products and corresponding student identifiers for each information product (e.g. [Identifier, information product]). In this way, the received information product may be integrated into the database 1512. Also, there is no need to share personal information of the student beyond what is already known by the requesting educational institution (i.e. what is already in the database 1612).

The response 1532 may include a key (e.g. [validity time]) for subsequent direct access by the requesting party.

The response 1532 may include an information product validity period. This may be the case where the information product includes data, such as a status or state, that may change over time (e.g. from valid to invalid), particularly in respect of the at least one policy used to generate the information product. The information product validity period indicates how long the determined information product is valid. The information product validity periods can be monitored by the requesting party to identify individuals with an impending change in information product status (e.g. PASS to FAIL). The requesting party may be able to set an automatic request via the web terminal 1510. This feature may enable the requesting party to set an automatic request time for a particular individual based on the status validity period for that individual.

In some embodiments, status validity periods may be stored at or otherwise accessible to the vault 1504. The status validity periods may be linked to other data, such as a personal credential 1520 (for an authorizer user) or a unique individual identifier (for a requesting party). The stored status validity period may be linked to contact data for reporting a status change (or impending status change). The vault 1504 may be configured to monitor the stored status validity periods for a state change (e.g. PASS to FAIL) or an impending state change (e.g. PASS to FAIL within 14 days). Upon identifying a state change (or impending state change), the vault 1504 may be configured to send a message (e.g. email, text message) to a user (authorizer user, verifier party user) that is linked to the status validity period. Accordingly, data identifying an authorizer user and/or a requesting party may be linked to the status validity period. The data may include contact data for the user (e.g. email address, phone number for text message). The message may indicate that a status state change has taken place or is scheduled to take place at a specified time.

By storing the access approval data of the authorizer users at the vault 1504, the requesting party device 1502 (and the requesting party user) can send requests similar to request 1514 for the information products of a batch of individuals at multiple points in time during which the access approval is valid. For example, in a school scenario, the access approval validity period may be for a school year, and the school (requesting party) may inquire about the information products of its students on a regular basis or interval.

The system 1500 may provide for efficient validation or verification of information products for groups. They system 1500 may leverage a structured relationship of some sort that exists between the requesting party and the authorizer users (i.e. the requesting party knows some information about the authorizer users) to enable the provision of permissioned access from the authorizer user to the requesting party to receive an information product generated from personal data of the authorizer user with having the requesting party access, store, or see the personal data.

For example, the system 1600 of FIG. 16 may be used to provide an information data product for each of a plurality of students enrolled in an academic course or program to an instructor (requesting party). The information data products may be requested and provided as a batch. In a particular example, an instructor (requesting party) may wish to know, even though the students have satisfied the prerequisites to enroll in a course, whether the students achieved a sufficient grade or mark in a subcomponent of a prerequisite course to determine whether the incoming students have demonstrated proficiency in that subcomponent. By receiving information data products indicating whether a student has demonstrated subcomponent proficiency as a batch (reflecting the students enrolled in the course), the instructor may be able to determine the level of proficiency of the incoming class with respect to the subcomponent and, depending on the determination, adjust the course teaching to better suit the proficiency of the incoming class. In such an example, the student data record 1628 may include data elements corresponding to a grade in subcomponent of the prerequisite course, such as a lab, unit, test, or exam. The rules used to process the student data record 1628 into an information data product may include determining whether a student has achieved a grade of at least 70% in subcomponent A of prerequisite course C (or in each of subcomponent A and subcomponent B, average of 70% in subcomponents A and B, etc.). The information data product may include a binary status indicator (e.g. yes/no) indicating whether the criteria is satisfied (i.e. proficiency status) for each student in the batch (class). The information data product may be sent to the requesting party device 1602 where it can be displayed, for example via web terminal 1602. In some cases, the information data product may be transformed into a human readable representation of the proficiency status, which may be a binary status indicator, for display (e.g. checkmark or 'X', green or red indicator, etc.). The foregoing is one example of how the remote batch permissioning and processing of personal data records in the educational context (student data records) may be advantageous.

More generally, within the educational context, there are many instances that would benefit from a batched request. Educational settings have existing groupings that may benefit from being able to perform a bulk information request on a population of individuals, such as may be performed by the systems described herein (e.g. systems 1500, 1600). Examples of typical groupings in educational settings include the students in a course, students in a club, and students in a particular year or program. Such groupings, and the members thereof, may be reflected in data stored by the requesting party at database 1612.

Some of the detailed information that a teacher or administrator may want to know, and which may be provided by the system 1600, may be a detail (represented in one or more data elements) in the student data record 1628 that is relevant for a particular task. For example, imagine a science teacher who is considering a lab assignment for a course. The students in the teacher's class may all have adequate marks from a prerequisite course but may have poor marks from the lab component of that prerequisite course. Using the system 1600, the teacher (as the requesting party and via requesting party device 1602) could launch a bulk enquiry for the members of his class and have the vault 1604 return a set of binary responses to the question "Which of these [list of] students have a mark over 65% in the lab component of the prerequisite course?". The response may be an ordered set of binary information indicating which students passed, and which students did not (i.e. which students achieved over 65% and which did not). This information can help the teacher adjust the lab component of the current course to be safer and more instructive.

Batch remote permissioned access functionalities provided by system 1500 may apply in other contexts as well. For example, in a banking or other employment context, there are natural groupings where permissioned knowledge may be useful for leadership personnel to be able to make inquiries about potentially sensitive information without holding the information. In a particular example, an employer may need to know for a population of employees, if there is adequate representation by designated minority groups. In such an example, the system 1500 of FIG. 15 may be used by a requesting party to make a bulk enquiry for the employee permissioned data fields (e.g. personal data record 1528) in a database holding minority identification status (e.g. personal data record database 1506) would be an efficient way to answer the question. A response may be determined by the vault 1504 as an information data product indicating minority identification status for a batch of employees. The information data product may represent the status (yes/no) in a binary format.

The system 1500 may provide various advantages. For example, the vault 1504 links the personal credential 1520 provided by the authorizer user to the unique identifier for the authorizer user that is known by the requesting party (e.g. student number, email address, employee number, account number, client number, etc.). In doing so, the requesting party does not need to know or store the personal credential 1520. The contact data for the authorizer user provided by the requesting party is sufficient to contact the authorizer user and obtain the personal credential 1520 (and access approval).

The system 1500 may include a validation database 1534 ("requesting party validation database") and an external personal credential validation database 1536. In the system 1600 of FIG. 16, the external personal credential validation database is an external student number validation database 1636.

The vault 1504 communicates with the validation database 1534, such as by sending requests to and receiving responses from the validation database 1534. Communication between the vault 1504 and the validation database 1534 is represented at 1538.

Generally, the validation database 1534 stores data on a plurality of requesting parties (operators of the requesting party device 1502). The requesting party data includes a unique identifier of the requesting party ("unique requesting party identifier"). The unique requesting party identifier may be an identifier, such as number, that is assigned to all entities in a certain class. The unique identifier may be a preexisting identifier assigned to requesting parties of a certain class (e.g. an educational institution number, a business number, financial institution number). In the system 1600 of FIG. 16, the validation database 1634 may include a unique identifier of an educational institution (or other requesting party), such as an educational institution number.

The database 1534 may be an existing external database. The existing external database may be a database maintained by a governmental or regulatory entity.

In an example, the validation database 1534 may include a plurality of business numbers. The business number may be a unique number of N digits that serves as a standard identifier for businesses in a jurisdiction (e.g. a unique 9-digit number in Canada). In another example, such as in FIG. 16, the validation database 1534 may include a plurality of educational institution numbers. The educational institution number may be a N-digit code (e.g. a four-digit Educational Institution Code in Canada). In another example, the validation database 1534 may include a plurality of financial institution numbers. The financial institution numbers may be an N-digit code.

The remote verification device 1502 sends the unique requesting party identifier to the vault 1504 as part of request 1514. The request 1514 is a request for information products for a batch on individuals and may be an initial request (e.g. to send out an email to get access approval) or a subsequent request after access approval has been given.

The vault 1504 is configured to determine the unique requesting party identifier (e.g. business number, educational institution number, financial institution number) from the request 1514.

The vault 1504 sends a request to the validation database 1534 at 1538 to verify the unique requesting party identifier. The request includes the unique requesting party identifier. The validation database 1534 sends a response at 1538 to the vault 1504. The response indicates whether the unique requesting party identifier is valid or invalid. If the identifier is valid, the vault 1504 proceeds to generate the information product as described herein. If the identifier is invalid, the vault 1504 may terminate the request and send a response to the requesting party device 1502 indicating the requesting party identifier is invalid.

Validation of the unique requesting party identifier may be performed by the vault 1504 for every request 1514 received from the requesting party device 1502.

The vault 1504 also communicates with the external personal credential validation database 1536, such as by sending requests to and receiving responses from the personal credential validation database 1536. Communication between the vault 1504 and the external personal credential validation database 1536 is represented at 1540.

The vault 1504 may use the external personal credential validation database 1536 to validate or verify the personal credential 1520 provided by the authorizer user in the response 1522 received from the authorizer user device 1508 approving access by the requesting party to the authorizer user's information product. For example, in system 1600 of FIG. 16, the external student number validation database 1636 may validate or verify the student number 1620 provided by the authorizer user.

In an embodiment, the vault 1504 may send a request to the database 1536 at 1540 to verify the personal credential 1520. The request includes the personal credential 1520. The external personal credential validation database 1536 sends a response at 1540 to the vault 1504. The response indicates whether the personal credential 1520 is valid or invalid. If the personal credential 1520 is valid, the vault 1504 proceeds to generate the information product (which may include a determination made based on processing of personal data retrieved using the personal credential 1520) as described herein. If the personal credential 1520 is invalid, the vault 1504 may terminate the request and send a response to the authorizer user device 1508 indicating the personal credential 1520 is invalid.

In an embodiment, the database 1536 may include a list of valid personal credentials. The database 1536 receives the personal credential 1520 from the vault 1504 and checks the list to determine whether the personal credential 1520 is on the list (i.e. valid) or not (invalid).

The system 1500 may provide enhanced validation through the databases 1534, 1536, and the operation of the vault 504 to validate or verify one or both parties to the data transaction (the authorizer user/individual and the requesting party). This may enhance security of the computer system, including controlling access to potentially sensitive data, which may increase users' and other stakeholders' faith in the system.

The validation database 1534 component may be used in any scenario in which verifying or validating the requesting party requesting an information product may be advantageous or desirable.

The external personal credential validation database 1536 may be used in any scenario in which verifying or validating the personal credential 1520 of an authorizer user may be advantageous or desirable. For example, the external personal credential validation database 1536 may be used in in-person or remote verification scenarios where the personal credential 1520 is provided to the vault 1504 by either the requesting device 1502 or the authorizer user device 1508.

The vault 1504 may also include a tokenization module 1542. The vault 1504 provides the personal credential 1520 and alternate authentication credential data (e.g. alt-ID 706, login/password) as input to the tokenization module 1542. The tokenization module 1542 generates tokenized data from the personal credential 1520 and alternate authentication credential data and stores the tokenized data in a tokenized database 1544. The tokenized database 1544 may be an external or third-party database service that holds data (e.g. personal credential 1520). The tokenization database 1544 may have the effect of holding the personal credential 1520 in a form of escrow. Tokenization module 1542 and tokenized database 1544 may function similarly to tokenized module and database 712, 716 described herein.

The tokenization module 1542 is configured to communicate with the tokenized database 1544, such as to send tokenized data to the tokenized database 1544 and receive tokenized data from the tokenized database 1544 upon request. The tokenization module 1542 outputs a personal credential 1520 to the vault 1504. Tokenization may be used for storing the personal credential 1520 in a database separate from the vault 1504. Such storage configuration may provide advantages. Once the identity of the individual and the associated personal credential 1520 is established, the actual personal credential can be securely stored at a different site and accessed and referenced through a substitute number (token). This token can then be used in lieu of a personal credential to pass data access requests to the database server 1506. Tokenized access may advantageously protect the actual personal credential from being disclosed, thus reducing the opportunity for fraud or unauthorized access.

The tokenization module 1542 and the tokenized database 1544 may advantageously remove the need for the vault 1504 to store or hold personal credential 1520 or other potentially sensitive data.

In an embodiment, the tokenization module 1542 may generate a tokenized ID that is linked to the personal credential 1520. The tokenized ID may be the representation of the personal credential 1520 that is stored in the vault 1504. The personal credential 1520 is stored in the tokenized database 1544, which is located external to the vault 1504. Once established, the tokenized ID may be used to retrieve the personal credential 1520 from the tokenized database 1544 when needed (e.g. for request 1526).

Figure 17:
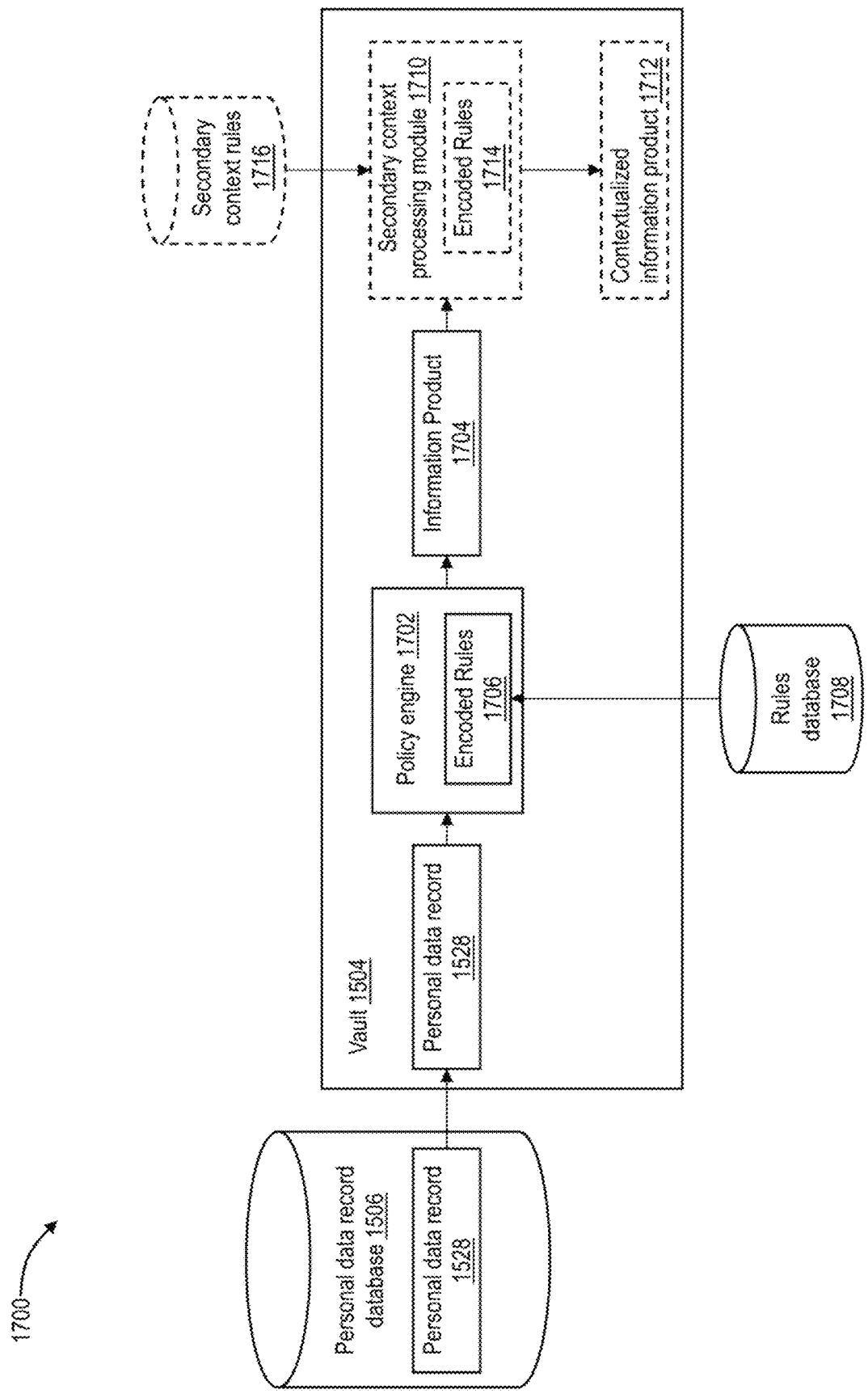
FIG. 17 is a block diagram of information data product generation at the vault computing device of FIG. 15 using a policy engine, according to an embodiment.
Figure 18:
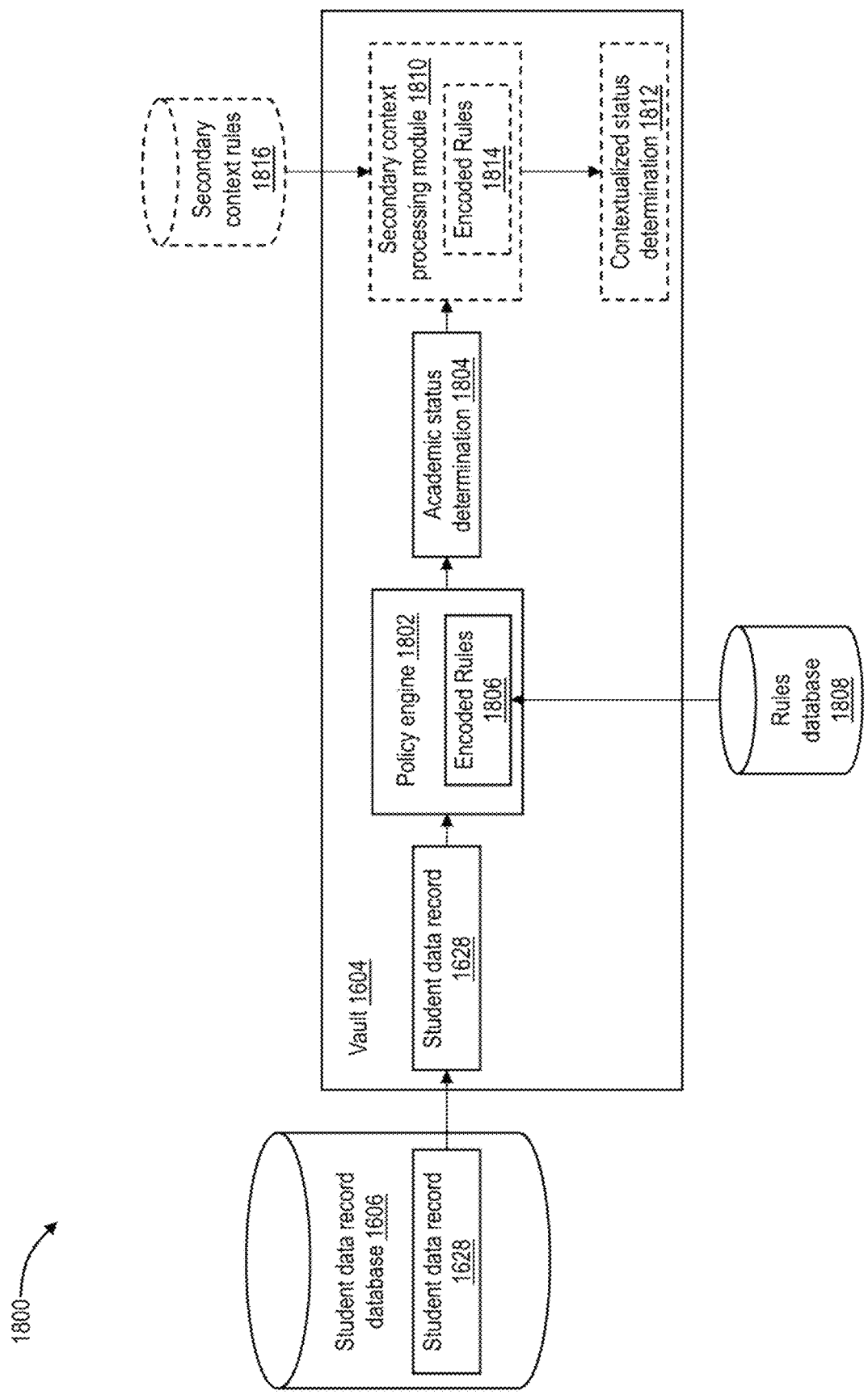
FIG. 18 is a block diagram of an academic status determination at the vault computing device of FIG. 16 using a policy engine, according to an embodiment.

Referring now to FIG. 17, shown therein is a representation 1700 of generation of an information product performed at vault 1504 of FIG. 15, according to an embodiment. FIG. 18 illustrates an embodiment 1800 of representation 1700 in an education or academic data access context in which an information product is generated at vault 1604 of FIG. 16. It is to be understood that system 1800 of FIG. 18 is merely one example implementation of the system 1700 of FIG. 17, and that other applications are contemplated. For example, the systems and methods described herein relating to immunization status verification may be implemented by the system 1700 of FIG. 17 and may be considered an example implementation thereof.

Components of system 1800 that are the same or similar to components of system 1700 are referenced with like reference numbers incremented from 17xx to 18xx. Such components are understood to be capable of performing the same or similar functions. Description of system 1700 and its components is thus understood to apply to system 1800 and its components, even where not expressly noted or where a component of system 1800 is not expressly described.

The vault 1504 is in communication with and receives a personal data record 1528 from the personal data record database 1506.

The vault 1504 provides the personal data record 1528 as input to a policy engine 1702. The policy engine 1702 determines and outputs an information product 1704 based on the application of at least one policy to the personal data record 1528. As described herein, the information data product 1604 may be considered any data output that is generated from processing the personal data record data 1528 based on at least one policy and that has some informative quality for the requesting party, such as providing some information about the authorizer user (to whom the personal data record 1528 relates) that the requesting party desires to know. One example of an information data product 1704 is an immunization status, such as described herein. More generally, the information data product 1704 may indicate a status of the authorizer user in respect of the at least one policy used to process the personal data record 1528.

In the system 1800 of FIG. 18, the vault 1604 provides the student data record 1628 as input to policy engine 1802. The policy engine 1802 determines and outputs an academic status determination 1804 (information data product). The academic status determination 1804 includes a determination of the authorizer user's status in respect of the at least one policy applied by the policy engine 1802 to the student data record 1628. For example, the academic status determination 1804 may be a determination of whether to enroll or admit the authorizer user into an academic course or program. In an embodiment, the academic status determination 1804 may be a binary representation of an information status (e.g. PASS/FAIL, accept/reject, yes/no) with respect to the authorizer user.

The policy engine 1702 includes encoded rules 1706. The encoded rules 1706 are used to process the personal data record 1528 to generate the information product 1704. The encoded rules 1706 represent software logic that is implemented by the policy engine 1702. The encoded rules 1706 may be in the form of a decision matrix.

The encoded rules 1706 are representations of one or more rules, policies, criteria, guidelines, or regulations (collectively, "rules") issued by a relevant authority or body related to the information product. In one example, the rules may specify policies or criteria determining whether for issuing a loan should be issued by the requesting party to the authorizer user or whether the requesting party should offer or provide a financial product to an authorizer user. Generally, in such an example, the policies or criteria consider data represented in the personal data record 1528, and the system 1700 makes a determination by operating on the personal data record 1528 using the encoded rules 1706. The foregoing is one example, and the nature and content of the rules is not particularly limited.

In some cases, the rules may be codable as human readable rules (e.g. a human readable policy). For example, the rules may be expressed in a script file. By having a human readable representation of the rules, such as in a script file, the rules can be read and interpreted by a human user of the system. For example, the system 1700 may be configured send the rules in human readable format from the vault 1504 to the requesting party device 1502, where the human readable rules may be displayed (e.g. in web terminal 1510). Accordingly, in variations of the system 1700, the vault 1504 may include or communicate with a policy translator module configured to translate the encoded rules 1706 into a human readable format.

In some embodiments, the rules may be configurable (whether those reflected in encoded rules 1706 or 1714) may be user configurable. For example, the vault 1504 may generate and send a user interface to the requesting party device 1504 which displays the user interface. The user interface is configured to receive user input. The requesting party device 1502 may generate rules configuration data in response to the user input and send the rules configuration data to the vault 1504. The vault 1504 may then use the rules configuration data to configure and generate a new set of encoded rules.

In the system 1800 of FIG. 18, the encoded rules 1806 may encode policies related to academic prerequisite requirements for enrolling in a certain academic course or program. In a simple example, the encoded rules 1806 may encode a policy specifying that in order for authorizer user to enroll in academic program A, the authorizer user must have received a minimum grade of 70% in academic course B. The policy engine 1802 may then operate on a student data record 1628 (which may include one or more data elements describing authorizer user's grade in academic course B) using encoded rules 1806 to determine whether to enroll authorizer user in academic program A. The determination is outputted at academic status determination 1804.

Rules data representing the rules is stored in a rules database 1708. The rules database 1708 is used to generate the encoded rules 1706. The rules database 1708 may be in communication with or otherwise accessible to the vault 1504. In some cases, the rules database 1708 may be stored at the vault 1504. In such cases, the rules database 1708 at the vault 1504 may be updated from time to time using and external rules database 1708.

In some cases, the rules database 1708 may be maintained by a government entity or regulatory body or authority. The government entity may be, for example, an education authority. The government entity may be a financial regulator or authority.

The encoded rules 1706 may be updated over time using the rules database 1708. For example, policy, rules, criteria, or guidelines may change over time as situations develop. This may be particularly advantageous in dynamic situations, such as pandemics, where information is being acquired in real-time about the disease, virus, and vaccines, or financial market conditions. Accordingly, the vault 1504 may be configured to connect to the rules database 1708 in order to facilitate updating the encoded rules 1706. In some cases, the rules database 1708 may push updates to the vault 1504 and the vault 1504 updates the encoded rules 1706 to reflect the updates to the rules in the rules database 1708.

The vault 1504 may also include a secondary context processing module 1710. The secondary context processing module 1710 receives the information product 1704 as input and outputs a contextualized information product 1712. In some embodiments, the secondary context processing module 1710 may be a component of the policy engine 1702 and the information product 1704 reflects the contextualized information product 1712. Generally, the contextualized information product 1712 represents information product 1704 that has been further processed according to additional rules or criteria specific to a context of relevance or importance to the requesting party, thus being "contextualized" to the context of the requesting party.

The secondary context processing module 1710 includes encoded rules 1714 which represent software logic implemented by the secondary context processing module 1710. The encoded rules 1714 may be similar to encoded rules 1706. In particular, the encoded rules 1714 of the secondary context processing module 1710 represent rules or criteria that a particular requesting party wishes or is required to apply to the information product 1704 to obtain contextualized information product 1712. The encoded rules 1714 may be for a context specific to the requesting party, a context specific to a requesting party class of which the requesting party is one example, or other context (including, in some cases, information about the authorizer user himself). For example, as described herein relating to an immunization status determination, the encoded rules 1714 may include rules or criteria specific to a context of a particular requesting party, a particular class of requesting party (e.g. school, employer, public transportation authority), or a particular class of access scenario (e.g. accessing a restaurant, accessing a sporting event, accessing a concert, accessing a mode of public transportation, etc.). In another example, encoded rules 1706 may relate to minimum financial requirements for issuing a loan or financial product by a financial institution (requesting party) to an authorizer user that may have been issued by a governmental or regulatory authority and encoded secondary context processing rules 1714 may relate to a particular financial institution's (requesting party) requirements or policies for issuing the loan or financial product beyond what is specified in encoded rules 1706. In the system 1800 of FIG. 18, the encoded secondary context rules 1714 may be educational institution-specific policies or requirements with respect to an individual's academic record (i.e. data included in student data record 1628) that are applied to determine whether an individual is enrolled (contextualized information product 1712).

The rules from which the encoded rules 1714 are derived are stored in a secondary context rules database 1716. The secondary context rules database 1716 may be in communication with or otherwise accessible to the vault 1504. The secondary context rules database 1716 may be maintained by the requesting party. In some cases, the secondary context rules database 1716 may be stored at the vault 1504.

In some cases, the secondary context processing module 1610 may include a plurality of masks. Each mask may correspond to a particular set of criteria or rules applicable to a secondary context relevant to the requesting party. The vault 1504 receives data from the requesting device (e.g. requesting device 1502 of FIG. 15) which indicates a set of rules/criteria or mask to apply to the information product 1704. The corresponding mask is applied to the information product 1704 to generate contextualized information product 1712.

In an embodiment, the web terminal (e.g. web terminal 312, 904, 1510) may present a web interface that enables a requesting party to select or input the data for specifying the rules/criteria or mask to apply to the information product 1704. Examples in the immunization status context include the web interface displaying options of "going to a restaurant", "going to a sports event", and "getting on public transit (bus, train, etc.)". The user makes a selection, and the selection data is included with the information product request sent to the vault 1504 (e.g. request 1514 of FIG. 15). The vault 1504 determines the appropriate mask to apply to the information product 1704 from the selection data and applies the mask using the policy engine 1702 or secondary context processing module 1710.

In another embodiment, the system may use different access points or addresses for different sets of criteria/rules/restrictions (e.g. log in to restaurant app if a restaurant, log in to a concert venue app if a concert venue etc.). In general, access point data may be used by the vault 1504 to determine which, if any, secondary context processing rules to apply to the information product 1704. The requesting party may input data indicating the access point via the web terminal 1510. The access point data is included with the information product request sent to the vault 1504 (e.g. at 1514 of FIG. 15). The vault 1504 receives the request and obtains the access point data. The vault 1504 determines the appropriate mask to apply to the personal data record 1528 or information product 1704 based on the access point data and applies the mask.

Generally, the secondary context processing module 1710 may be used to further process information products 1704 according to requesting party-specific rules. This may be particularly useful in remote verification scenarios (e.g. FIG. 9), where a requesting party, such as a school or employer, may have specific requirements.

As previously described in the immunization status context, the secondary context processing module 1710 may be configured to filter information products 1704 of a plurality of authorizer users based on status. This may enable the requesting party to manage statuses of large numbers of individuals more effectively, such as by receiving information on only those individuals with a first status while excluding others with a second status. In other cases, filtering based on status can be done based on validity period of the status, and can be used to identify statuses that may change within a prescribed time period. Such status filtering may provide computational improvements. For example, receiving a subset of information, such as described, makes the result of the query a smaller quantity of data. This can improve speed of transmission of the data, which can also provide power savings, and can increase security as less data is more secure.

The systems, methods, and devices of the present disclosure may provide functional improvements in the functioning of computer systems and devices. Such improvements may include improvements to data security (transmission and storage), processing speed, and processing and storage requirements. Examples are provided below in addition to those described throughout the present disclosure.

In one aspect, the present disclosure provides for precomputing to a minimum required information that can be transmitted to a requesting party device. The minimum required information is represented in the system as an information data product (e.g. immunization status of one individual, immunization statuses of a batch of individuals) generated from the application of at least one policy, encoded in the system as one or more encoded rules, to a personal data record (or only a subset of data elements in the personal data record). In another aspect, the present disclosure provides for retrieving and processing only a subset of data elements in a record that are necessary for determining an information data product based on at least one policy. In other words, the systems described herein may be configured to reduce data sharing through minimizing the data elements retrieved and processing the data elements retrieved to a minimum required information which can then be provided to a requesting party, thus increasing security of the system and improving speed.

For example, in an immunization status application, a full immunization data record may be a page of text and/or on the order of at least several hundred bytes in size. In contrast, the systems described herein may, in some embodiments, generate an immunization status (information data product) that can be represented by one bit (e.g. binary 1 or 0, representing 'pass' and 'fail'. In such a case, the data output transmitted by the system of the present disclosure is significantly smaller than transmitting a full immunization record. As such, the system of the present disclosure can effectively perform data compression prior to transmission through the generation of the information data product (e.g. reflecting minimum required information). This can provide significant data transmission and security advantages, as a smaller data payload, as may be generated and transmitted by the system of the present disclosure (e.g. by vault 1504 to requesting party device 1502), is more secure compared to a larger data payload because the smaller data payload is easier to compress and apply more sophisticated data security techniques thereto (e.g. compression, encryption), meaning larger datasets and payloads are more vulnerable. This may be particularly true in embodiments of the system of the present disclosure that are configured to perform batch premissioning and processing for a plurality of individuals (authorizer users). For example, in a batch case, the system may generate and send an information data product comprising a bit field (e.g. 11010 . . . ) including an immunization status for each individual represented in the batch population, providing significant compression of data. Even in embodiments where the information data product for an individual is not reduced to a single bit (e.g. a binary status indicator output as a information data product, whether on its own or as part of a batch), data compression effects using the system of the present disclosure can be achieved. For example, a data output or information data product in which an individual's status is represented as belonging to one of three or more classes (rather than one of two classes, in a binary case), such data output can be represented on a bit-level (e.g. two bits) rather than byte-level or greater (e.g. several hundred bytes) as would be required when sending the full data record. The foregoing is merely one example of the improvements to the functioning of computer systems provided by the present disclosure and it is understood that such improvements apply to other applications of the systems described herein beyond immunization status verification of the systems described herein.

Accordingly, by generating and providing a minimum required output to a requesting party, data security and processing improvements can be provided by the systems of the present disclosure, which improve the functioning of the computer system.

While the above description provides examples of one or more apparatus, methods, or systems, it will be appreciated that other apparatus, methods, or systems may be within the scope of the claims as interpreted by one of skill in the art.

The invention claimed is:

1. A system for verifying an immunization status of an individual, the system comprising:
   a verification device including a web terminal configured to send an immunization status request, the immunization status request including identifying data about the individual;
   a vault computing device configured to receive the immunization status request and generate and send an immunization record request including an insurance plan number corresponding to the individual;
   an immunization record database server having access to an immunization record database, the immunization record database server configured to retrieve immunization record data from the immunization record database using the insurance plan number and send the immunization record data to the vault computing device;
   the vault computing device further configured to generate immunization status data representing the immunization status of the individual from the immunization record data and send the immunization status data to the verification device;
   the verification device further configured to receive the immunization status data via the web terminal and display the immunization status data in a user interface; and
   the vault computing device further configured to track an immunization batch number to determine whether an immunization batch includes a potential batch-related issue by comparing the immunization batch number to an immunization serial list stored on the immunization record database server, the potential batch-related issue including any one or more of a plurality of warning levels, a good batch status, a vulnerable immunization status, and an ineffective batch status.

2. The system of claim 1, wherein the identifying data is an encoded representation of the insurance plan number decodable by the vault computing device to obtain the insurance plan number, an alternate authentication credential used to obtain the insurance plan number, or contact data for sending an electronic message to the individual to obtain the insurance plan number.

3. The system of claim 1, wherein the immunization status data is a binary status indicator of either a pass or fail.

4. A system for in-person verification of an immunization status of an individual, the system comprising:
   an in-person verification device including:
      an input device for receiving input data of an authentication credential of the individual; and
      a web terminal configured to send an immunization status request, the immunization status request including the input data;
   a vault computing device configured to receive the immunization status request and generate and send an immunization record request including an insurance plan number corresponding to the individual, the insurance plan number determined using the input data;
   an immunization record database server having access to an immunization record database, the immunization record database server configured to retrieve immunization record data from the immunization record database using the insurance plan number and send the immunization record data to the vault computing device;
   the vault computing device further configured to generate immunization status data representing the immunization status of the individual from the immunization record data with respect to an immunization policy and send the immunization status data to the in-person verification device;
   the in-person verification device further configured to receive the immunization status data via the web terminal and display the immunization status data in a user interface; and
   the vault computing device further configured to track an immunization batch number to determine whether an immunization batch includes a potential batch-related issue by comparing the immunization batch number to an immunization serial list stored on the immunization record database server, the potential batch-related issue including one or more of a plurality of warning levels, a good batch status, a vulnerable immunization status, and an ineffective batch status.

5. The system of claim 4, wherein the input device is a camera and the input data is a barcode image of a health card of the individual, and wherein the vault computing device decodes the barcode image to obtain the insurance plan number.

6. The system of claim 4, wherein the input device is a camera and the input data is a barcode image of a non-health card identification card of the individual, and wherein the vault computing device stores a mapping of data encoded in the barcode image to the insurance plan number.

7. The system of claim 4, wherein the input device is a keypad and the input data is a login and password, and wherein the vault computing device stores a mapping of the login and password to the insurance plan number.

8. The system of claim 4, wherein the input device is a camera and the input data is an image of a QR code, and wherein the vault computing device decodes the QR code and obtains the insurance plan number using the decoded QR code.

9. A system for remote verification of an immunization status of an individual, the system comprising:

a remote verification device including a web terminal configured to send an immunization status request, the immunization status request including contact data for the individual;

a vault computing device configured to send an access approval request to the individual using the contact data;

an authorizer user device including a client access terminal configured to receive the access approval request and send a response including an access approval and an insurance plan number;

the vault computing device further configured to send an immunization record request including the insurance plan number;

an immunization record database server having access to an immunization record database, the immunization record database server configured to retrieve immunization record data from the immunization record database using the insurance plan number and send the immunization record data to the vault computing device;

the vault computing device further configured to generate immunization status data representing the immunization status of the individual from the immunization record data and send the immunization status data to the remote verification device; and the vault computing device further configured to track an immunization batch number to determine whether an immunization batch includes a potential batch-related issue by comparing the immunization batch number to an immunization serial list stored on the immunization record database server, the potential batch-related issue including one or more of a plurality of warning levels, a good batch status, a vulnerable immunization status, and an ineffective batch status.

10. The system of claim 9, wherein the immunization status request specifies a plurality of individuals and contact data for each individual, and wherein the vault computing device is configured send access approval requests to each of the plurality of individuals, request the immunization record data for each of the plurality of individuals, generate the immunization status data for each of the plurality of individuals, and send the immunization status data for each of the plurality of individuals as a batch to the remote verification device.

11. The system of claim 9, wherein the immunization status data includes a status validity period.

12. A computing device for offline in-person verification of an immunization status of an individual, the device comprising:

a camera for acquiring an image of encoded immunization status data, the encoded immunization status being an encoded representation of immunization status representing an immunization status of the individual;

a processor executing an access application configured to receive the image as input and decode the encoded immunization status data to obtain the immunization status data; and a display device for displaying the immunization status data;

wherein the processor is further configured to execute a tracking application to track an immunization batch number to determine whether an immunization batch includes a potential batch-related issue by comparing the immunization batch number to an immunization serial list stored on the immunization record database server, the potential batch-related issue including one or more of a plurality of warning levels, a good batch status, a vulnerable immunization status, and an ineffective batch status.

13. The system of claim 12, wherein the immunization status data includes a status validity period.

14. The system of claim 12, wherein the encoded immunization status data is a QR code.

15. A system for enabling an offline in-person verification of an immunization status of an individual, the system comprising:

an authorizer user device including a client access terminal configured to send a request for encoded immunization status data of the individual;

a vault computing device configured to send an immunization record request including an insurance plan number associated with the individual;

an immunization record database server having access to an immunization record database, the immunization record database server configured to retrieve immunization record data from the immunization record database using the insurance plan number and send the immunization record data to the vault computing device;

the vault computing device further configured to generate the encoded immunization status data from the immunization record data, the encoded immunization status data decodable to obtain immunization status data representing the immunization status of the individual, and send the encoded immunization status data to the authorizer user device;

wherein the encoded immunization status data is decodable by an in-person verification device running an access application for decoding encoded immunization status data to obtain the immunization status data without a need for the in-person verification device to be connected to a network; and the vault computing device further configured to track an immunization batch number to determine whether an immunization batch includes a potential batch-related issue by comparing the immunization batch number to an immunization serial list stored on the immunization record database server, the potential batch-related issue including one or more of a plurality of warning levels, a good batch status, a vulnerable immunization status, and an ineffective batch status.

16. The system of claim 15, wherein the request includes the insurance plan number.

17. The system of claim 15, wherein the immunization status data includes a status validity period.

18. The system of claim 15, wherein the encoded immunization status data is a QR code.

19. A computer system for secure data portability, the system comprising a memory and a processor in communication with the memory, the processor configured to:

receive a data access request from a first web terminal associated with a first system user, the data access request for access to first data about a second system user, the data request including a first unique identifier corresponding to the second system user;

confirm an access approval approving the first system user to access the first data, the access approval linked or mapped to the first unique identifier;

send a request to a computing device connected to the computer system via a network connection, the request including a second data retrieval key, the second data retrieval key usable by the computing device to retrieve second data about the second system user from a database, the second data retrieval key provided to the computer system by the second system user via a second web terminal, the second data retrieval key linked or mapped to the access approval and the first unique identifier;

receive the second data from the computing device and process the second data to generate the first data, the processing including stripping sensitive data from the second data so the sensitive data is not exposed to the first system user;

track an immunization batch number to determine whether an immunization batch includes a potential batch-related issue by comparing the immunization batch number to an immunization serial list stored on the immunization record database server, the potential batch-related issue including one or more of a plurality of warning levels, a good batch status, a vulnerable immunization status, and an ineffective batch status send the first data to the first web terminal.

20. The system of claim 19, wherein the system is configured to verify an immunization status of the second system user, and wherein: the first system user is a verifier party, the second system user is an authorizer user, the data access request is an immunization status request, the first data is immunization status data of the authorizer user, the computing device is an immunization record database server, the second data retrieval key is an insurance plan number, the second data is immunization record data of the authorizer user, and the sensitive data is at least a subset of the immunization record data.

21. The system of claim 19, wherein the access approval is preexisting and stored in the memory.

22. The system of claim 19, wherein the processor is further configured to confirm the access approval by:
    sending a request for the access approval and the second data retrieval key to the second web terminal;
    receiving a response from the second web terminal including the access approval and the second data retrieval key; and
    generating the link or map between the access approval, the second data retrieval key, and the first unique identifier.

* * * * *